US011052851B1

(12) United States Patent
Anvari

(10) Patent No.: US 11,052,851 B1
(45) Date of Patent: Jul. 6, 2021

(54) USE OF IOT NETWORK AND IOT RANGING DEVICE FOR A NAVIGATION AND PROTECTION SYSTEM

(71) Applicant: Kiomars Anvari, Walnut Creek, CA (US)

(72) Inventor: Kiomars Anvari, Walnut Creek, CA (US)

(73) Assignee: Kiomars Anvari, Walnut Creek, CA (US)

(*) Notice: Subject to any disclaimer, the term of this patent is extended or adjusted under 35 U.S.C. 154(b) by 0 days.

(21) Appl. No.: 17/145,151

(22) Filed: Jan. 8, 2021

Related U.S. Application Data

(63) Continuation-in-part of application No. 16/828,013, filed on Mar. 24, 2020, and a continuation-in-part of application No. 17/106,137, filed on Nov. 29, 2020, and a continuation-in-part of application No. 16/984,995, filed on Aug. 4, 2020.

(51) Int. Cl.
| | |
|---|---|
| *B60R 21/01* | (2006.01) |
| *B60W 30/095* | (2012.01) |
| *G16Y 40/10* | (2020.01) |
| *G16Y 40/50* | (2020.01) |

(52) U.S. Cl.
CPC ........ *B60R 21/01* (2013.01); *B60W 30/0956* (2013.01); *G16Y 40/10* (2020.01); *G16Y 40/50* (2020.01); *B60R 2021/01013* (2013.01); *B60R 2021/01034* (2013.01); *B60R 2021/01088* (2013.01); *B60W 2554/802* (2020.02)

(58) Field of Classification Search
CPC ......... B60R 21/01; B60R 2021/01013; B60R 2021/01088; B60R 2021/01034; G16Y 40/10; G16Y 40/50; B60W 30/0956; B60W 2554/802
See application file for complete search history.

(56) References Cited

U.S. PATENT DOCUMENTS

| | | | |
|---|---|---|---|
| 8,068,051 B1* | 11/2011 | Osterweil | G01S 7/006 342/28 |
| 2007/0276600 A1* | 11/2007 | King | G08G 1/166 701/301 |
| 2010/0169009 A1* | 7/2010 | Breed | G01S 19/17 701/301 |
| 2011/0286560 A1* | 11/2011 | Pignatelli | H04J 3/0655 375/356 |
| 2012/0271491 A1* | 10/2012 | Spata | G05D 23/19 701/3 |

(Continued)

*Primary Examiner* — Babar Sarwar

(57) ABSTRACT

Developing intelligent systems which take into consideration the economical, environmental, and safety factors of the modern society, is one of the main challenges of this century. Progress in the fields of mobile robots, control architectures, artificial intelligence, advanced technologies, and computer vision allows us to now envisage a smart environment future.

The rise of the connected objects known as the "Internet of Things" (IoT) will rival past technological marvels. This application discloses a time synchronous communication IoT network and IoT ranging device to monitor a smart environment. IoT ranging device uses a time of day (TOD), an absolute time, and a time slot assigned to it by IoT network for ranging in the smart environment in order to avoid interference and collision.

16 Claims, 30 Drawing Sheets

(56) References Cited

U.S. PATENT DOCUMENTS

| | | | | |
|---|---|---|---|---|
| 2013/0144490 | A1* | 6/2013 | Lord | G08G 1/164 |
| | | | | 701/41 |
| 2013/0308504 | A1* | 11/2013 | Nimbalker | H04L 5/003 |
| | | | | 370/281 |
| 2014/0233479 | A1* | 8/2014 | Dahod | H04N 21/631 |
| | | | | 370/329 |
| 2015/0055636 | A1* | 2/2015 | Rausch | H04H 20/34 |
| | | | | 370/336 |
| 2015/0155891 | A1* | 6/2015 | Soliman | H04L 27/2626 |
| | | | | 455/552.1 |
| 2015/0185713 | A1* | 7/2015 | Glickfield | G05B 15/02 |
| | | | | 700/44 |
| 2018/0229684 | A1* | 8/2018 | Anvari | B60R 21/233 |
| 2018/0375887 | A1* | 12/2018 | Dezent | H04L 63/1458 |
| 2019/0311625 | A1* | 10/2019 | Anvari | H04W 4/02 |
| 2019/0335479 | A1* | 10/2019 | Thubert | H04W 40/24 |
| 2020/0029172 | A1* | 1/2020 | Kim | H04N 5/225 |

* cited by examiner

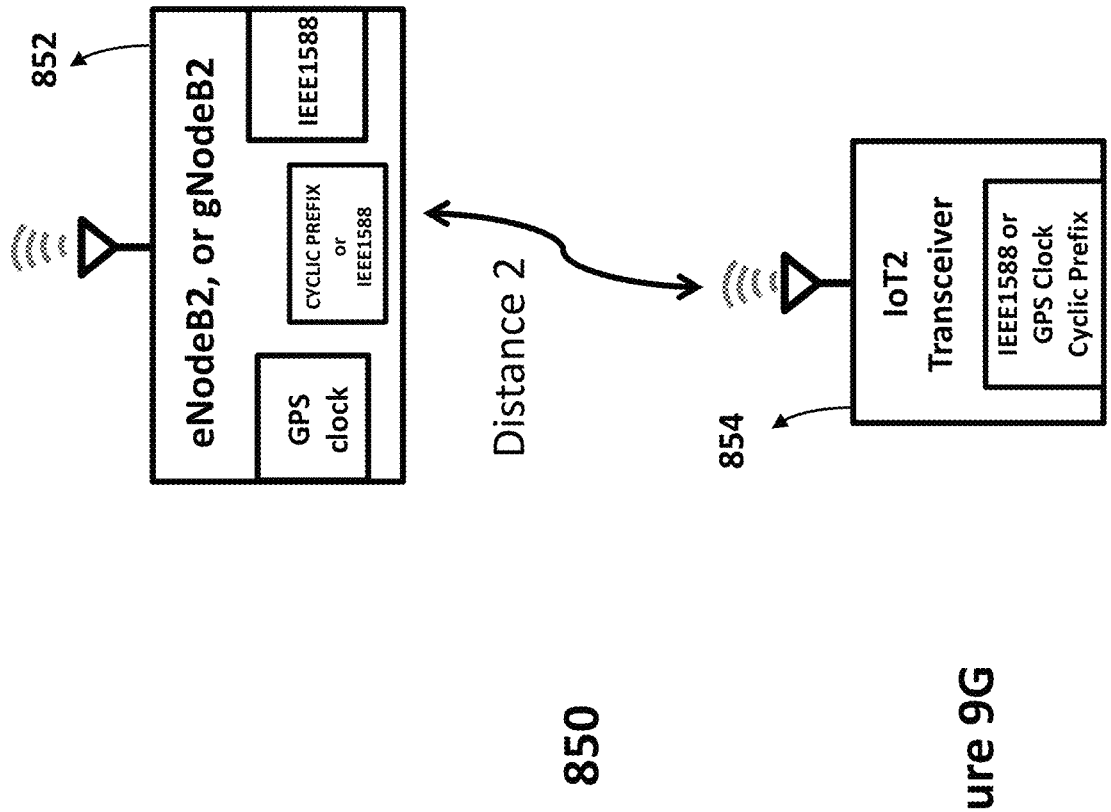
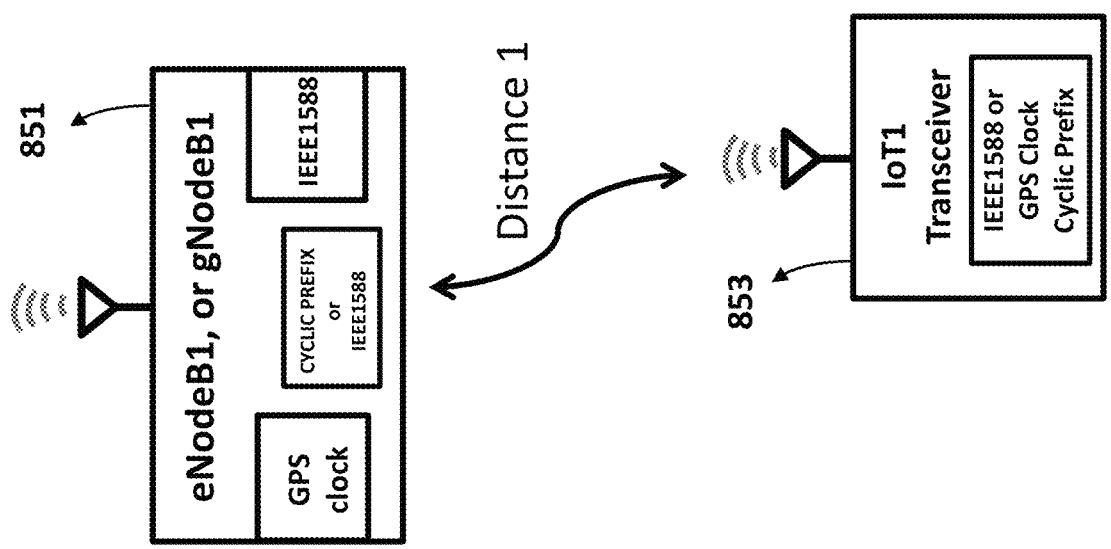
Figure 9G

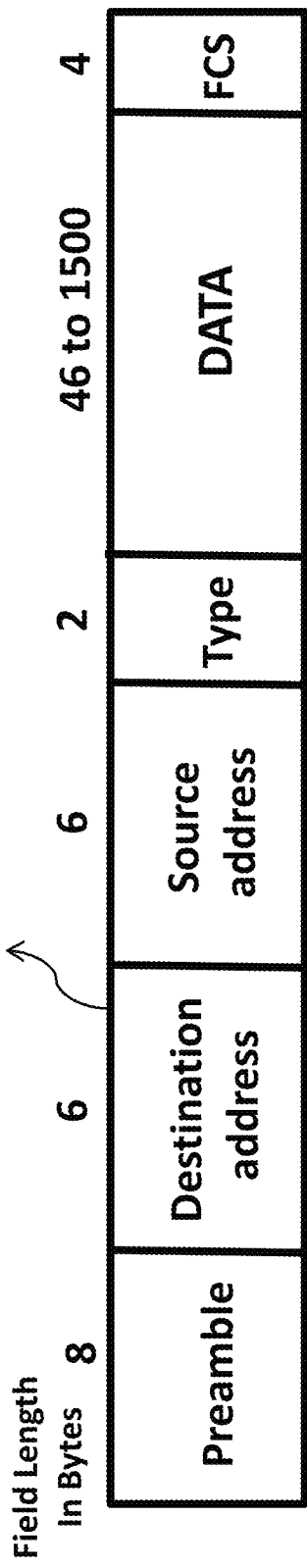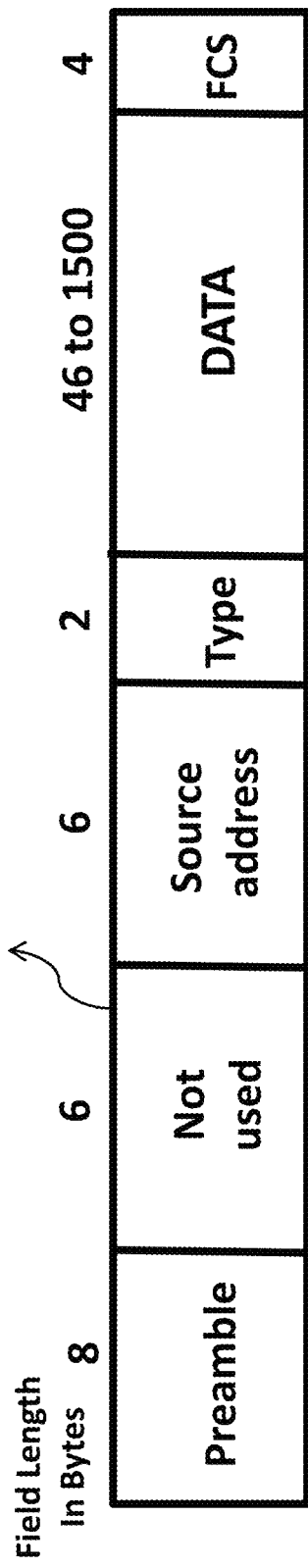
Figure 10A

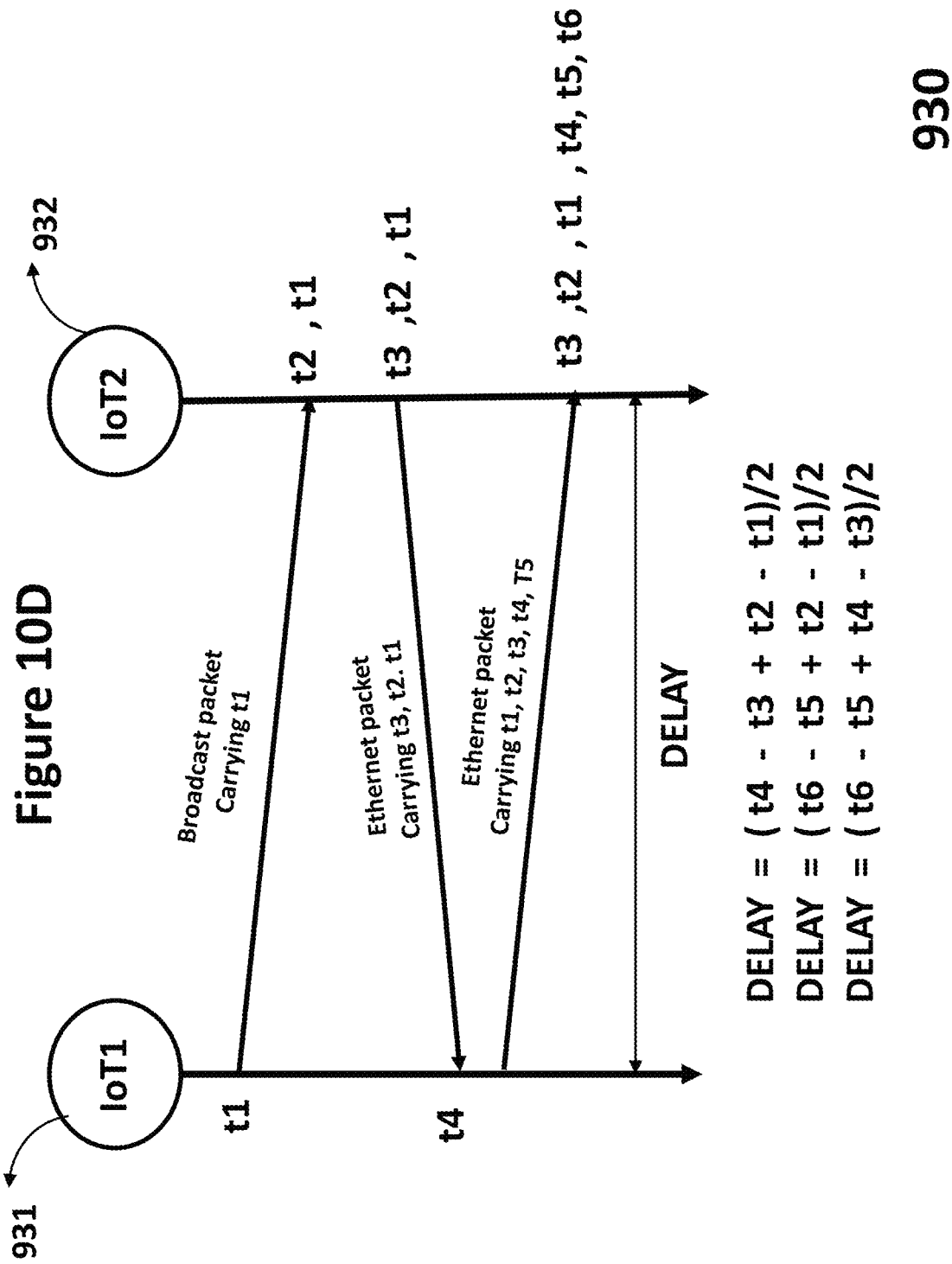

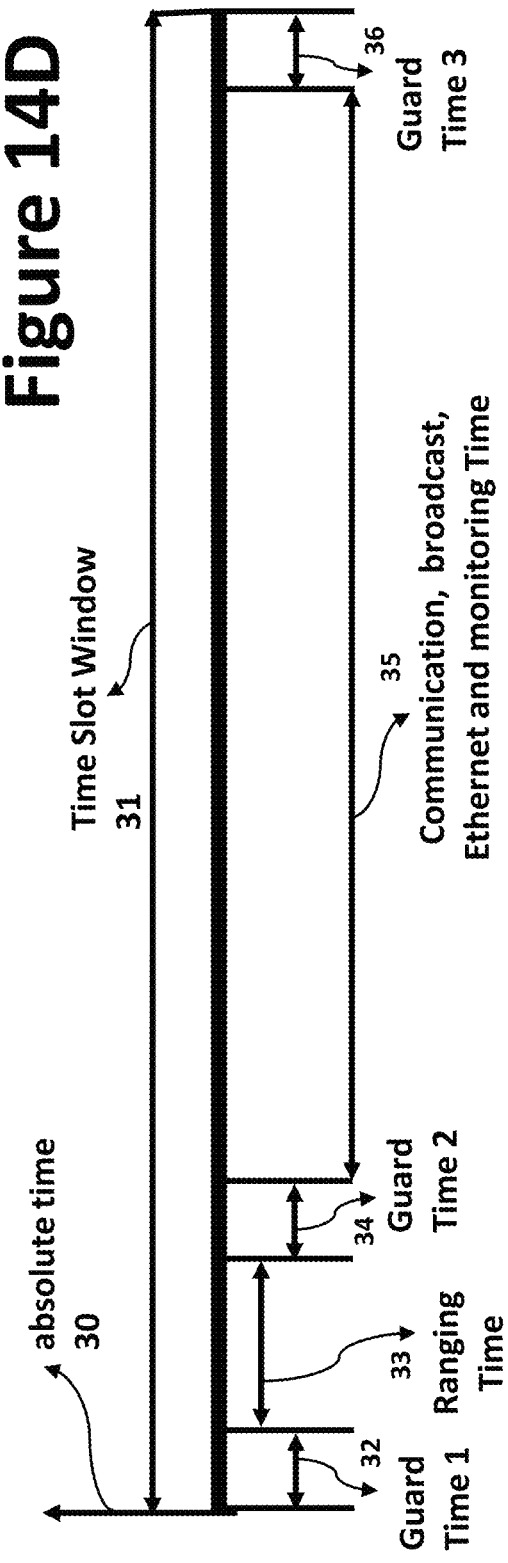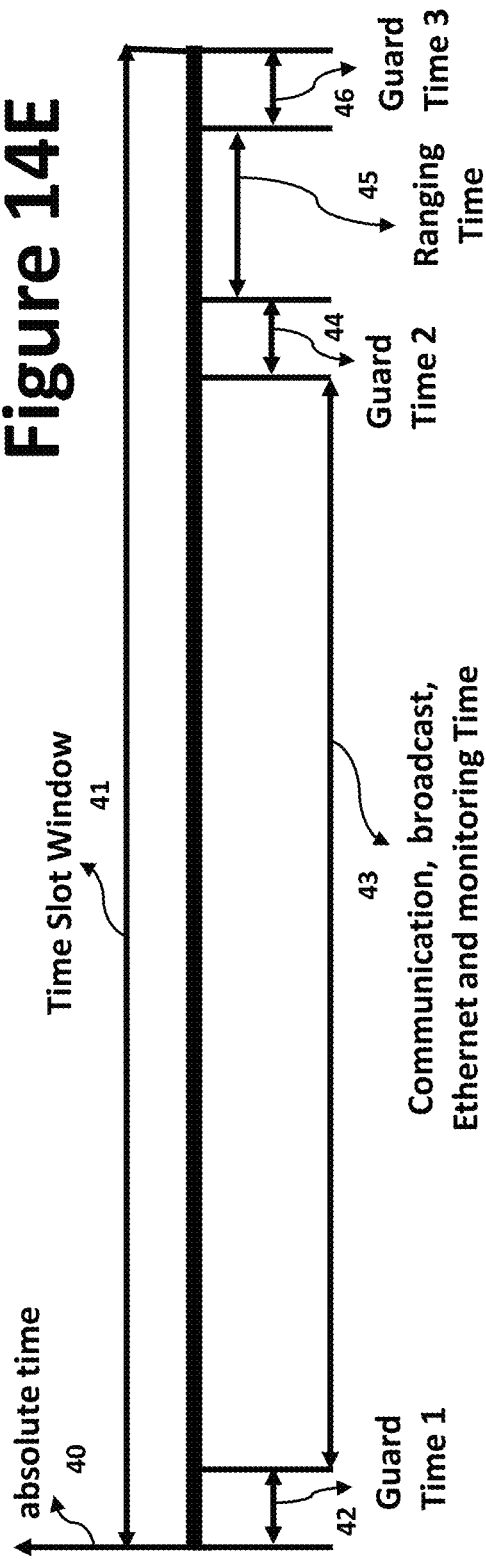

USE OF IOT NETWORK AND IOT RANGING DEVICE FOR A NAVIGATION AND PROTECTION SYSTEM

The application claims priority to the following related applications and included here are as a reference.

Application: U.S. patent application Ser. No. 17/106,137 filed Nov. 29, 2020 and entitled "USE OF 5G IOT NETWORK TO NAVIGATE AND PROTECT MOVING OBJECTS IN A SMART ENVIRONMENT".

Application: U.S. patent application Ser. No. 16/828,013 filed Mar. 24, 2020 and entitled "USE OF 5G IOT NETWORK FOR A VIRTUAL MEDICAL SYSTEM".

Application: U.S. patent application Ser. No. 16/984,995 filed Aug. 4, 2020 and entitled "USE OF 5G IOT NETWORK TO CONTROL MOVING OBJECTS IN A SMART ENVIRONMENT".

BACKGROUND

Developing intelligent systems which take into consideration the economical, environmental, and safety factors of the modern society, is one of the main challenges of this century. Progress in the fields of mobile robots, control architectures, artificial intelligence, advanced technologies, and computer vision allows us to now envisage a smart environment future.

It is safe to say that we are at the start of another industrial revolution. The rise of the connected objects known as the "Internet of Things" (IoT) will rival past technological marvels, such as the printing press, the steam engine, and electricity. From the developed world to developing world, every corner of the planet will experience profound economic resurgence. Even more remarkable is the speed with which this change will happen. A decade ago there were about one billion devices connected to internet. Today, there are close to 20 billion. In five year, it could be close to 50 billion.

The rise of IoT also means we are at the start of a new age of data. Two chief components of an "IoT object" are its ability to capture data via sensors and transmit data via the Internet. The declining cost of sensors since the start of the new millennium has been a main driver in the rise of IoT. In short, sensors are dirt cheap today. This has profound implications on the ability to capture data.

The Internet of Things (IoT) describes a worldwide network of intercommunicating devices. Internet of Things (IoT) has reached many different players and gained further recognition. Out of the potential Internet of Things application areas, Smart Cities (and regions), Smart Car and mobility, Smart Home and assisted living, Smart Industries, Public safety, Energy & environmental protection, Agriculture and Tourism as part of a future IoT Ecosystem have acquired high attention.

The Internet of Everything (IoE) is a concept that aims to look at the bigger picture in which the Internet of Things fits. Yet, when you look deeper at IoE, you'll notice it really is also about the vision of a distributed network with a growing focus on the edge in times of ongoing decentralization, some digital transformation enablers and a focus on IoT business outcomes.

While the Internet of Things today mainly is approached from the perspective of connected devices, their sensing capabilities, communication possibilities and, in the end, the device-generated data which are analyzed and leveraged to steer processes and power numerous potential IoT use cases, the Internet of Everything concept wants to offer a broader view.

The IoT based smart environments represent the next evolutionary development step in industries such as construction, manufacturing, transportation systems and even in sporting goods equipment. Like any functioning organism, the smart environment relies first and foremost on IoT sensor data from the real world. Sensory data comes from multiple sensors of different modalities in distributed locations. The smart environment needs information about all of its surroundings as well as about its internal workings.

The challenge is determining the prioritized hierarchy of: (1) detecting the relevant quantities, (2) monitoring and collecting the data, (3) assessing and evaluating the information, and (4) performing decision-making actions. The information needed by smart environments is provided by Distributed Sensor Systems, which are responsible for sensing as well as for the first stages of the processing hierarchy.

New types of applications can involve the electric vehicle and the smart house, in which appliances and services that provide notifications, security, energy-saving, automation, telecommunication, computers and entertainment are integrated into a single ecosystem with a shared user interface. Obviously, not everything will be in place straight away. Developing the technology, demonstrating, testing and deploying products, it will be much nearer to implementing smart environments by 2020. In the future computation, storage and communication services will be highly pervasive and distributed: people, smart objects, machines, platforms and the surrounding space (e.g., with wireless/wired sensors, M2M devices, etc.). The "communication language" will be based on interoperable protocols, operating in heterogeneous environments and platforms. IoT in this context is a generic term and all objects can play an active role thanks to their connection to the Internet by creating smart environments, where the role of the Internet has changed.

$5^{th}$ generation wireless systems (5G) are on the horizon and IoT is taking the center stage as devices are expected to form a major portion of this 5G network paradigm. IoT technologies such as machine to machine communication complemented with intelligent data analytics are expected to drastically change landscape of various industries. The emergence of cloud computing and its extension to fog paradigm with proliferation of intelligent 'smart' devices is expected to lead further innovation in IoT.

The existing 4G (fourth generation) networks have been widely used in the Internet of Things (IoT) and are continuously evolving to match the needs of the future Internet of Things (IoT) applications. The 5G (fifth generation) networks are expected to massive expand today's IoT that can boost cellular operations, IoT security, and network challenges and driving the Internet future to the edge. The existing IoT solutions are facing a number of challenges such as large number of connection of nodes, security, and new standards.

The drive to minimize human interaction in transportation vehicles is stronger than ever, especially in public transportation, automobiles, and etc. For instant, just a few years ago, automobiles seldom had very sophisticated safety systems. Now, it is rare to find an automobile without various safety and protection systems. And now new technology is evolving to the point of being able to offer preventive methods to better manage and dissipate sudden impact energy to the vehicle.

Today internet of things is a new revolution of the internet. A world where the real, digital and the virtual are converging to create smart environments that make energy, transport, cities and many other areas more intelligent. Different types of application like water monitoring, water pollution, air pollution, forest fire detection, smart homes, smart cities where each things can connect from anywhere to anyplace to make our life easier.

In order to understand what are the constituents of IoE we will need to dive into the core parts of IoE. IoE is an umbrella term combining the following 4 properties in one place:

1. People:

People are the humans using connected devices to deliver insights about their personal and professional self. This data can include interests, preferences, work, personal health etc. Connecting this data to enterprise needs can provide insights relating the needs and desires of prospects for businesses. Additionally, this can be used to track performance and pain points of human resources.

2. Process:

The process is the way to ensure deliverability of right data at the right time to the right person or machine. Here data is more about insightful information or an action than just random chunk. Figuring out a way to decipher the right flow of information is a key to making the best use of big data.

3. Data:

With the increase in sources and types of data, we will also need to classify the information and analyze it to bring useful insights. Data alone is nothing but once combined with analytics and analysis this new data can help businesses in decision making and managing the organization.

4. Things:

This is where we come across the term Internet of Things (IoT). Internet of things is the interconnectivity of devices that send and receive information across networks like the internet. With every signal injected into the network, data is generated which needs to be collected, summarized and analyzed efficiently.

This application discloses a time synchronous communication IoT network and IoT ranging device to monitor a smart environment. IoT ranging devices uses time of day (TOD), an absolute time, a time slot assigned to it by IoT network for ranging in the smart environment in order to avoid interference and collision.

SUMMARY

The following embodiments and aspects thereof are described and illustrated in conjunction with systems, tools and methods which are meant to be exemplary and illustrative, not limiting in scope. In various embodiments, one or more of the above-described problems have been reduced or eliminated, while other embodiments are directed to other improvements.

In one aspect, an IoT network uses distributed IoT devices which are sensor/monitoring devices to monitor its surrounding environment and detect and collect data to be processed by the IoT network or a navigation and protection system.

In another aspect, an IoT device is a flying object, a moving object, and a stationary object.

In one aspect, an IoT is a robot, equipment, and a tool.

In one aspect, the IoT device is used for a navigation and protection system (NPS).

In one aspect, the NPS is used by various moving objects, flying vehicles/objects and stationary objects in order to protect them from any collision.

In another aspect, all communication links in the IoT network are asynchronous and use Ethernet packet protocols.

In one aspect, an IoT device uses Ethernet packet protocol for over the air link between IoT network and IoT device.

In another aspect, an IoT device uses Internet Protocol (IP) packet for over the air link between IoT network and IoT device.

In one aspect, the IoT devices use IEEE1588 (institute of electrical and electronic engineering 1588) precision time protocol (PTP) to achieve clock synchronization and obtain a time of day.

In another aspect, the IoT device uses IEEE1588 PTP to obtain time of day from the IoT network (4G, 5G, 6G, and WiFi networks).

In one aspect, an IoT device uses IEEE1588 PTP to obtain time of day from another IoT device.

In another aspect, the IoT device uses GPS (Global Positioning System) receiver to obtain location coordinates and time of day.

In one aspect, the IoT device frequency and phase synchronizes to IoT network using 4G, 5G, 6G, and WiFi (wireless fidelity) air protocol.

In another aspect, the IoT (IoE) network is $5^{th}$ generation (5G), $6^{th}$ generation (6G) fix and mobile data communication network.

In one aspect, IoT network is any fix and mobile data communication network beyond 5G such as $6^{th}$ generation (6G), $7^{th}$ generation (7G) and etc.

In another aspect, IoT network is a proprietary network.

In one aspect, IoT network is WiFi (wireless fidelity) network.

In another aspect, IoT is part of a satellite network supporting one of data communication standards like 5G, 6G, 7G or a proprietary data communication standard.

In another aspect, certain data collecting applications use multiple of sensors/monitoring devices but only one of them is a master and acts as IoT device that communicates with IoT network. All sensors/monitoring devices used in the data collecting application communicate among themselves using wired and/or wireless link.

In another aspect, in cases that a data collecting application uses multiple sensors/monitoring devices (IoT devices) each individual sensor/monitoring device (IoT device) used within the data collecting application has an IP (internet protocol) address or media access control (MAC) address and uses a proprietary or any standard protocol (such as IP protocol, Ethernet protocol) to communicate with other sensors used in the data collecting application similar to an IP communication network.

In one aspect, the IoT network uses the time of day to assign the IoT device an absolute time for data collection or its operation.

In another aspect, IoT network assigns an absolute time to each IoT device that is registered with IoT network to perform its activities.

In one aspect, the absolute time assigned by IoT network to various IoT devices is constant or dynamically changed depending on the time of day or load on the IoT network.

In one aspect, the absolute time assigned to IoT devices is different and is start of a time window (time slot) assigned to an IoT device that is enough to send information data to the IoT network and other IoT devices as well as sufficient margin for any time of day error between various IoT devices.

In another aspect, IoT network shares the absolute times assigned to IoT devices with all IoT devices registered with IoT network.

In one aspect, IoT network shares all absolute times with all registered IoT devices without identifying which absolute time is assigned and which IoT device it is assigned to.

In another aspect, IoT network assigns an absolute time and a time window (time slot) for broadcasting and communication to each IoT device registered with the IoT network.

In one aspect, the time window or time slot assigned to each IoT device by IoT network is constant and identical for all registered IoT devices with IoT network, different for each IoT device, dynamically changes by IoT network, or requested by IoT device.

In one aspect, an IoT device registered with an IoT network can transmit and receive information data to and from other IoT devices without collision, and interference.

In another aspect, the IoT network uses the time of day to program the IoT devices an active time to collect data (or do other functions) and a sleep time or idle time to save power.

In one aspect, the IoT network uses the time of day to program the IoT device an absolute time to transmit collected data to (or communicate with) the IoT network or other IoT devices.

In one aspect, the absolute time is defined by the hour, the minute, the second, the millisecond, the microsecond, the nanosecond and the picoseconds.

In another aspect, the absolute time includes the hour.

In one aspect, the absolute time includes the hour and the minutes.

In one aspect, the absolute time includes the hour, the minutes, and the seconds.

In one aspect, the absolute time includes the hour, the minutes, the seconds, and the milliseconds.

In one aspect, the absolute time includes the hour, the minutes, the seconds, the milliseconds, and the microseconds.

In one aspect, the absolute time includes the hour, the minutes, the seconds, the milliseconds, the microseconds, and the nanoseconds.

In another aspect, the absolute time is only defined by minutes, by seconds, by milliseconds, by microseconds, by nanoseconds, or by picoseconds.

In another aspect, the absolute time hour is 0 to 24, minute is 0 to 60, second is 0 to 60, millisecond is 0 to 1000, microsecond in 0 to 1000, and nanosecond is 0 to 1000.

In one aspect, the absolute time is only defined by hour (0 to 24), by minutes (0 to 1440), by seconds (0 to 86400), by milliseconds (0 to 86400000) and so on.

In one aspect, the IoT network defines the date and time of day for data collection (or other functions).

In another aspect, the date is defined by the year, month, and day.

In one aspect, the IoT network or NPS specifies the date and absolute time an IoT device sends the collected data to (or communicate with) the IoT network or navigation and protection system's (NPS's) controller for processing.

In another aspect, the IoT network or NPS demands the IoT device to send its information data real time to IoT network or NPS's controller.

In one aspect, an IoT device comprises of a sensor/monitoring device and a wireless transceiver to communicate with IoT network as well as other IoT devices.

In another aspect, an IoT device is only a wireless transceiver that communicates with IoT network and obtains its data from one or more data collecting sensors that are externally attached to it.

In another aspect, a master IoT device collects data from other slave IoT devices and communicates them to the IoT network or NPS's controller.

In one aspect, the master IoT devices or slave IoT devices broadcast certain information data to other master IoT devices or slave IoT devices that are linked or belong to a specific smart environment.

In another aspect, the broadcast information data exchanged among IoT devices is used for any general or specific application.

In one aspect, the broadcast information data sent by IoT devices depends on the sensors/monitoring device used in the application.

In another aspect, the broadcast data is defined by IoT network or NPS.

In one aspect, the broadcast data is transmitted or received by an IoT device at an absolute time and during a time slot defined by IoT network.

In another aspect, the IoT devices exchange Ethernet packets.

In one aspect, IoT devices are identified by their IP addresses or media access control (MAC) address when communicating among themselves in a smart environment.

In another aspect, the IoT devices use Ethernet packet protocol to communicate among themselves.

In another aspect, the IoT devices use IP packet to communicate among themselves.

In one aspect, the IoT devices use a proprietary packet protocol to communicate among themselves.

In one aspect, the IoT devices use a WiFi protocol to communicate among themselves.

In another aspect, IoT devices support at least one of a BLUETOOTH transceiver, a ZIGBEE transceiver, a WiFI transceiver, and an Infrared transceiver.

In one aspect, the IoT devices use a 5G, 6G, 7G protocols to communicate among themselves.

In one aspect, a specific frequency band and channel is assigned to the IoT devices to communicate among each other or perform other functions.

In another aspect, the IoT device is a biometric device.

In one aspect, an IoT device is any object used in a factory.

In another aspect, an IoT device is any object used in a house.

In one aspect, an IoT device is any object used in a hospital.

In another aspect, an IoT device is any wearable device.

In one aspect, an IoT device is any object on a road, street, or highway inside and outside a city.

In another aspect, an IoT device is in general any equipment, object, tool, and device in an environment.

In one aspect, the IoT device has at least one sensor/monitoring device to collect data.

In another aspect, the type of IoT device is identified by its type indicator, model, or serial number.

In one aspect, IoT device sends a time stamp in its broadcast data that shows the time of day at the antenna port of the transmitter of the IoT device's transceiver.

In another aspect, the IoT device's transceiver at the detector of its receiver detects the time of day the time stamp of the broadcast packet from another IoT device arrives at its own transceiver antenna port.

In one aspect, an IoT device uses its wireless transceiver to broadcast its type, identity code, location, mass, the time of day, function, status (for traffic light, green, yellow, and red), specification (includes dimension), and propagation time through its transceiver's transmitter up to antenna port.

In another aspect, if IoT device is used for a traffic light the broadcast information data includes the color of traffic light and the time left for the color to change.

In one aspect, the time of day that is broadcasted by an IoT device is in form of a time stamp which can be used to calculate distance.

In another aspect, the stationary object is a lamp post, a building, a tree, a stationary vehicle/object, a traffic light post, a statue, and any other stationary object in an environment.

In one aspect, an IoT device changes its carrier frequency and modulation for better, faster transmission and reception of information.

In one aspect, two IoT devices or objects use a protocol which is based on exchange of broadcast packets and Ethernet packets to obtain the distance and approaching speed between them.

In another aspect, IoT device is a wireless sensor, Radar, a Lidar, an image sensor (camera), and an ultrasonic sensor to perform ranging to measure a distance from an object in smart environment.

BRIEF DESCRIPTION OF THE DRAWINGS

FIGS. 9A through 9G depict an OFDM transmit signal with cyclic prefix, coverage, and time of day synchronization FIGS. 10A through 10E show an Ethernet frame and a broadcast frame signal transmission FIGS. 14A through 14F illustrate embodiments of transmit signal for wireless sensor.

DESCRIPTION OF EMBODIMENTS

Reference will now be made in detail to embodiments of the present technology, examples of which are illustrated in the accompanying drawings. While the technology will be described in conjunction with various embodiment(s), it will be understood that they are not intended to limit the present technology to these embodiments. On the contrary, the present technology is intended to cover alternatives, modifications and equivalents, which may be included within the spirit and scope of the various embodiments as defined by the appended claims.

Furthermore, in the following description of embodiments, numerous specific details are set forth in order to provide a thorough understanding of the present technology. However, the present technology may be practiced without these specific details. In other instances, well known methods, procedures, components, and circuits have not been described in detail as not to unnecessarily obscure aspects of the present embodiments.

Figure 1:
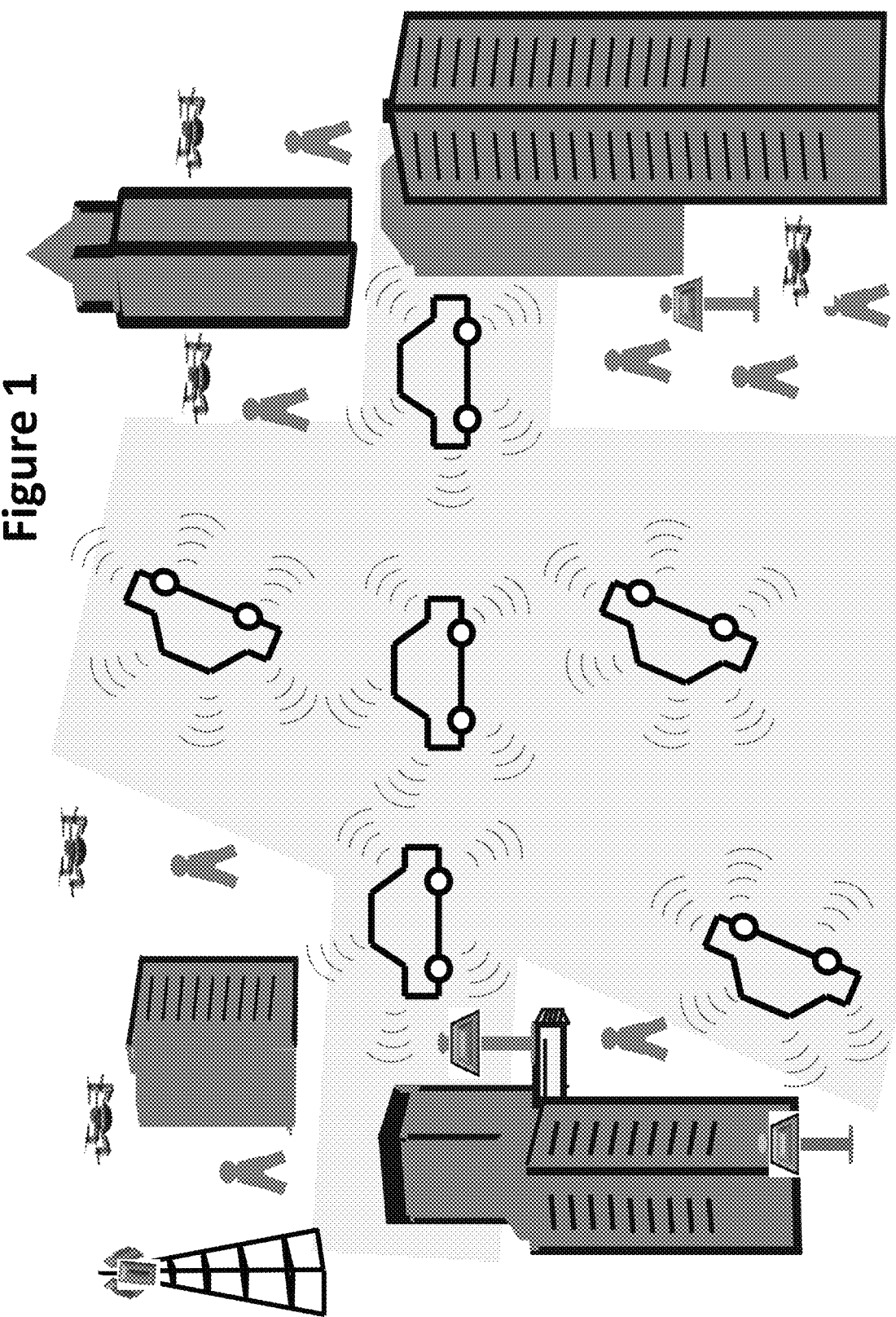
FIG. 1 illustrate a typical surrounding environment scenario for moving, flying vehicles/objects and stationary objects as IoT devices

FIG. 1 illustrates a typical environment with moving and stationary objects. The stationary objects are trees, lamp posts, small cells, buildings, street floors, walking payments, parked vehicles, statues, houses, hospitals, gas stations, schools, sport fields, shopping malls, small shops, department stores, parking lots, and any other stationary objects. Stationary objects are identified by their types, an IP addresses, shapes, masses, status (for traffic light green, yellow, or red), function, specification (includes dimension), and locations. Stationary objects act as an IoT device or IoT devices with a single IP address or independent IP addresses. Large building at different sides requires different IoT devices representing different locations and sides.

The moving vehicles are robots, humans with body armor, humans, animals, automobiles, trucks, boats, ships, bicycles, motorcycles, moving objects in a factory, moving objects in a hospital, moving objects used in buildings, and any other moving objects.

The flying vehicles are helicopters, small planes, large planes, flying humans, flying robots, gliders, flying cars, drones, missiles, birds, and any other flying objects.

Figure 2:
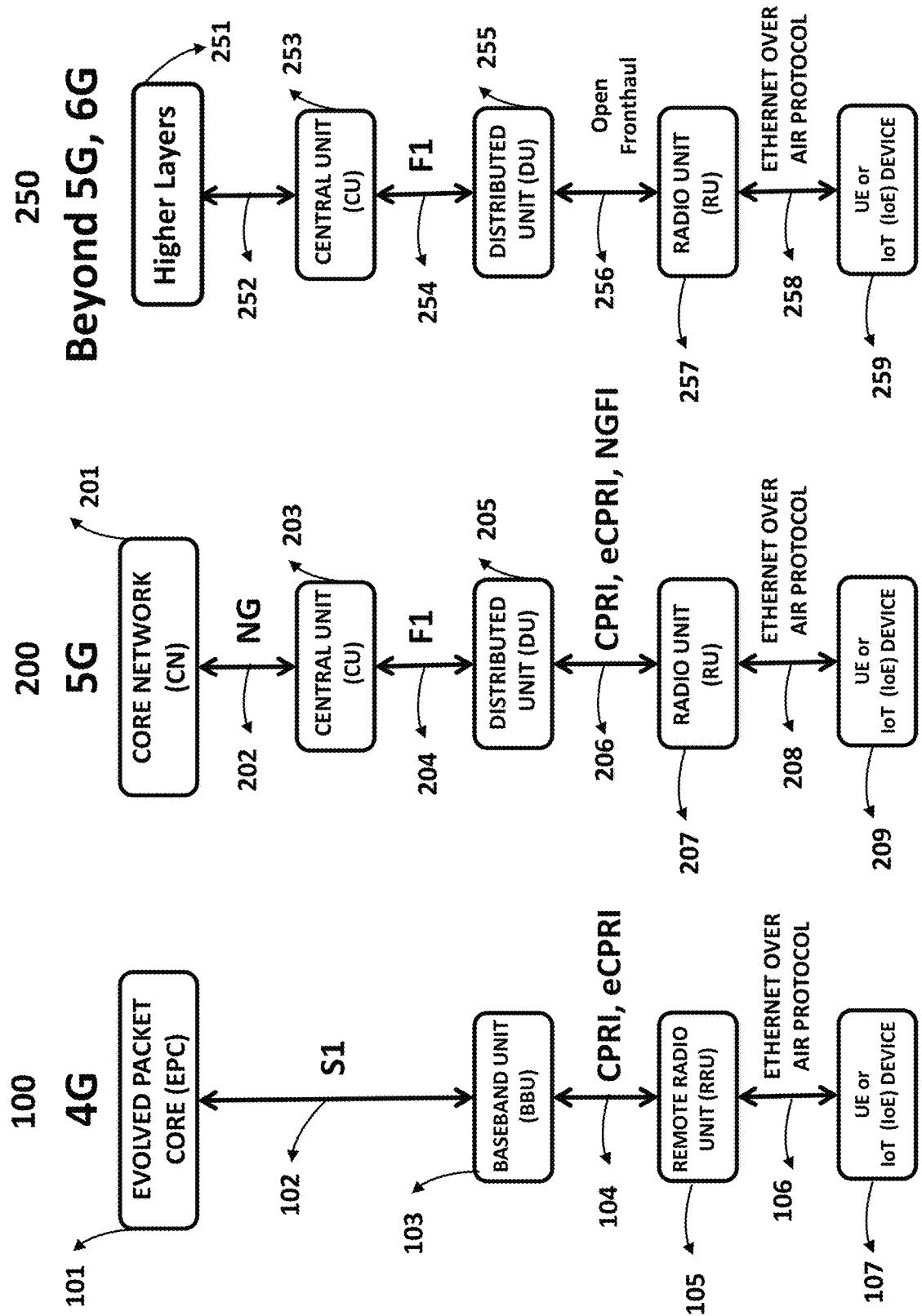
FIG. 2A illustrates 4G IoT (IoE) Network
FIG. 2B illustrates 5G IoT (IoE) Network
FIG. 2C shows beyond 5G and 6G IoT (IoE) network

FIG. 2A depicts 4G (core, eNodeB, and UE or IoT device) end to end IoT network 100 and FIG. 2B illustrates 5G (core, gNodeB, UE or IoT device) end to end IoT network 200 supporting cloud radio access network C-RAN and virtual radio access network vRAN. The 4G network 100 facilitate communication between user equipment (UE) or IoT device 107 and evolved packet core (EPC) 101 through remote radio unit (RRU) 105 and baseband unit (BBU) 103 using over the air protocol interface 106, evolved common public radio interface (eCPRI) 104 and "S1" interface 102. The RRU 105 and BBU 103 are components of evolved Node B (eNodeB) of 4G network. 5G network 200 facilitate communication between user equipment (UE) or IoT device 209 and core network (CN) 201 through radio unit (RU) 207, distributed unit (DU) 205, and central unit (CU) 203 using over the air protocol interface 208, evolved common public radio interface (eCPRI) or next generation fronthaul interface (NGFI) 206, F1 interface 204 and "NG" interface 202. The RU 207, DU 205, and CU 203 are components of 5G new radio (NR) which is also called gNodeB. Both UEs 107 and 109 also act as IoT (IoE) device.

The 4G network 100 uses different architectures depending on applications. In small cells BBU 103 and RRU 105 are collocated and there is no need for CPRI or eCPRI interface 104. A small cell connects to evolved packet core 101 through "S1" interface 102 which uses Ethernet protocol. CPRI is a synchronous protocol which is used between RRU 105 and BBU 103. The eCPRI uses Ethernet to encapsulate CPRI and is an asynchronous interface protocol between RRU 105 and BBU 103. The "S1" interface between BBU 103 and EPC 101 uses Ethernet protocol. The 5G network 200 also uses different architectures depending on applications that the network is used for. In certain architectures one or more network components are collocated. When one or more network components are collocated the components use the interfaces defined in the standard. However, there are cases such as a small cell when two or more components of network are co-located and the interfaces may be eliminated.

When Ethernet protocol is used between two ports there is a need for synchronization. There are a number of synchronization techniques that are used in data communication networks and the most common one depending on requirements of the network components or ports are syncE, PTP or IEEE1588, NTP, and GPS. The Network Time Protocol (NTP) is a networking protocol for clock synchronization between computer systems over packet-switched, variable-latency data networks. In operation since before 1985, NTP is one of the oldest Internet protocols in current use. Synchronous Ethernet, also referred to as SyncE, is an ITU-T standard for computer networking that facilitates the transference of clock signals over the Ethernet physical layer. This signal can then be made traceable to an external clock. IEEE 1588 Precision Time Protocol (PTP) is a packet-based two-way communications protocol specifically designed to precisely synchronize distributed clocks to sub-microsecond resolution, typically on an Ethernet or IP-based network. Global Satellite Positioning System (GPS) signal is received, processed by a local master clock, time server, or primary reference, and passed on to "slaves" and other devices, systems, or networks so their "local clocks" are likewise synchronized to coordinated universal time (UTC).

In both 4G (core plus eNodeB) network 100 and 5G (core plus gNodeB) network 200 when the link between two network ports is Ethernet then there is a need to synchronize the two network components using SyncE, IEEE1588 (PTP) or NTP depending on requirements and specification of two network components. "S1" interface in 4G networks, "F1" interface and "NG" interface in 5G networks use Ethernet packet protocol and IEEE1588 is widely used for synchronization between two network ports.

In case of RU 107 and RRU 105 when CPRI is used as the interface protocol clock synchronization is possible because CPRI is a synchronous protocol. When eCPRI which is an asynchronous protocol is used for RU and RRU interface to DU and BBU there is a need for one of the above mentioned synchronization techniques. If only clock synchronization is needed then syncE protocol is sufficient. However, when time of day is a requirement then IEEE1588 (PTP) or GPS needs to be used.

Mobile user equipment (UE) 107 and 109 use GPS to obtain the time of day/location and over the air protocol to achieve frequency and phase synchronization. However, for UEs or IoT devices that either can't see the GPS satellites, GPS signal is very weak, or GPS receiver increases cost, size, and power consumption another technique to acquire time of day is require. UEs and IoT devices can use their received 4G and 5G signal to achieve frequency and phase synchronization. UEs and IoT devices that do not have access to GPS signal can either obtain time of day from UEs and IoT devices in surrounding environment that have access to GPS signal and are accessible or obtain it from RUs and RRUs that they communicate with.

There are three techniques that UEs and IoT devices can use to obtain time of day from gNodeBs and eNodeBs. The precision of the time of day will be different using these three techniques. The time of day with different accuracies are used for different applications. The less accurate time of day uses one way communication between RU 207, RRU 105 and UEs or IoT devices 209, and 107 and the more accurate time of day (provided the total propagation delay within uplink of gNodeB or eNodeB and uplink of UE is equal to the total propagation delay within downlink of gNodeB or eNodeB and downlink of UE) uses two way communications between RU 207, RRU 105 and UEs or IoT devices 209, and 107. In both methods RU 207 and RRU 105 should have the time of day. In 4G network 100 and 5G network 200 for architectures that RU 207 and RRU 105 do not have the time of day or can't support exchange of time of day with UEs and IoT devices then the network component prior to RU and RRU which are DU 205 and BBU 103 can be used to propagate the time of day to UEs and IoT devices 209, and 107. The same applies to DU 205 and BBU 103. When DU and BBU do not have the time of day then CU 203 and EPC 101 can be used to propagate the time of day to UEs or IoT devices 209, and 107.

In one embodiment, 4G network 100 and 5G (6G) network 200 (250) provide the time of day to UEs and IoT devices, using institute of electrical and electronic engineering (IEEE1588) precision time protocol (PTP). IEEE1588 PTP exchange the timing messages to and from UEs or IoT devices and one component of 4G network 100 and 5G (6G) network 200 (250).

In one embodiment, IEEE1588 PTP messages are exchanged between UEs or IoT devices and one of RRU 105, BBU 103, or EPC101.

In another embodiment, IEEE1588 PTP messages are exchanged between UEs or IoT devices and one of RU 207 or 257, DU 205 or 255, or CU 203 or 253.

In one embodiment of 4G network 100, the time of day is sent to UEs and IoT devices by cyclic prefix of OFDM (orthogonal frequency division multiplexing) symbols from at least one of RRU 105, or BBU 103 depending which network component performs IFFT (inverse fast Fourier Transform).

In another embodiment of 5G network 200 or 6G (7G) network 250, the time of day is sent to UEs and IoT devices by cyclic prefix of OFDM symbols from at least one of RU 207 (257), or DU 205 (255) based on which network component performs IFFT (inverse fast Fourier Transform).

In one embodiment, 4G and 5G (or beyond 5G, 6G and 7G) networks 100, 200 and 250 utilize unused downlink sub-carriers to send the time of day to UEs or IoT devices 107, 209, and 259.

In another embodiment, 4G and 5G (or beyond 5G, 6G and 7G) networks 100, 200 and 250 utilize unused bits or messages in various downlink channels to send the time of day to UEs or IoT devices 107, 209, and 259.

In one embodiment, 5G, 6G, and 7G networks transmit Ethernet (or IP) packets over the air to UEs or IoT devices in order to have an end-to-end network using a single packet protocol. By doing this both hardware and software is significantly simplified.

In another embodiment, UEs and IoT devices obtain time of day from other UEs or IoT device in surrounding environment that are in their communication range and have time of day.

In one embodiment, UEs and IoTs devices use another frequency to communicate with other UEs and IoT devices in surrounding environment and exchange broadcast data.

In another embodiment, UEs and IoT devices communicate with other UEs and IoT devices by exchanging Ethernet (or IP) packets or any other proprietary packets.

In one embodiment, UEs and IoT devices use similar physical layer as 4G, 5G or 6G (7G) to communicate with other UEs and IoT devices in their surrounding environment without introducing any unwanted interference.

In another embodiment, UEs and IoT devices use a physical layer different from 4G, 5G, 6G (7G) to communicate with other UEs and IoT devices in their surrounding environment without introducing any unwanted interference.

In one embodiment, UEs and IoT devices communicate with WiFi network or any other proprietary network to obtain time of day and other information in their surrounding environment.

In another embodiment, a specific time is defined and communicated to UEs and IoT devices by 4G, 5G, and 6G (or 7G) networks for broadcasting or communication with other UEs or IoT devices in order to avoid interruption and interference.

In another embodiment, a specific channel is defined and communicated to UEs and IoT devices by 4G, 5G, and 6G (or 7G) networks for broadcasting or communication with other UEs or IoT devices in order to avoid interruption and interference.

In one embodiment, UEs and IoT devices support Bluetooth, Zigbee, infrared, GPS, WiFi, Laser, and any other wireless communication systems to communicate with other UEs and IoT devices in their surrounding environment and exchange information data and transmit and receive broadcast data.

In another embodiment, UEs and IoT devices transmit and receive broadcast data that includes the type of UE and IoT device, their IP address, their location, their mass, time of day, method of obtaining the time of day (IEEE1588, cyclic prefix, GPS, or other methods), their function, their status (for traffic light, green, yellow, or red), their specification (includes dimension), and propagation time through its transceiver's transmitter up to antenna port.

In one embodiment, UEs or IoT devices broadcast the time of day at their transmitter antenna port to other UEs or IoT devices in their surrounding environment.

In one embodiment, UEs and IoT devices support WiFi, Bluetooth, Infrared, laser, and Zigbee over the air wireless protocols.

Cloud radio access network or C-RAN architectures shown in FIGS. 2A and 2B enables cost saving on expensive baseband resources, in which the baseband units are shared in a centralized baseband pool. Therefore, the computing resources can be utilized optimally based on the demand. C-RAN architecture has also opened up an opportunity for RAN virtualization (vRAN) in order to further reduce cost. Therefore, virtual RAN or vRAN has been developed to simplify the deployment and management of the RAN nodes and make the platform readily available for multitude of dynamically changing service requirements. The main issue with C-RAN and vRAN is that these architectures still utilize propriety software, hardware and interfaces which lack openness as a major bottleneck in efficiently utilizing virtualization. In order to overcome the limitations of C-RAN and vRAN, O-RAN is emerging as a new RAN architecture that uses open interfaces between the elements implemented on general-purpose hardware. This allows operators select RRU or RU and BBU or DU hardware and software from different vendors. In addition, open interfaces between decoupled RAN components provide efficient multi-vendor interoperability. O-RAN architecture also allows enhanced RAN virtualization that supports more efficient splits over the protocol stack for network slicing purpose. O-RAN further reduces RAN expenditure by utilizing self-organizing networks that reduce conventional labor intensive means of network deployment, operation and optimization. In addition to cost reduction, intelligent RAN can handle the growing network complexity and improve the efficiency and accuracy by reducing the human-machine interaction.

FIG. 2C shows the O-RAN end to end architecture (UE, gNodeB, and core) 250 for beyond 5G and 6G. Higher layers 251 communicate with open interface 252 to central unit 253. The interface between central unit (CU) 253 and distributed unit (DU) 255 is open interface 254 "F1" and the interface between distributed unit 255 and radio unit (RU) 257 is open fronthaul 256. UE or IoT device 259 use over the air interface 258 to communicate with RU 257. Therefore, the only difference between 5G, beyond 5G and 6G ORAN architecture is open interface 252, open "F1" interface 254 and open fronthaul 256.

All embodiments related to 5G explain above apply to beyond 5G and 6G (7G) ORAN.

Figure 3:
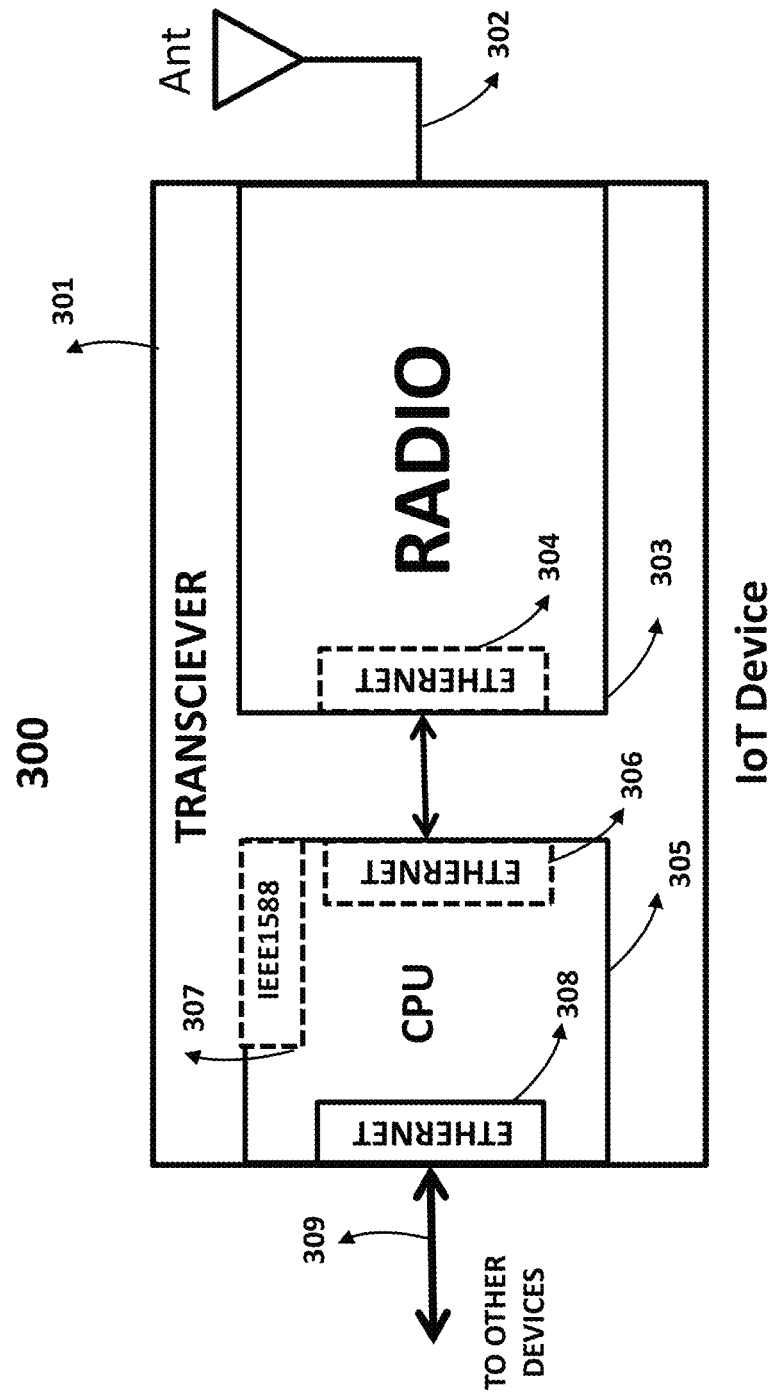
FIG. 3 illustrates a typical IoT device that can be found in an environment communicating with cellular network

FIG. 3 illustrate the architecture of an IoT device 300. In general IoT device 300 communicates with 4G, 5G and 6G (or 7G) networks to exchange information data. IoT device 300 through radio 303 attaches itself to a 4G, 5G, or 6G (7G) network in its surrounding environment and listens to commands to perform certain functions. Radio 303 when receives a command sends it to CPU 305 to be evaluated and performed by CPU 305 or uses other devices that are connected to CPU 305 to perform the command or commands. Then the results obtained from performing the commands through CPU 305 and radio 303 is transmitted to 4G, 5G, or 6G (7G) network for analysis.

In one embodiment, IoT device 300 includes among other things transceiver 301 which consists of antenna 302, radio 303, possible radio Ethernet port 304, CPU 305, possible Ethernet port 306 towards radio, possible IEEE1588 PTP 307, and Ethernet port 308 towards other devices.

In one embodiment, IoT device 300 through antenna 302 and radio 303 attaches to 4G, 5G, or 6G (7G) IoT network and if needed obtains the time of day.

In another embodiment, IoT device transceiver 301 obtains the time of day through IEEE1588 PTP, downlink transmit cyclic prefix, downlink transmit unused sub-carriers, or unused bits or messages in one of downlink channels from 4G, 5G, or 6G (7G) IoT network.

In one embodiment, IoT device 300 communicates via its transceiver's CPU 305 with another device using an Ethernet port 308.

In another embodiment, IoT device 300 propagates the time of day to an external device or equipment via its transceiver's Ethernet port 308 and link 309 using IEEE1588 PTP 307.

In one embodiment, IoT device 300 receives commands or information data from 4G, 5G, or 6G (7G) IoT network and communicates the commands to an external device through its transceiver's Ethernet port 308.

In one embodiment, IoT device 300 receives information data from an external device through its Ethernet port 308 and transmits it to 4G, 5G, or 6G (7G) IoT network using its transceiver's radio 303 and antenna 302.

In another embodiment, IoT device 300 communicates to an external device via its transceiver's CPU 305 using a serial interfaces or a parallel interface instead of Ethernet interface 308.

In one embodiment, IoT device 300 communicates with other IoT devices and exchange broadcast data. The IoT device 300 uses a different frequency or channel to communicate with another IoT device in order to avoid interruption and interference.

In another embodiment, IoT device 300 communicates with other IoT devices in its surrounding environment that are in its communication range using a proprietary physical layer or a physical layer similar to 4G, 5G, or 6G (7G) network.

In one embodiment, IoT device 300 exchanges Ethernet packets or any other proprietary packets with other IoT devices in its surrounding environment.

In another embodiment, IoT device 300 communicates with a WiFi network in its surrounding environment.

In one embodiment, IoT device 300 through its transceiver 301 supports WiFi, Bluetooth, Zigbee, laser, and Infrared over the air wireless protocols.

In one embodiment, IoT device exchange IEEE1588 PTP messages with another IoT device or a WiFi router in surrounding environment to obtain or propagate the time of day.

In another embodiment of IoT device 300, the device that is connected to transceiver 301 through link 309 is any device or object that is remotely controlled to perform certain function.

Figure 4:
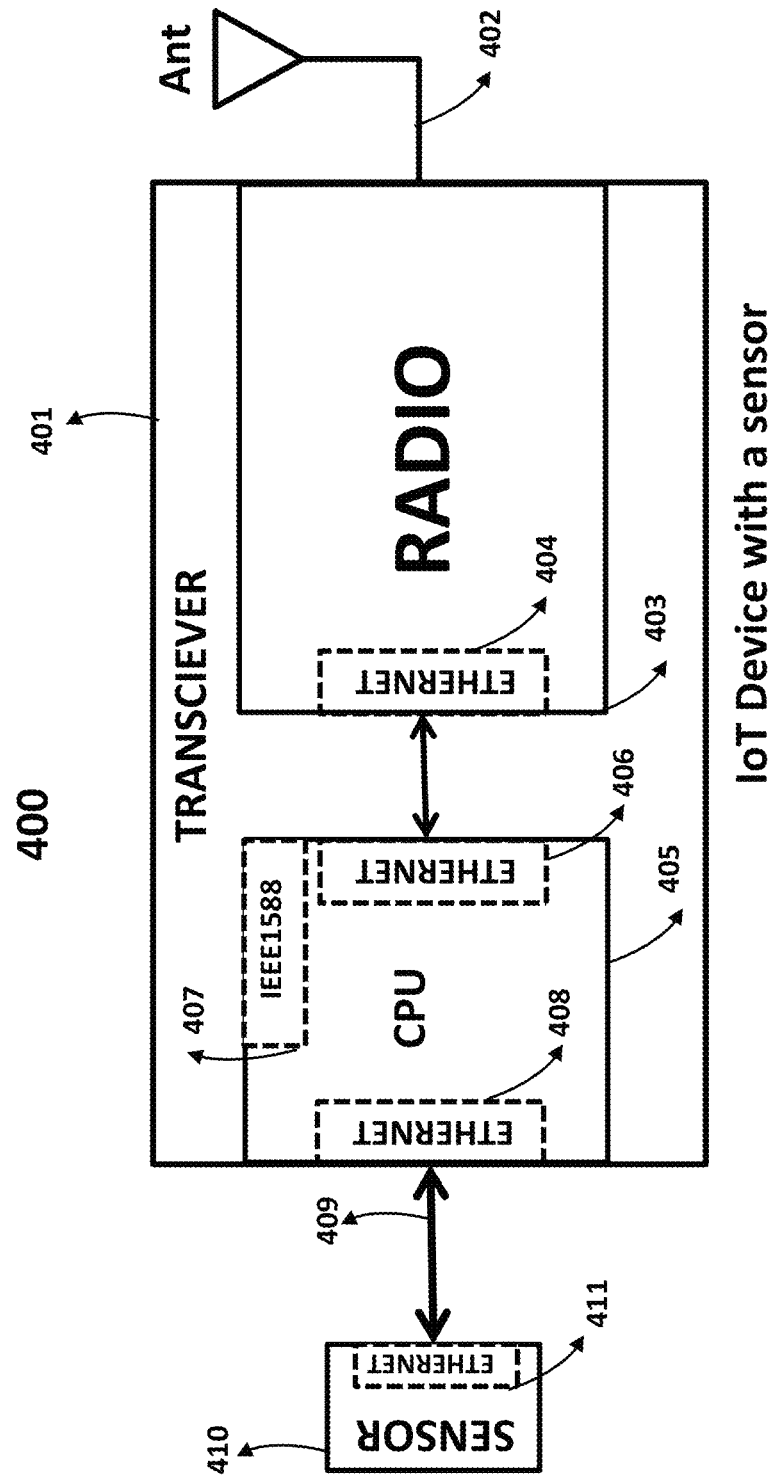
FIG. 4 illustrates a typical IoT device that can be found in an environment communicating with cellular network with a single sensor

FIG. 4 shows the architecture of an IoT sensor device 400. In general IoT sensor device 400 communicates with 4G, 5G, and 6G (7G) networks to exchange information data. IoT sensor device 400 through radio 403 attaches itself to a 4G, 5G, or 6G (7G) network in its surrounding environment and listens to commands to activate sensor 410. Radio 403 when receives a command, sends it to CPU 405 to be evaluated and performed by CPU 405 or sensor 410 that is connected to CPU 405. Then the results obtained from performing the commands through CPU 405 and radio 403 is transmitted to 4G, 5G, or 6G (7G) network for analysis.

In one embodiment, IoT sensor device 400 includes, among other things transceiver 401 which consists of antenna 402, radio 403, possible radio Ethernet port 404, CPU 405, possible Ethernet port 406 towards radio, possible IEEE1588 PTP 407, possible Ethernet port 408 and sensor 410 with possible Ethernet port 411.

In one embodiment, IoT sensor device 400 uses an attached sensor 410 to perform ranging (Lidar, Radar, Image sensor, ultrasonic sensor, laser, and wireless sensor).

In another embodiment, IoT sensor device 400 uses an external device which is a sensor 410.

In one embodiment, IoT sensor device 400 uses an external sensor 410 that communicates with transceiver 401 using Ethernet packet protocol through Ethernet ports 411 and 408.

In another embodiment, the link 409 between Ethernet port 408 of transceiver 401 and Ethernet port 411 of sensor 410 is a wired link or a wireless link.

In another embodiment of IoT sensor device 400, the wired 409 link is a standard serial interface, a proprietary serial interface, or a parallel interface.

In one embodiment of IoT sensor device 400, the wireless link 409 between transceiver 401 and sensor 410 is at least one of Bluetooth, Zigbee, WiFi, Infrared, laser, or any proprietary wireless link.

In another embodiment of IoT sensor device 400, the sensor 410 does not necessarily sense anything. Sensor 410 is a tool, equipment, a robot hand, an on/off switch, any activation or deactivation device, and any device, equipment or object that is remotely controlled to perform certain function.

Figure 5:
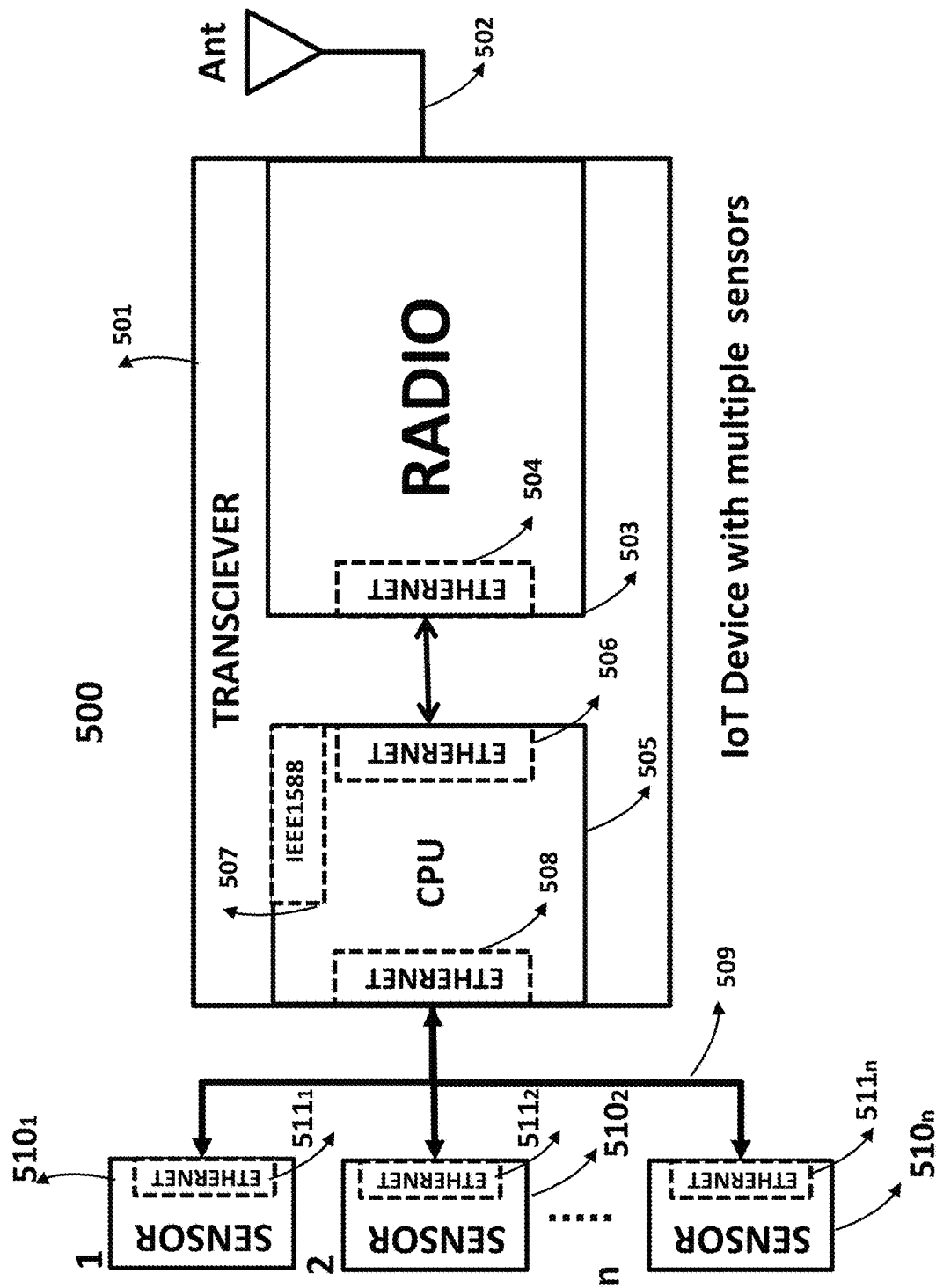
FIG. 5 depicts a typical IoT device that can be found in an environment communicating with cellular network with multiple sensors

FIG. 5 shows the architecture of an IoT sensor network 500. In general IoT sensor network 500 communicates with 4G, 5G, and 6G (7G) networks to exchange information data. IoT sensor network 500 through radio 503 attaches itself to a 4G, 5G, or 6G (7G) network in its surrounding environment that supports Internet of Things and listens to commands to activate sensor network $510_1$ to $510_n$. Radio 503 when receives a command, sends it to CPU 505 to be evaluated and performed by CPU 505 or sensor network $510_1$ to $510_n$ that is connected to CPU 505. Then the results obtained from performing the commands through CPU 505 and radio 503 is transmitted to 4G, 5G, or 6G (7G) network for analysis.

In one embodiment, IoT sensor network 500 includes among other things transceiver 501 which consists of antenna 502, radio 503, possible radio Ethernet port 504, CPU 505, possible Ethernet port 506 towards radio, possible IEEE1588 PTP 507, possible Ethernet port 508 and sensor network $510_1$ to $510_n$.

In another embodiment, IoT sensor network 500 uses an external monitoring sensor network $510_1$ to $510_n$ that can perform various functions autonomously or through commands that sent to it remotely.

In one embodiment, IoT sensor network 500 uses an external sensor network $510_1$ to $510_n$ that communicates with transceiver 501 through Ethernet ports $511_1$ to $511_n$.

In another embodiment, the sensor network $510_1$ to $510_n$ can be a monitoring network $510_1$ to $510_n$ or a mix of sensors, monitoring devices, autonomous devices, IoT devices and remotely controlled devices or equipments $510_1$ to $510_n$.

In one embodiment, each device within network of devices $510_1$ to $510_n$ has an IP (internet protocol) address that identifies the device.

In another embodiment, each device within network of devices $510_1$ to $510_n$ uses its serial number for its identity.

In one embodiment of IoT sensor network 500, at least one of an Ethernet packet and a proprietary packet is used for communication between transceiver 501 and devices/equipment $510_1$ to $510_n$.

In another embodiment, the link 509 between Ethernet port 508 or port 508 of transceiver 501 and Ethernet ports $511_1$ to $511_n$ or ports $511_1$ to $511_n$ of devices $510_1$ to $510_n$ is a wired link, a wireless link or a mix of wired and wireless.

In another embodiment of IoT sensor network 500, the wired link 509 is a standard serial interface, a proprietary serial interface, or a parallel interface.

In one embodiment of IoT sensor network 500, the wireless link 509 between transceiver 501 and devices $510_1$ to $510_n$ is at least one of Bluetooth, Zigbee, WiFi, Infrared, laser, or any proprietary wireless link.

In one embodiment, IoT sensor network 500 receives an absolute time and a time slot from 4G, 5G, 6G (or 7G), or WiFi network for its various activities as well as scheduling activities of the external devices connected to IoT sensor network 500.

In one embodiment of the IoT sensor network 500, the sensor network 510₁ to 510ₙ is slave IoT network 510₁ to 510ₙ.

Figure 6:
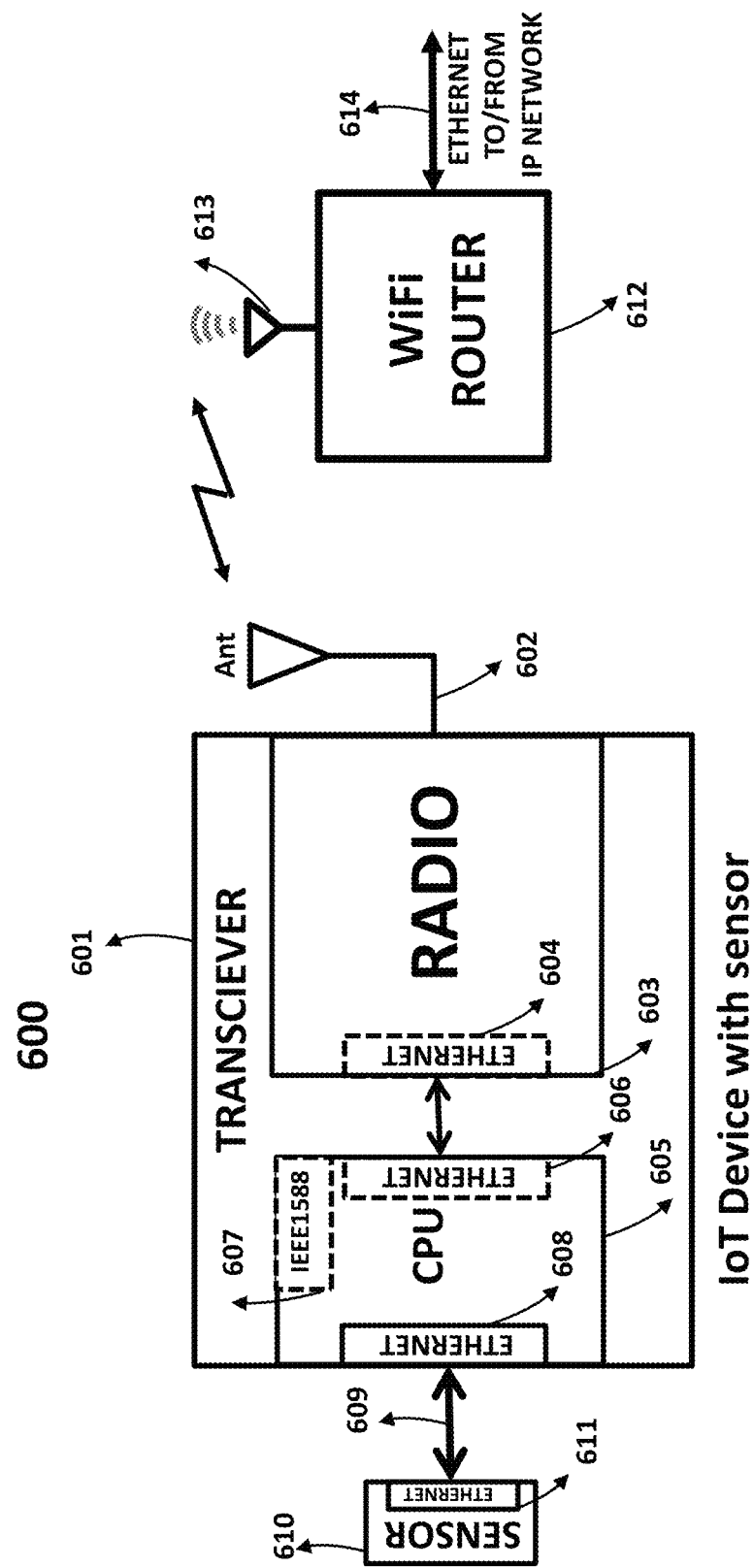
FIG. 6 illustrates a typical IoT device communicating with WiFi network

FIG. 6 illustrate a WiFi based IoT device 600. In general IoT device 600 communicates with WiFi (wireless fidelity) router 612 to exchange information data. IoT device 600 through radio 603 attaches itself to a WiFi router 612 in its surrounding environment that supports Internet of Things and listens to commands to activate sensor 610. Radio 603 when receives a command sends it to CPU 605 to be evaluated and performed by CPU 605 or sensor 610 (or any other device instead of sensor 610) that is connected to CPU 605. Then the results obtained from performing the commands through CPU 605 and radio 603 is transmitted to WiFi network for analysis.

In one embodiment, IoT device 600 uses IEEE1588 PTP to obtain time of day from WiFi router 612.

In another embodiment, IoT device 600 uses downlink transmit OFDM cyclic prefix, downlink transmit OFDM unused sub-carriers, or unused bits or messages in a downlink WiFi frame to obtain time of day.

In one embodiment, IoT device 600 receives an absolute time from WiFi router 612 for its various activities as well as scheduling the external devices connected to IoT device 600 for their activities.

Figure 7:
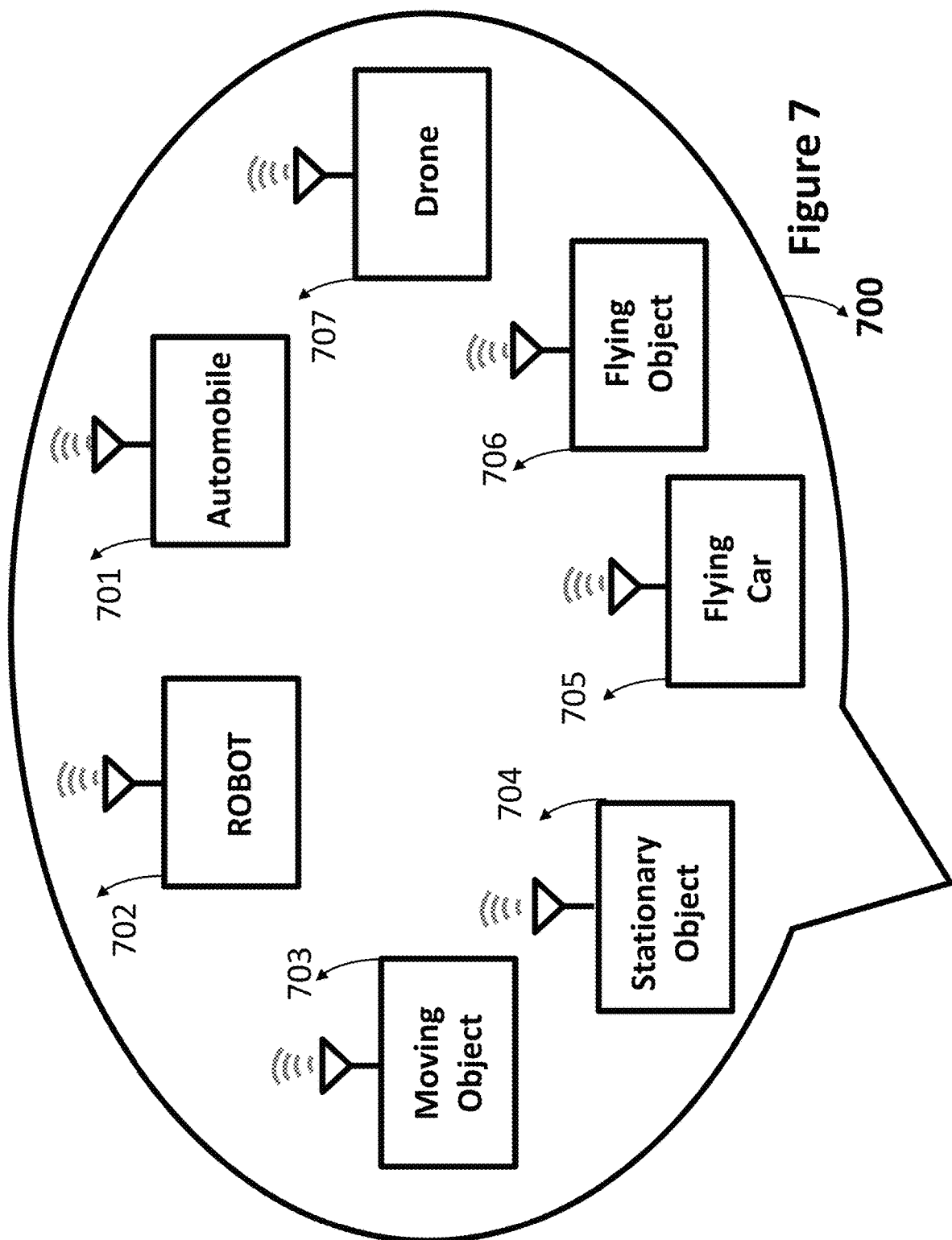
FIG. 7 shows moving vehicles, flying vehicles/objects, and stationary objects that act as an IoT in an environment

FIG. 7 depicts a smart environment 700. In general in the smart environment 700 in addition to open space various stationary, moving and flying object exist. In the smart environment or area 700 all the objects coexist and operate synchronously and freely without any interruption, interference, and collision.

Smart environment 700 includes, among other things, automobile 701, robots 702, moving objects 703, stationary objects 704, flying car 705, flying object 706, and drone 707.

In one embodiment, moving object 703 is human with body amour, bicycle, motorbike, boat and etc.

In one embodiment, stationary object 704 is a tree, a lamp post, a small cell, a building, a statue and etc.

In another embodiment of smart environment 700, flying object 706 is a helicopter, a small plane, a flying human, a flying robot, a glider, and etc.

In one embodiment of smart environment 700, automobile 701, robot 702, moving object 703, stationary object 704, flying car 705, flying object 706, and drone 707 act as IoT devices and broadcast wirelessly certain data specific to automobile, robot, moving object, stationary object, flying car, flying object, and drone.

In another embodiment of smart environment 700, the broadcast data includes a time stamp indicating time of day, method of obtaining the time of day (IEEE1588, cyclic prefix, GPS, or others), type of the object, location coordinates obtained from GPS (global positioning system) receiver, function of the object, status of the object (for traffic light, green, yellow, or red), specification (includes dimension) of the object, an identity number, signal propagation time through transmitter of the IoT device's transceiver up to the input of transmit antenna, and an estimated mass.

In one embodiment, when the stationary object is a traffic light the broadcast data includes the color of traffic light, time left to change the color, color of light for turning left or light, and moving straight.

In one embodiment, when the object is a bridge or a tunnel the broadcast data includes specification (dimensions) of the bridge or tunnel.

In one embodiment, the identity number of an object (IoT device) is its serial number.

In one embodiment, the identity number of an object (IoT device) is an IP (Internet Protocol) address.

In one embodiment, the identity number of an object (IoT device) is a MAC (media access control) address.

In another embodiment of smart environment 700, each object (IoT device) in the environment receives the broadcast data from other objects (IoT devices) and is fully aware of its surrounding environment.

In one embodiment of smart environment 700, each object (IoT device) in the environment uses a protocol that is known to all objects (IoT devices) for broadcasting its data.

In one embodiment of smart environment 700, the broadcast protocol is defined by a standard body like IEEE (Institute of electrical and electronic engineering), ITU (International Telecommunication Union), or cellular network (5G and beyond).

Figure 8:
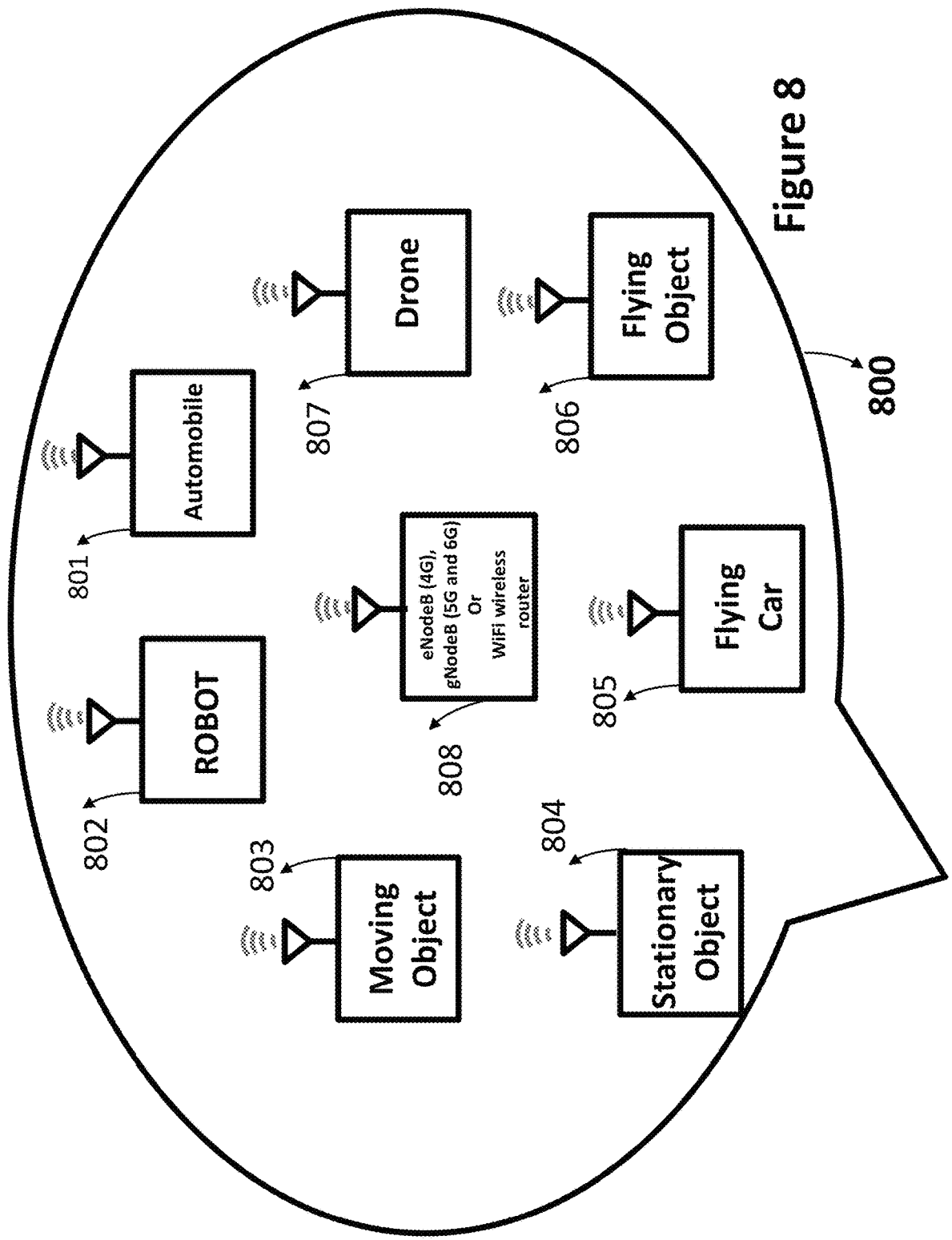
FIG. 8 illustrates moving vehicles, flying vehicles/objects, and stationary objects in an environment communicating with 4G, 5G and 6G Remote Radio Unit (RRU) and Radio Unit (RU) respectively

FIG. 8 depicts a smart environment 800 with objects (IoT devices) that communicate with a public or private network. In general, the smart environment 800 in addition to open space consists of various stationary, moving and flying objects (IoT devices) that are capable of wirelessly communicate with other objects (IoT devices) as well as a public or private communication network. In the smart environment 800 all the objects (IoT devices) coexist synchronously in time (time of day) and operate freely without any interruption, interference, and collision. All the objects (IoT devices) in smart environment 800 are registered with 4G, 5G, or 6G (7G) networks through their eNodeB or gNodeB base station 808. 4G, 5G or 6G (7G) networks broadcasts certain information data to all objects (IoT devices) in smart environment 800 that are registered with 4G, 5G, or 6G (7G) networks through their eNodeB or gNodeB. The broadcast information data is updated when an object (IoT device) exit (deregister with eNodeB or gNodeB of 4G, 5G, 6G, or 7G network) or enter (register with eNodeB or gNodeB of 4G, 5G, 6G, 7G network) the smart environment 800. The base station 808 can also be a wireless router of a WiFi network and all objects (IoT devices) in smart environment 800 register with WiFi network through wireless router 808 and receive broadcast information data from WiFi network.

In one embodiment smart environment 800 includes, among other things, automobile 801, robot 802, moving object 803, stationary object 804, flying car 805, flying object 806, drone 807, and a wireless base station 808 that supports a public (eNodeB, or gNodeB of 4G, 5G, or 6G network and wireless router of a WIFi network) or private communication network.

In one embodiment, the wireless base station 808 is a cellular (4G or 5G, beyond 5G and 6G) small cell, macro-cell, micro-cell or picocell.

In another embodiment, the wireless base station 808 is a WiFi wireless router that is connected to the IP network as well as cellular network (4G, 5G, beyond 5G and 6G).

In one embodiment, the wireless base station 808 is part of a private network that is connected to IP network as well as cellular network (4G, 5G and beyond 5G and 6G).

In one embodiment, wireless base station 808 is a 4G RRU, a 5G RU or a 6G RU.

In another embodiment, the wireless base station (4G, 5G, 6G, or 7G) communicates with the stationary, moving and flying objects in the smart environment 800 and obtains type, function, status (for traffic light, green, yellow, or red), specification (includes dimension), location (obtained from GPS receiver), identity number, signal propagation time through transmitter of the IoT device's wireless transceiver up to the input of transmit antenna, and estimated mass from objects 801, 802, 803, 804, 805, 806 and 807.

In one embodiment, wireless base station (4G, 5G, 6G, or 7G) 808 in the smart environment 800 broadcast the information obtained from each object 801, 802, 803, 804, 805, 806 and 807 to all objects (IoT devices) in smart environment 800.

In one embodiment, all moving and stationary objects 801, 802, 803, 804, 805, 806 and 807 continuously update the data they obtain from wireless base station 808 related to other objects in their surrounding smart environment 800.

In another embodiment, the identity number of each object in the smart environment 800 is the object's serial number, a MAC address or an IP address that is an IP4 or IP6.

In one embodiment, the wireless base station 808 uses GPS to obtain clock synchronization and time of day.

In another embodiment, all objects (IoT devices) in the smart environment 800 receive time of day and their location coordinates from GPS receiver.

In another embodiment, a stationary object (IoT device) in the smart environment has its location coordinates manually program to it or obtains from base station 808.

In one embodiment, the wireless base station (4G, 5G, 6G, or 7G) 808 in smart environment 800 supports IEEE1588 (Institute of electrical and electronic engineering synchronization standard 1588) PTP which provides clock synchronization and time of day for wireless base station 808 through any port in data communication network as well as 4G, 5G, 6G, 7G network.

In another embodiment, all moving and stationary objects (IoT devices) 801, 802, 803, 804, 805, 806 and 807 also supports IEEE1588 in order to obtain time of day.

In one embodiment, wireless base station (4G, 5G, 6G, 7G, or WiFi) 808 broadcasts to each moving and stationary objects (IoT devices) 801, 802, 803, 804, 805, 806 and 807 an absolute time and time slot when they can broadcast their information or communicate with other IoT devices.

In one embodiment, wireless base station (4G, 5G, 6G, 7G, or WiFi) 808 broadcasts to each moving and stationary objects (IoT devices) 801, 802, 803, 804, 805, 806 and 807 the absolute time and the time slot when they can transmit and receive.

In one embodiment, the absolute times and time slots assigned by IoT network (4G, 5G, 6G, 7G, or WiFi) to various IoT devices is constant or dynamically changes depending on the time of day or load on the IoT network.

In another embodiment, IoT network (4G, 5G, 6G, 7G, or WiFi) assigns an absolute time and a time slot for broadcasting and communication to each IoT device registered with the IoT network.

In one embodiment, the time window (slot) assigned to each IoT device by IoT network (4G, 5G, 6G, 7G, or WiFi) is constant and identical for all registered IoT devices with the IoT network, different for each IoT device, dynamically changes by the IoT network, or requested by IoT device.

In one embodiment, wireless base station (4G, 5G, 6G, 7G, or WiFi) 808 broadcasts to each moving and stationary objects (IoT devices) 801, 802, 803, 804, 805, 806 and 807 the absolute time and time slot when their sensors can collect data.

In one embodiment, wireless base station (4G, 5G, 6G, 7G, or WiFi) 808 broadcasts to each moving and stationary objects (IoT devices) 801, 802, 803, 804, 805, 806 and 807 the absolute time and time slot when their wireless sensors can perform ranging to measure a distance and an approaching speed of various objects in their surrounding smart environment.

In one embodiment, wireless base station (4G, 5G, 6G, 7G, or WiFi) 808 broadcasts to each moving and stationary objects (IoT devices) 801, 802, 803, 804, 805, 806 and 807 the carrier frequency and modulation for their wireless sensor.

In one embodiment, wireless base station (4G, 5G, 6G, 7G, or WiFi) 808 broadcasts to each moving and stationary objects (IoT devices) 801, 802, 803, 804, 805, 806 and 807 the carrier frequency, channel, modulation, data rate, range of output power, and over the air protocol (type of transceiver which is one of 4G, 5G, 6G, 7G, WiFi, Bluetooth, Zigbee, laser, or infrared) for ranging as well as broadcasting and communicating to other IoT devices.

In one embodiment, each moving and stationary objects (IoT devices) 801, 802, 803, 804, 805, 806 and 807 exchange Ethernet packets with wireless base station 808.

In one embodiment, each moving and stationary objects (IoT devices) 801, 802, 803, 804, 805, 806 and 807 exchange Ethernet packets among each other based on the absolute time and time slot assigned to them by the base station 808.

In one embodiment, the link between each moving and stationary objects (IoT devices) 801, 802, 803, 804, 805, 806 and 807 and wireless base station (4G, 5G, 6G, 7G, or WiFi) 808 is an over the air Ethernet link.

In one embodiment, communication link between each moving and stationary objects (IoT devices) 801, 802, 803, 804, 805, 806 and 807 and the cloud network, data network, and core network through wireless base station (4G, 5G, 6G, 7G, or WiFi) 808 supports a single end-to-end Ethernet packet protocol.

In another embodiment, moving and stationary objects (IoT devices) 801, 802, 803, 804, 805, 806 and 807 use their wireless sensor to broadcast their broadcast data.

In one embodiment, moving and stationary objects (IoT devices) 801, 802, 803, 804, 805, 806 and 807 use their wireless transceiver that communicates with 4G, 5G or 6G (7G) network to broadcast their broadcast data or sent their Ethernet frame or packet.

In one embodiment, moving and stationary objects (IoT devices) 801, 802, 803, 804, 805, 806 and 807 support WiFi, Bluetooth, Zigbee, Infrared, laser and proprietary wireless transceivers and use them to broadcast their broadcast data or transmit and receive Ethernet packets or frames.

Figure 9A:
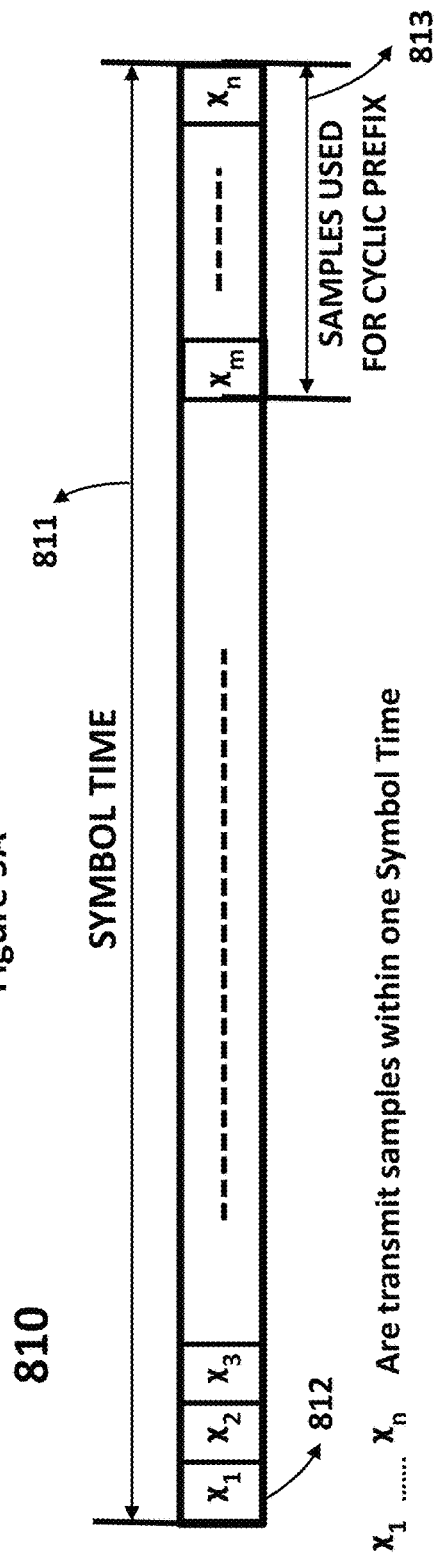

FIG. 9A depicts OFDM transmit symbol signal 850 before adding cyclic prefix. 4G, 5G and 6G (or 7G) use OFDM (orthogonal frequency division multiplexing) in their transmit path. The duration of transmit signal is one OFDM symbol 851 for 4G eNodeB and 5G (6G) gNodeB. The transmit signal 850 consists of "n" samples $x_1$ to $x_n$, 852. To eliminate inter-symbol interference "n-m" samples 853 from end of OFDM symbol are copied at the beginning of symbol or some samples from the beginning of OFDM symbol are copied at the end of symbol. The "m to n" samples are called cyclic prefix and the duration of it depends on radius of coverage of RRU and RU transmitters. These "m to n" samples at the receiver of user equipment UE (IoT device) are removed by using correlation before performing the receiver functions.

Figure 9B:
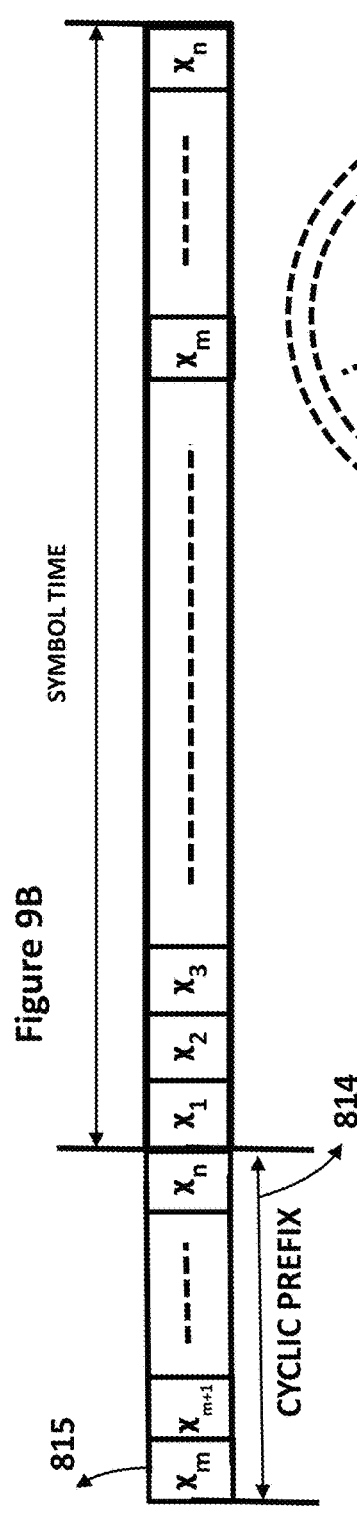

FIG. 9B shows transmit signal with cyclic prefix 854 that is added at the beginning of transmit symbol which consists of "n" samples $x_1$ to $x_n$ 852. Samples $x_m$ to $x_n$ from end of transmit symbol are copied at the beginning of "n" samples $x_1$ to $x_n$ as cyclic prefix 854. In the UE (IoT device) receiver cyclic prefix 854 is removed from received signal before the receive process starts. The process of removal of cyclic prefix is a circular correlation. The highest correlation is achieved when all samples in cyclic prefix are matched. There is always possible one or more samples in cyclic prefix are not matched due to various impairment and results in lower amount of correlation but still removal of cyclic prefix is possible. Therefore, it is possible to use one or more samples in cyclic prefix to transmit time of day to user equipment UE (IoT device).

In one embodiment of transmit signal 850 one or more samples of cyclic prefix 854 samples $x_m$ to $x_n$ is used to send the time of day to user equipment UEs or IoT devices.

In another embodiment the samples used from cyclic prefix 854 for transmitting time of day are at the start, middle, or end of cyclic prefix 854.

In another embodiment the samples used from cyclic prefix 854 for transmitting time of day are at any location in cyclic prefix 854 and the location do not change until all time of day data is transmitted.

In one embodiment the time of day is sent to user equipment UEs, or IoT devices over a number of transmit OFDM symbols.

In one embodiment the time of day includes date and time of day and date include year, month and day.

In one embodiment the bits in samples from cyclic prefix 854 are used for transmission of time of day to UEs or IoT devices.

In another embodiment the top bits in sample $(x_m)$ 855 of cyclic prefix are used to send time of day in order to mitigate effect of any noise, interference or fading.

In one embodiment only one sample of cyclic prefix 854 is used for transmitting the time of day and the first sample that is used for time of day has a detectable bit pattern to indicate that next samples at the same location in next cyclic prefixes contain the time of day.

In one embodiment more than one sample of cyclic prefix 854 is used for transmitting the time of day and the first sample that is used for time of day has a detectable bit pattern to indicate that next samples whether in present cyclic prefix or next cyclic prefixes contain the time of day.

In another embodiment the first sample of first cyclic prefix carries the hour, the first sample of second cyclic prefix carries the seconds, the first sample of third cyclic prefix carries the milliseconds, the first sample of forth cyclic prefix caries the microseconds, the first sample of fifth cyclic prefix caries nanoseconds, and if more accuracies are available the first sample of sixth cyclic prefix carries the picoseconds.

In one embodiment the bits used to represent the time of day are compressed (using one of compression algorithms) in order to use less cyclic prefix samples for transmission of time of day.

There is a time difference between transmissions of two cyclic prefixes. During this time difference the date, hour $(T_h)$, second $(T_s)$, millisecond $(T_m)$, microsecond $(T_\mu)$, or nanosecond $(T_n)$ of time of day can be incremented and this creates a significant time error between RU/RRU and UEs or IoT devices. Therefore, before sending time of day there is a need to find out if one of $(T_h)$, $(T_s)$, $(T_m)$, $(T_\mu)$, or nanosecond $(T_n)$ will be incremented during the transmission of complete time of day.

In one embodiment the date, hour $(T_h)$, second $(T_s)$, millisecond $(T_m)$, microsecond $(T_\mu)$, or nanosecond $(T_n)$ of time of day if needed is incremented before being sent to UE or IoT device.

In another embodiment, the time of day before being sent to UE or IoT device is adjusted for propagation time of IFFT through transmitter path of RU/RRU or BBU/DU up to antenna in order to reduce the time error between time of day at RU/RRU (or BBU/DU) and UEs or IoT devices.

In one embodiment the date and time of day that is sent to UE or IoT device is repeated or updated with a configurable time interval.

Figure 9C:
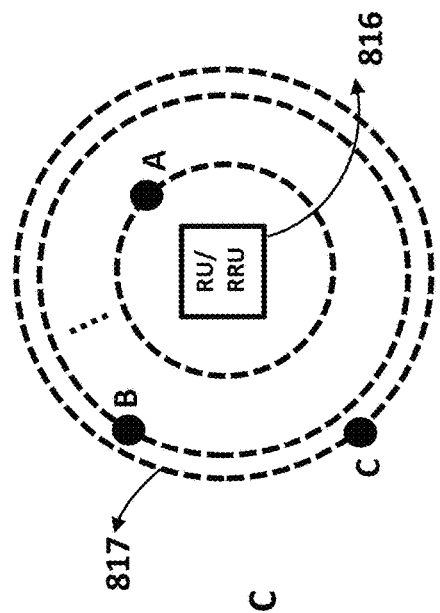

FIG. 9C depicts a typical coverage of RRU/RU in a 4G, 5G, 6G, or (7G) wireless network. UEs or IoT devices A, B, and C are at different distance from RU/RRU. Therefore, UEs or IoT devices A, B, and C receive time of day at different time which results in time error between UEs or IoT devices. These UEs or IoT devices when transmit to RU/RRU need to adjust their transmission time based on their time alignment or time advance which compensate for their difference in distance from RRU/RU. The time alignment or time advance is used to eliminate the error in time of day at UEs or IoT devices A, B, and C and make all UEs or IoT devices have the same time of day.

In one embodiment UEs or IoT devices that are at different distance from their common RRU/RU use their time alignment or time advance to adjust the time of day received from RRU/RU in order to have the same time of day.

In 4G, 5G, and 6G (or 7G) it is possible to use downlink methods similar to cyclic prefix to transmit time of day to UEs or IoT devices. These methods can utilize unused subcarriers or unused bits or messages in various downlink channels. For instance in 4G (as well as 5G and 6G) LTE there are two cell search procedures: one for initial synchronization and another for detecting neighbor cells in preparation for handover. In both cases the UE or IoT device uses two special signals broadcast on each RRU: Primary Synchronization Sequence (PSS) and Secondary Synchronization Sequence (SSS). The detection of these signals allows the UE or IoT device to complete time and frequency synchronization and to acquire useful system parameters such as cell identity, cyclic prefix length, and access mode (FDD/TDD).

In the frequency domain, the PSS and SSS occupy the central six resource blocks (RBs, 72 subcarriers), irrespective of the system channel bandwidth, which allows the UE or IoT device to synchronize to the network without a priori knowledge of the allocated bandwidth. The synchronization sequences use 62 sub-carriers in total, with 31 sub-carriers mapped on each side of the DC sub-carrier which is not used. This leaves 5 sub-carriers at each extremity of the 6 central RBs unused. These 10 unused sub-carriers can be used to transmit time of day to UEs or IoT devices. Similar to cyclic prefix the time of day should be adjusted for propagation time through transmitter path up to transmit antenna port in order to minimize time difference between gNodeB/eNodeB (RU/RRU) and UEs or IoT devices. During transmission of the time of day it is possible one of $(T_h)$, $(T_s)$, $(T_m)$, $(T_\mu)$, and $(T_n)$ has to be incremented before being sent to UEs or IoT devices due to the time it takes to transmit the time of day.

In one embodiment unused downlink sub-carriers is used to transmit time of day to UEs or IoT devices.

It is also possible to utilize unused bits or messages in various downlink channels of 4G, 5G, or 6G (7G) to transmit the time of day similar to unused sub-carriers.

In another embodiment unused bits or messages of various downlink channels is used to transmit time of day to UEs or IoT devices.

In one embodiment when unused downlink sub-carriers, bits, or messages are used, due to the time takes to send all the data, the day, hour ($T_h$), second ($T_s$), millisecond ($T_m$), microsecond ($T_\mu$), or nanoseconds ($T_n$), of time of day if needed is incremented before being sent to UE or IoT device.

Figure 9D:
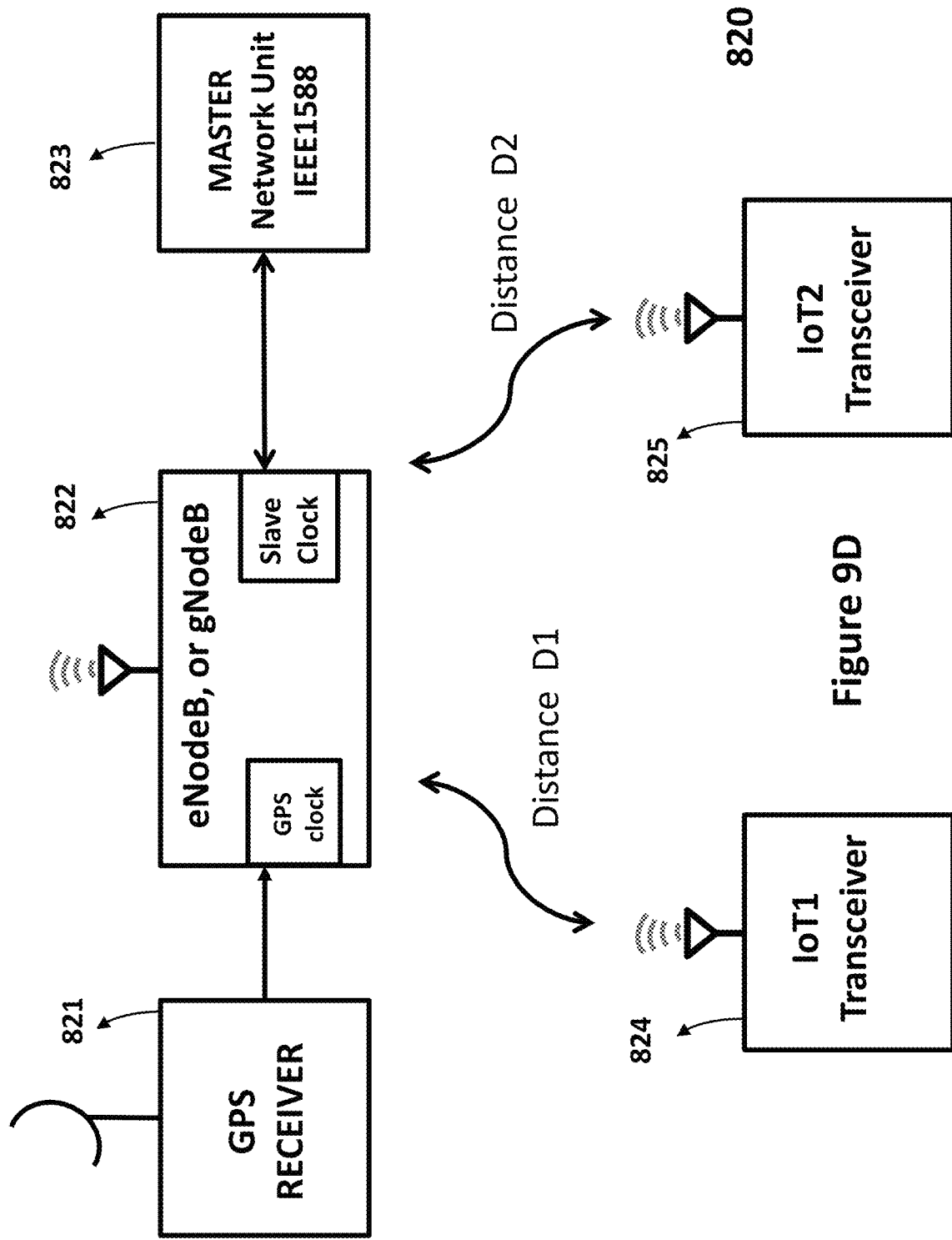

FIG. 9D shows method 820 of achieving clock synchronization and obtaining time of day for eNodeB or gNodeB. The eNodeB or gNodeB 822 uses two methods for clock synchronization and time of day. One method is to use GPS receiver 821 and another method is to act as a slave network and exchanges IEEE1588 PTP messages with a master network 823.

IoT1 device 824 and IoT2 device 825 with distance D1 and D2 from eNodeB or gNodeB 822 both frequency and phase synchronize with the eNodeB or gNodeB 822 using over the air protocol.

Figure 9E:
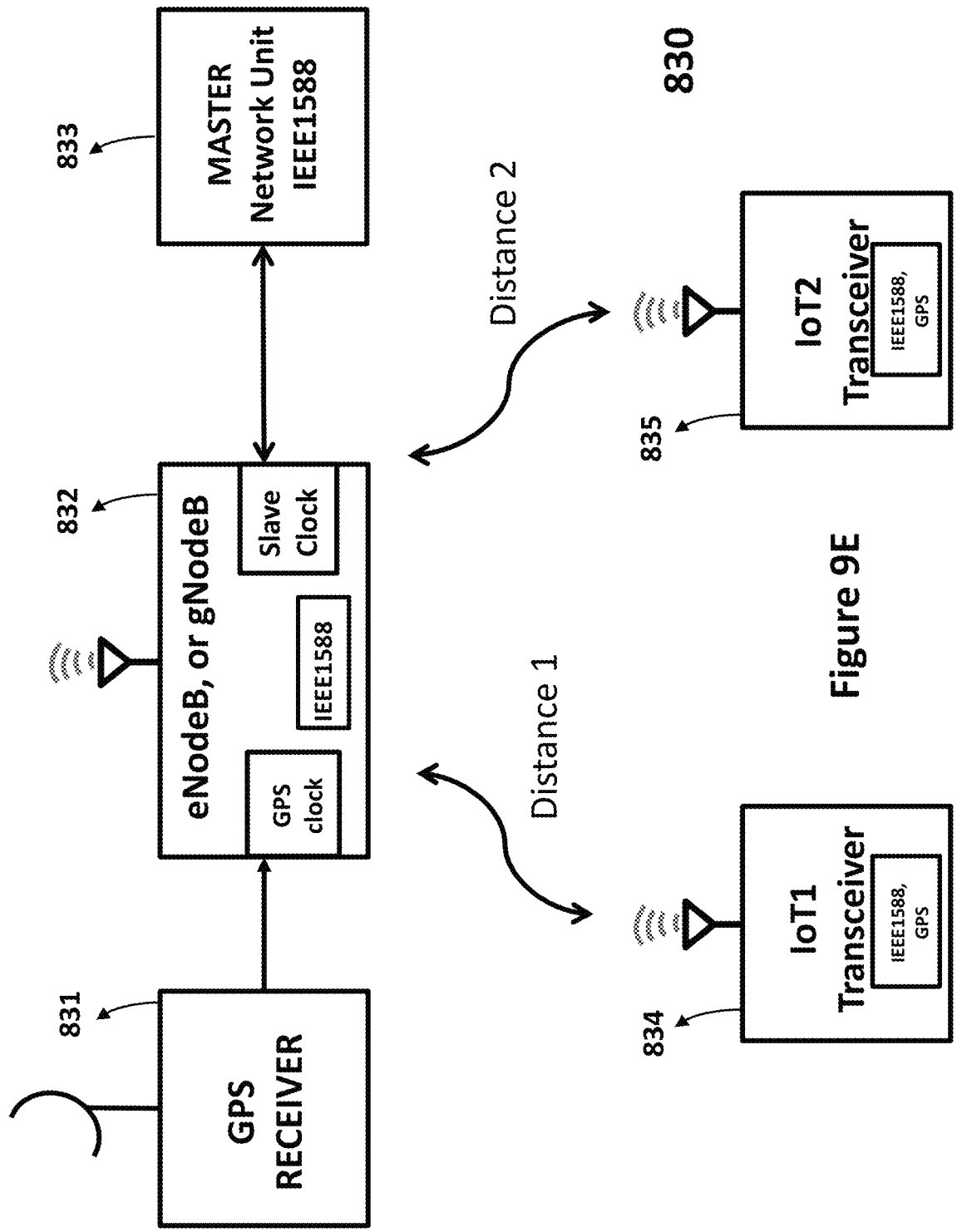

FIG. 9E shows method 830 where an IoT device uses IEEE1588 to obtain time of day. The eNodeB or gNodeB 832 uses either GPS receiver 831 or IEEE1588 PTP from a master network unit 833 to achieve clock synchronization and obtain time of day. IoT1 device 834 and IoT2 device 835 with distance D1 and D2 from RRU or RU 832 both frequency and phase synchronize with the eNodeB or gNodeB 832 using over the air protocol. To obtain time of day IoT1 device 834 and IoT2 device 835 exchange IEEE1588 PTP messages with eNodeB or gNodeB 832 or use GPS.

Figure 9F:
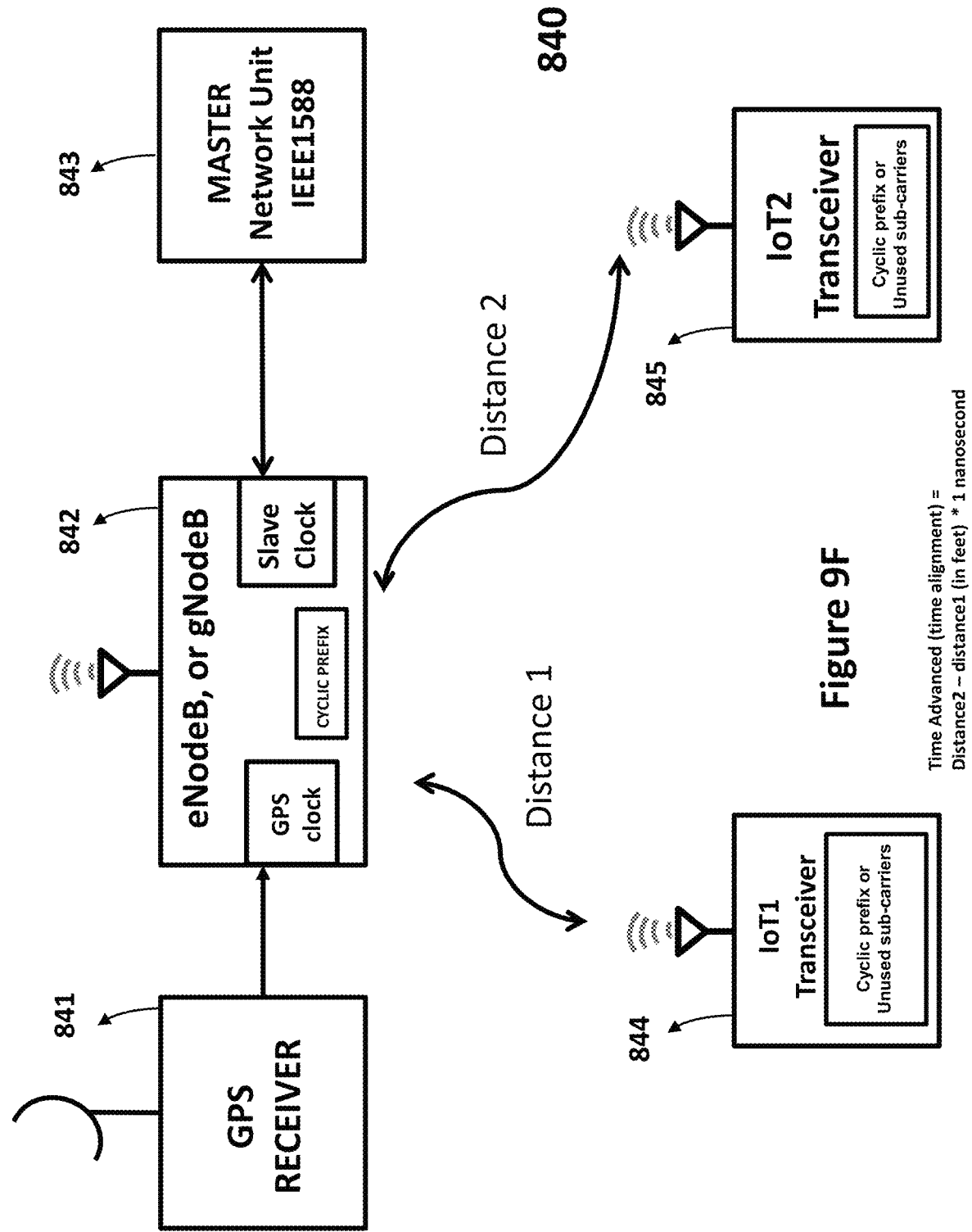

FIG. 9F illustrates method 840 where IoT device uses cyclic prefix or unused subcarriers to obtain time of day (TOD). The eNodeB or gNodeB 842 uses either GPS receiver 841 or IEEE1588 PTP from master network unit 843 to achieve clock synchronization and obtain time of day. IoT1 device 844 and IoT2 device 845 with distance D1 and D2 from eNodeB or gNodeB 842 both frequency and phase synchronize with the eNodeB or gNodeB 842 using over the air protocol. IoT1 device 844 and IoT2 device 845 receive TOD information through cyclic prefix, unused sub-carriers, unused bits or messages from eNodeB or gNodeB 842. Since IoT1 device and IoT2 device are at difference distances D1 and D2 from eNodeB or gNodeB 842 then time alignment or time advance is used to adjust time of day that IoT1 device and IoT2 device received from eNodeB or gNodeB 842. Time alignment or time advance for adjusting TOD may also consider the received signal propagation time between antenna port and decoder of IoT1 device or/and IoT2 device. IoT1 and IoT2 devices may also consider the transmit signal propagation time between modulator and antenna port and the propagation time from their antenna port to their detector.

FIG. 9G shows a scenario 850. In scenario 850 there are eNodeB1 or gNodeB1 851 and eNodeB2 or gNodeB2 852 and both use either GPS or IEEE1588 to achieve clock synchronization and obtain time of day. They both use cyclic prefix, unused sub-carriers, unused bits, unused messages or IEEE1588 PTP to propagate time of day to IoT devices that are registered with them. In the scenario 850 as shown in FIG. 9G IoT1 device 853 is attached to eNodeB1 or gNodeB1 851 and IoT2 device 854 is attached to eNodeB2 or gNodeB2 852. Since eNodeB1 or gNodeB1 851 and eNodeB2 or gNodeB2 852 obtain their time of day either from GPS or IEEE1588 PTP then both IoT1 device 853 and IoT2 device 854 should have the same time of day (TOD). If there is any difference between IoT1 device and IoT2 device TOD that will be in order of a few nanosecond (even if they use GPS to obtain TOD).

FIG. 10A depicts Ethernet frame 870 and broadcast frame 880.

In one embodiment the broadcast frame 880 uses similar structure as Ethernet frame 870.

In one embodiment the broadcast frame 880 sends the time of day in the payload.

In one embodiment the broadcast frame 880 instead of sending destination address sends the time of day.

In another embodiment the source address (which is a media access control MAC address) of the broadcast frame 880 or an IP address is the identity code of a transceiver (IoT device, sensor, WiFi router, RRU, RU, private base station, or any other wireless device).

In one embodiment, two wireless devices (IoT devices, sensors, and others) use Ethernet packets or frame to exchange information between them when both source and destination addresses are used to identify the two wireless devices. One wireless device retrieves the address of another wireless device from its broadcast packet and then using Ethernet packets establishes direct communication between them to exchange information data.

Figure 10B:
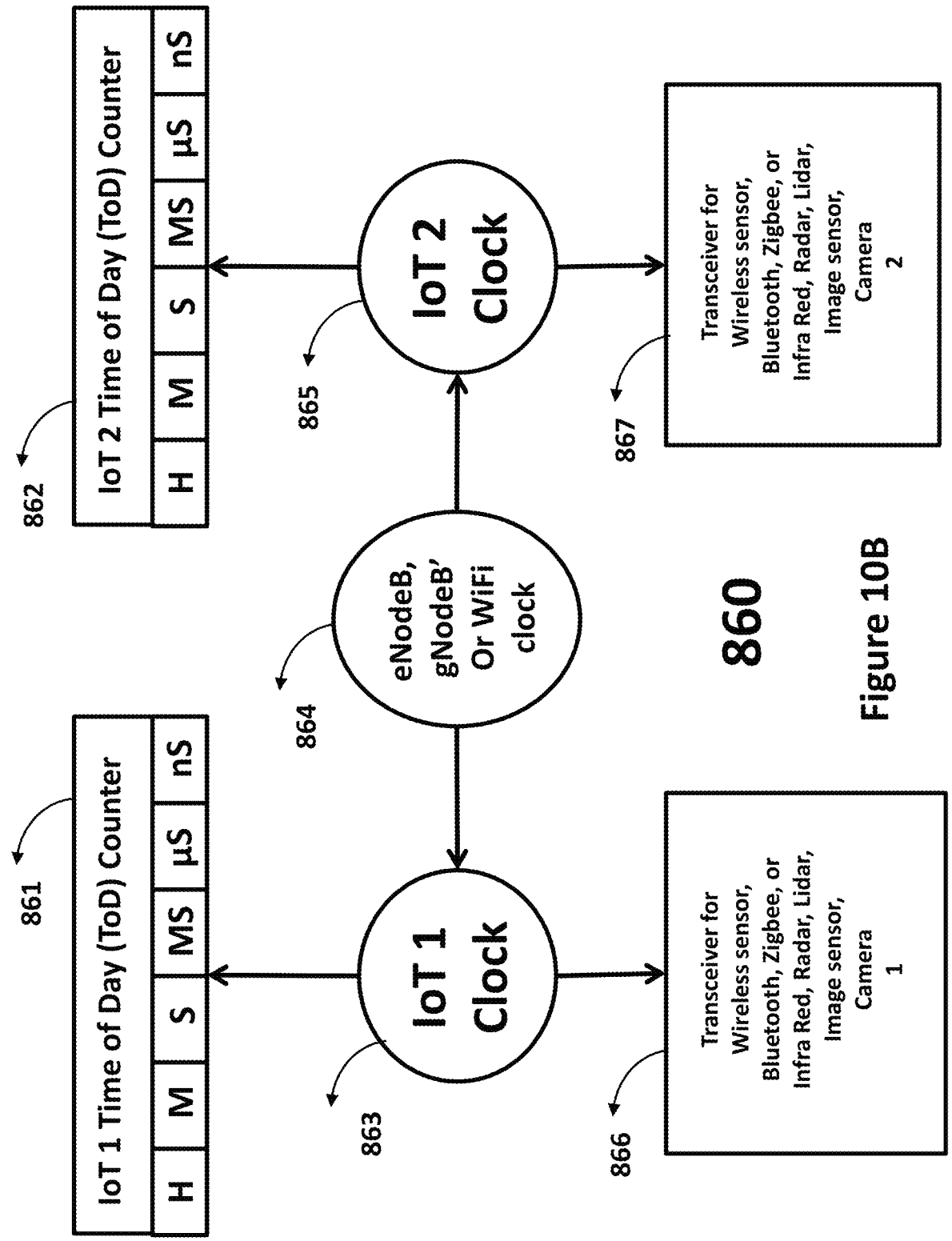

FIG. 10B shows two IoT devices 860. Both IoT1 device and IoT2 device have their clocks 863 and 865 frequency and phase synchronized with eNodeB, gNodeB or WiFi clock 864. IoT1 and IoT2 devices 866 and 867 can support a wireless sensor transceiver, a Bluetooth transceiver, a Zigbee transceiver, an Infrared transceiver, a Radar transceiver, a Lidar transceiver, an ultrasonic transceiver, a WiFi transceiver, and a 4G, 5G, 6G, or 7G transceiver. IoT1 and IoT2 devices 866 and 867 use 4G, 5G, 6G, or 7G transceivers to obtain clock frequency and phase synchronization from 4G, 5G, 6G, or 7G eNodeB, gNodeB or WiFi 864. Both IoT devices support Radar, Lidar, ultrasonic, and Camera.

IoT1 clock 863 increments time of day 861 for IoT1 device 866 and IoT2 clock 865 increments time of day 862 for IoT2 device 867. Both IoT devices 866 and 867 use eNodeB, gNodeB 864, or WiFi to achieve clock frequency and phase synchronization as well as obtaining time of day 861 and 862. IoT1 866 and IoT2 867 can also use GPS to obtain time of day and clock. IoT1 866 and IoT2 867 should have their transmit frequency +/−0.1 part per million (PPM) accurate compared with the frequency they receive from eNodeB or gNodeB 864. Worst case scenario is when IoT1 866 transmit frequency is +0.1 PPM compared with received frequency and IoT2 867 transmit frequency is −0.1 PPM compared with received frequency from eNodeB or gNodeB 864. A difference of 0.2 PPM between IoT1 clock 863 and IoT2 clock 865 produce very negligible error when used for incrementing IoT1 time of day 861 and IoT2 time of day 862. In addition IoT1 clock 863 and IoT2 clock 865 as well as IoT1 TOD 861 and IoT2 TOD 862 are continuously updated to prevent error accumulation and maintain the error negligible.

Figure 10C:
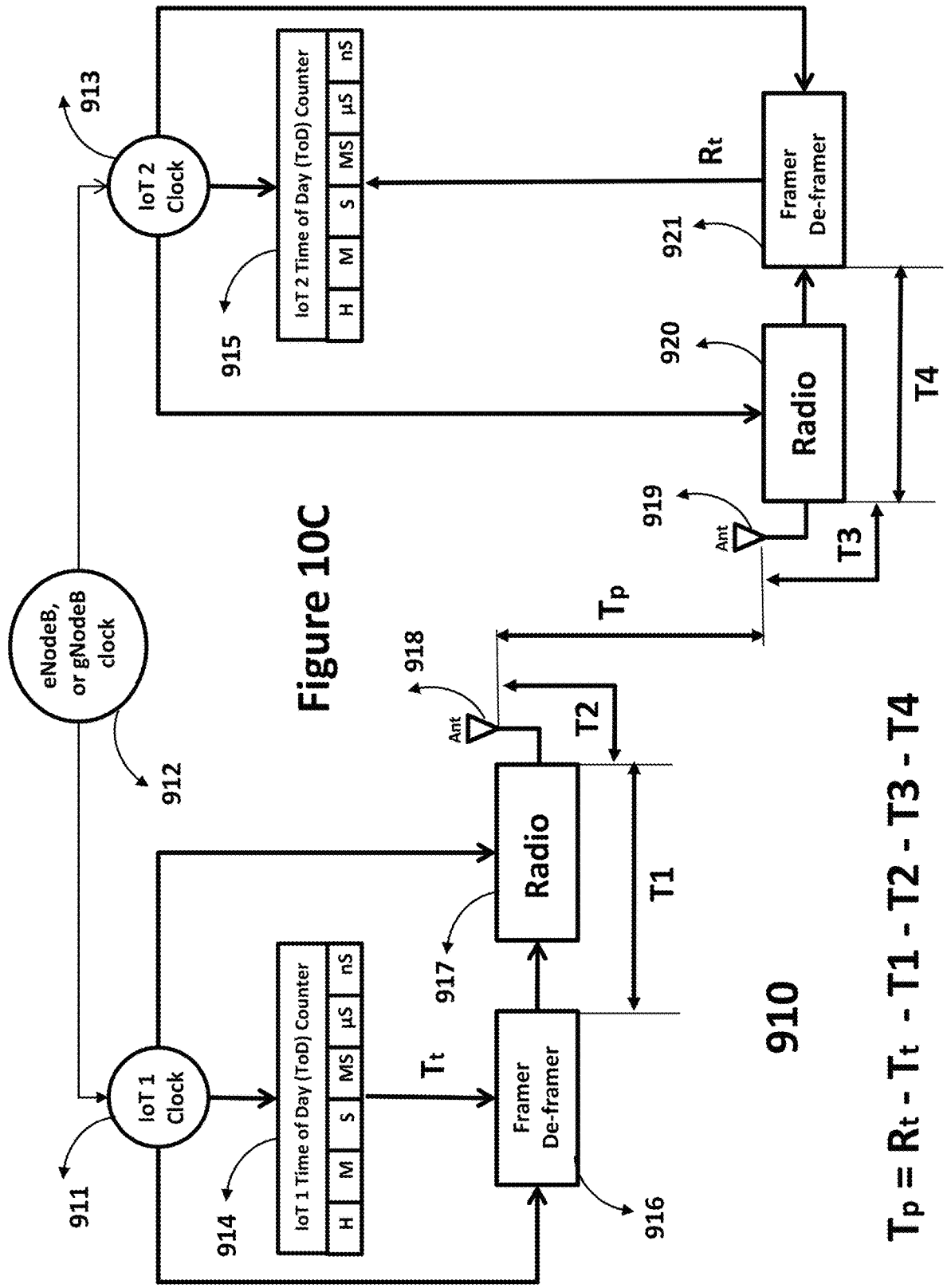

FIG. 10C shows solution 910 to estimate and calculate the distance between and approaching speed of IoT1 device and IoT2 device. IoT device comprises of IoT1 clock 911, IoT1 time of day (TOD) counter 914, IoT1 framer/de-framer 916, radio 917, and antenna 918. IoT2 device comprises of IoT2 clock 913, IoT2 time of day (TOD) counter 915, IoT2 framer/de-framer 921, radio 920, and antenna 919. Both IoT1 clock 911 and IoT2 clock 913 achieve frequency and phase synchronization through eNodeB or gNodeB 912 and obtain their time of day from eNodeB or gNodeB 912. The IoT devices also can obtain their time of day using GPS receiver. IoT1 device uses time of day (TOD) counter 914 to maintain TOD and is incremented by IoT1 clock 911.

Similarly IoT2 device uses time of day (TOD) counter 915 to maintain TOD and is incremented by IoT2 clock 913.

IoT1 device uses framer/de-framer 916 to frame transmit broadcast packet signal or transmit Ethernet packet signal in order to transmit to other IoT devices through radio 917 and antenna 918. IoT2 device receives the broadcast or Ethernet packet signal from IoT1 device through antenna 919, radio 920 and framer/de-framer 921.

Similarly IoT2 device uses framer/de-framer 921 to frame transmit broadcast packet signal or transmit Ethernet packet signal in order to transmit to other IoT devices through radio 920 and antenna 919. IoT1 device receives the broadcast or Ethernet packet signal from IoT2 device through antenna 918, radio 917 and framer/de-framer 916.

Since both IoT1 device and IoT2 device use eNodeB or gNodeB 912 to achieve frequency and phase synchronizations as well as obtain time of day it can be assumed that both IoT1 and IoT2 devices have the same clock and time of day. Therefore, IoT1 clock 911 and IoT2 clock 913 have similar accuracy with negligible error and both IoT1 and IoT2 devices have identical time of day 914 and 915. It is also possible that the TOD of all IoT devices is not identical and there is error between the times of day (TOD) of a pair of IoT devices.

IoT1 device in its broadcast packet transmit time of day $T_t$ (time stamp) through framer 916, radio 917 and antenna 918. IoT2 device receives the broadcast packet from IoT1 device through its antenna 919, radio 920, and de-framer 921. IoT2 device record the receive time $R_t$ of broadcasted $T_t$ by IoT1 device. Therefore, IoT2 device has two TODs, the broadcasted TOD $T_t$ (time stamp) by IoT1 device and received TOD $R_t$ when the broadcast TOD was received. The difference between these two time ($R_t-T_t$) is the propagation time between IoT1 framer 916 and IoT2 de-framer 921 when the TOD of both IoT1 and IoT2 devices have negligible error or are identical.

Now if we subtract the propagation time through IoT1 radio T1, antenna T2, IoT2 antenna T3 and radio T4 we obtain propagation time Tp between antenna port of IoT1 and IoT2 devices. Both propagation time through IoT1 radio (T1), and antenna 918 (T2) are included in the payload of broadcast packet.

$$Tp=Rt-T_t-T1-T2-T3-T4$$

The distance between IoT1 device and IoT2 device is calculated using the propagation time Tp and using two consecutive Tp measurements the approaching speed between IoT1 device and IoT2 device can be calculated. Transmit TOD $T_t$ by IoT1 device can be adjusted to include propagation time through radio 917 (T1) and propagation time from radio 917 to output port of antenna 918 (T2). Therefore, transmit TOD inserted in broadcast frame is the TOD at output port of antenna 918. TOD also includes the time takes to insert it in the broadcast frame and any time taken for the broadcast frame to reach the radio 917. All the times are calculated by clock cycles so that TOD at the TOD counter and TOD leaving the antenna are the same. The same applies to IoT2 device and all other IoT devices in the smart environment.

Received TOD $R_t$ by IoT2 device can also be adjusted to include propagation times (T3 and T4) through antenna 919 input port to radio 920 and radio 920. Therefore, received TOD retrieved from broadcast frame is TOD when ($T_t$) arrives at the input port of antenna 919. TOD also includes the time takes to retrieve it from the broadcast frame. The same applies to IoT1 device and all other IoT devices in the smart environment. In this case:

$$Tp=R_t-T_t$$

If the time of day at all IoT devices in the smart environment is identical within less than 10 nanosecond then any IoT device in the smart environment knows the distance of other IoT device with less than 10 feet error by receiving broadcast frames or packets from other IoT devices.

If the time of day at IoT devices in the smart environment are in error more than 10 nanoseconds then a two way communication is required.

FIG. 10D shows protocol 930 to estimate and calculate distance between IoT1 device (object) 931 and IoT2 device (object) 932. IoT1 device 931 sends a broadcast packet that contains the time of day t1 at the antenna port of IoT1 device 931. IoT2 device 932 receives the broadcast packet from IoT1 device 931, retrieves t1 from payload and records time of day t2 when t1 arrived at the antenna port of IoT2 device 932. IoT2 device 932 also retrieves the address of the IoT1 device from broadcast packet (frame).

Next IoT2 device 932 sends an Ethernet packet (frame) that contains in its payload the time of day t3 at the antenna port of IoT2 device 932, t1, and t2 to IoT1 device 931 using its address. IoT1 device 931 receives the Ethernet packet (frame) from IoT2 device 932, retrieves t3, t2, t1 and records time of day t4 when t3 arrived at the antenna port of IoT1 device 931. Then IoT1 device uses IoT2 device address and sends an Ethernet packet that contains in its payload t4, t3, t2, and t1 to IoT2 device. IoT2 device receives the Ethernet packet and retrieves t4. At this point IoT1 device 931 and IoT2 device 932 have 4 times t1, t2, t3 and t4 to calculate the distance between IoT1 device 931 and IoT2 device 932.

Protocol 930 is used when IoT1 device 931 and IoT2 device 932 do not have frequencies and time of day that are 100% identical or with very negligible error. Using t1, t2, t3 and t4 the propagation time between antenna port of IoT1 device 931 and antenna port of IoT2 device 932 is $$\text{Propagation time}=(t2-t1+t4-t3)/2$$

Then propagation time is used by IoT1 device 931 and IoT2 device 932 to find distance between IoT1 device 931 and IoT2 device 932 and then two consecutive distance measurements at two specific times is used to calculate approaching speed between IoT1 device 931 and IoT2 device 932.

Figure 10E:
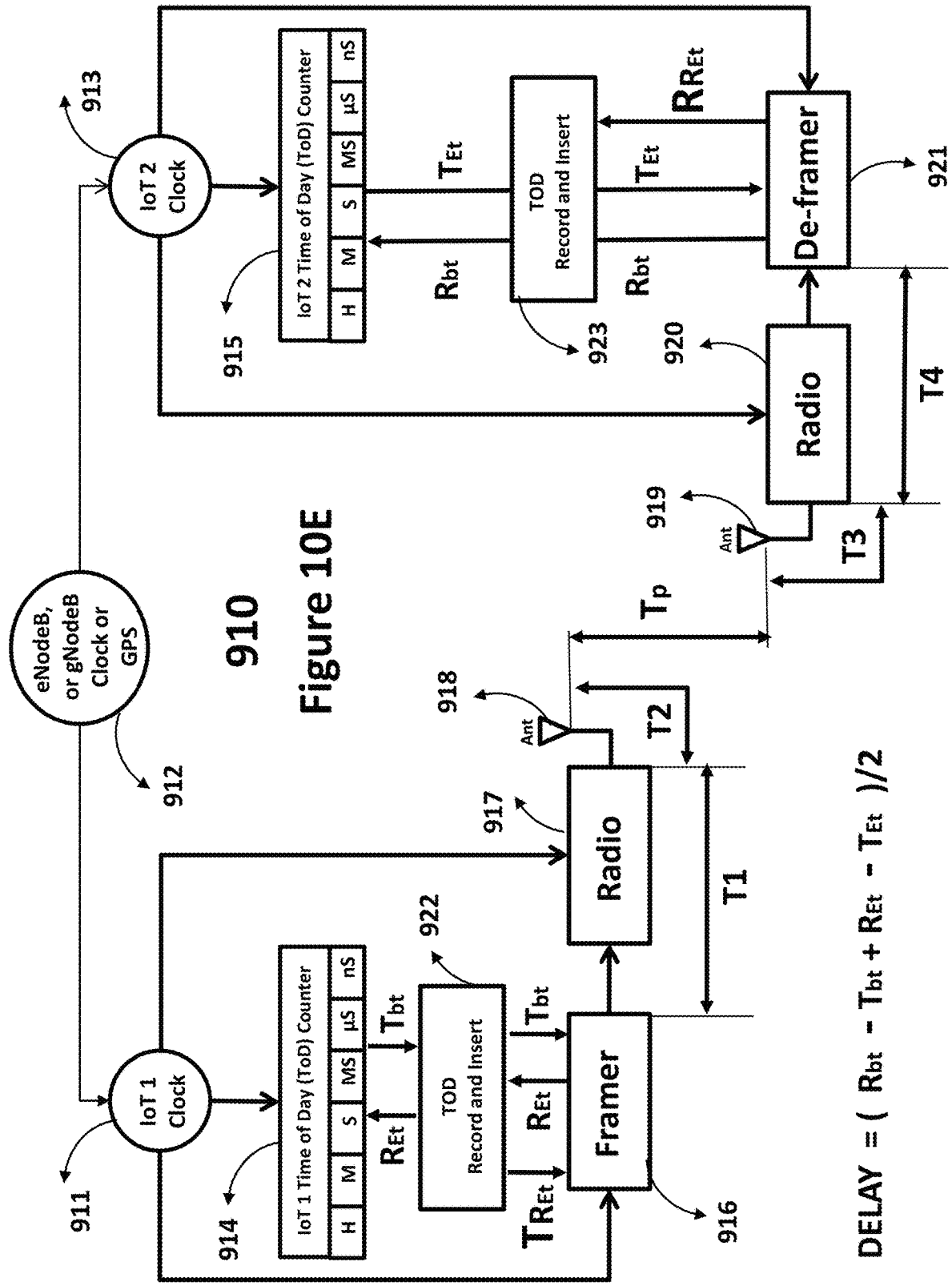

FIG. 10E shows implementation of protocol 930. IoT1 device sends broadcast TOD ($T_{bt}$) in a broadcast packet. Broadcast TOD ($T_{bt}$) can be either adjusted for delays T1 from TOD insertion into the framer to the output of the radio 917 and T2 from output of radio 917 to the input of antenna 918 by record and insert block 922 or T1 and T2 are included in broadcast packet payload. IoT2 device receives the broadcast packet from IoT1 device through antenna 919, radio 920 and framer/de-framer 921 and retrieves $T_{bt}$ and record time of day $R_{bt}$ when $T_{bt}$ is arrived and retrieved. $R_{bt}$ can be adjusted for T3 and T4 delays from output of antenna 919 to input of radio 920 and from input of radio 920 to the time it is extracted from de-framer 921 by record and insert block 923.

In next step IoT2 device sends an Ethernet packet to IoT1 device using IoT1 device address retrieved from its broadcast packet and includes an Ethernet time of day $T_{Et}$ in its payload. Ethernet time of day $T_{Et}$ can be adjusted for delays (T1 and T2 of IoT2 device) from radio 920 and antenna 919 by record and insert block 923 or delays (T1 and T2 of IoT2 device) are included in Ethernet packet payload. IoT1 device receives the Ethernet packet from IoT2 device through antenna 918, radio 917 and framer/de-framer 916 and retrieves $T_{Et}$ and record time of day $R_{Et}$ when $T_{Et}$ is arrived and retrieved. $R_{Et}$ can be adjusted for delays (T3 and T4 of IoT1 device) through antenna 918 and radio 917 by record and insert block 922.

Next IoT1 device sends time of day $R_{Et}$ when it received $T_{Et}$ from IoT2 device by an Ethernet packet to IoT2 device using its address. IoT2 device receives $R_{Et}$ and then uses $T_{bt}$, $R_{bt}$, $T_{Et}$ and $R_{Et}$ to calculate the propagation time between IoT1 device and IoT2 device by following equation. Propagation time between IoT1 and IoT2=$(R_{bt}-T_{bt}+R_{Et}-T_{Et})/2$ When all times are adjusted for transmitter and receiver delays explained above. When T1, T2, T3, and T4 are not included then following equation is used.

$$\text{Propagation time between } IoT1 \text{ and } IoT2 = (R_{bt}-T_{bt}+R_{Et}-T_{Et})/2 - (T1+T2 \text{ of } IoT1)/2 - (T1+T2 \text{ of } IoT2)/2 - (T3+T4 \text{ of } IoT2)/2 - (T3+T4 \text{ of } IoT1)/2$$

Propagation time results in distance between IoT1 device and IoT2 device and two consecutive distance calculation results in the speed IoT1 device and IoT2 device approach each other.

Figure 11:
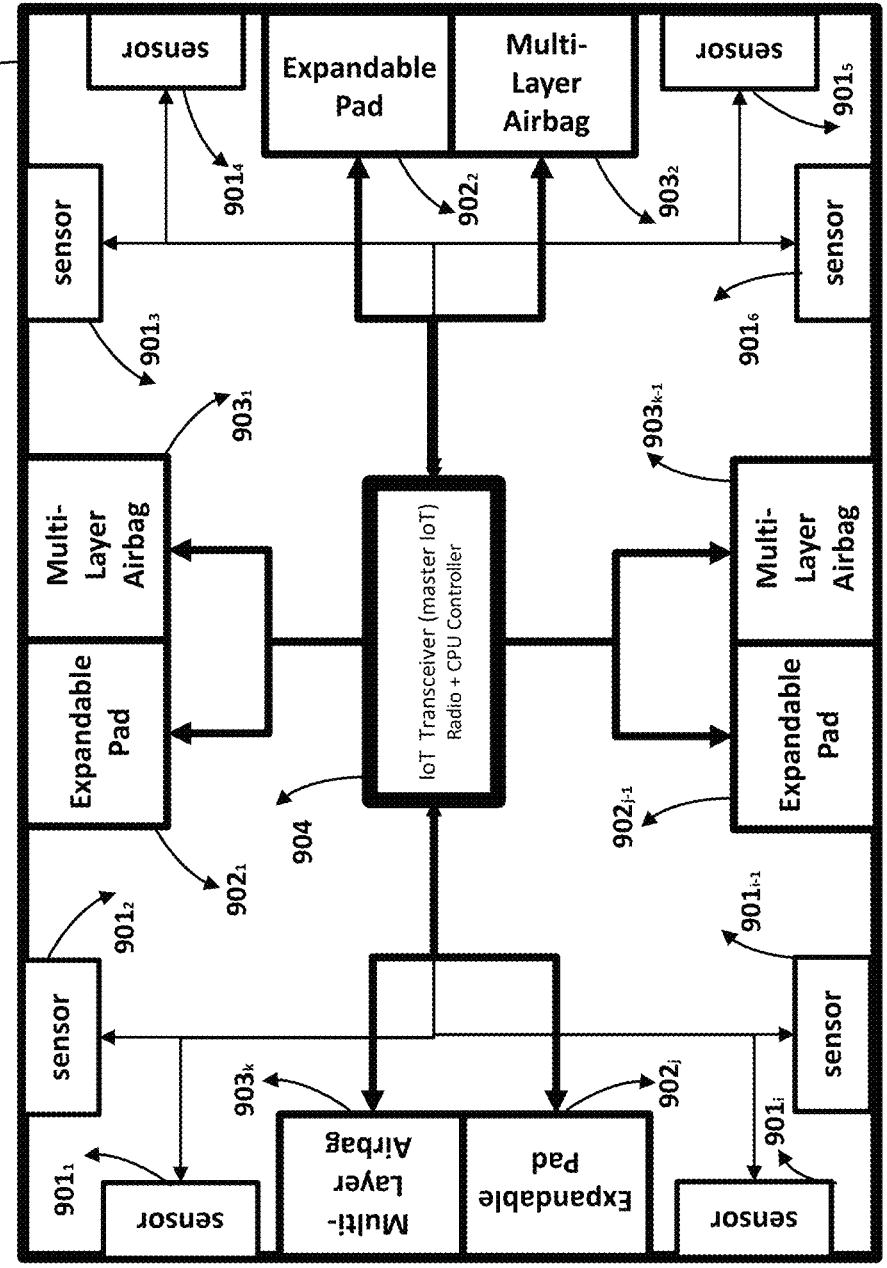
FIG. 11 depicts an IoT protection system for moving and stationary objects

FIG. 11 illustrates an embodiment of a navigation and protection system (NPS) for vehicle/object (IoT device) 900. In general, the NPS for vehicle/object (IoT device) 900 performs navigation and provides external body protection by applying voltage to two ends of an expandable pad and/or inflating a multilayer airbag. The NPS through its IoT transceiver (master IoT device) 904 registers with an IoT network and exchanges an operation information data (OID) related to NPS's operation and its status. NPS for vehicle/object (IoT device) 900 uses the OID from IoT network and detected information data (DID) from various sensors (including slave IoT devices) 901$_1$ to 901$_i$ to detect any malfunction of the vehicle/object (IoT device) 900 or approaching of any external objects that results in an impact. When NPS detects a potential impact based on its artificial intelligence analyses of the DID received from sensors (wireless sensor, internal sensors, internal devices, and slave IoT devices) 901$_1$ to 901$_i$, broadcasts its problem to the IoT network and activates one or more of the expandable pads 902$_1$ to 902$_j$ or/and one or more of the multilayer airbag 903$_1$ to 903$_k$ to minimize the damage to the vehicle/object (IoT device) 900 due to impact. NPS also uses the received DID to navigate the vehicle/object (IoT device) 900 when no imminent impact is detected.

NPS for vehicle/object (IoT device) 900 includes, among other things, sensors 901$_1$ to 901$_i$ (including wireless sensors and slave IoT devices), IoT transceiver (master IoT device) 904, expandable pads 902$_1$ to 902$_j$, and multilayer airbags 903$_1$ to 903$_k$.

In one embodiment the NPS acts as a standalone IoT device used by various objects.

In one embodiment the NPS obtains time of day (TOD) and calendar date directly or through the vehicle/object (IoT device) 900 that uses the NPS.

In another embodiment the NPS uses time of day to define a time for the operation of various sensors (including wireless sensors, and slave IoT devices) 901$_1$ to 901$_i$.

In one embodiment the sensors 901$_1$ to 901$_i$ are slave IoT devices to master IoT device 904 or wireless sensors.

In one embodiment, the vehicle/object (IoT device) 900 is a moving object, stationary object, or flying object.

In one embodiment of the NPS for vehicle/object (IoT device) 900, multiple expandable pads 902$_1$ to 902$_j$ and multiple multilayer airbags 903$_1$ to 903$_k$ are mounted on all external sides of vehicle/object (IoT device) 900 to provide protection for impacts due to external objects at any external side of vehicle/object (IoT device) 900.

In one embodiment of the NPS for vehicle/object (IoT device) 900, the expandable pads 902$_1$ to 902$_j$ and multilayer airbags 903$_1$ to 903$_k$ are mounted on the main body frame of the vehicle/object (IoT device) 900 to provide a firm and strong support.

In another embodiment of the NPS for vehicle/object (IoT device) 900, by activating expandable pads 902$_1$ to 902$_j$ and/or multilayer airbags 903$_1$ to 903$_k$ the impact force to vehicle/object (IoT device) 900 will be lowered due to absorption or diffraction and provides more protection to the passengers of vehicle/object (IoT device) 900.

In one embodiment of the NPS for vehicle/object (IoT device) 900, one or more of the multilayer airbags 903$_1$ to 903$_k$ at one or multiple sides of the vehicle/object (IoT device) 900 is inflated to protect the external of vehicle/object (IoT device) 900 from fall, crash or impact with an external object.

In one embodiment of the NPS for vehicle/object (IoT device) 900, one or more of the expandable pads 902$_1$ to 902$_j$ at one or multiple sides of the vehicle/object (IoT device) 900 is activated by applying voltage to two ends of expandable pad to protect the external of vehicle/object (IoT device) 900 from fall, crash or impact with an external object.

In one embodiment of the NPS for vehicle/object (IoT device) 900, IoT transceiver (master IoT device) 904 resets, and configures itself based on configuration data stored in its memory and then starts to execute artificial intelligence executable software which controls all aspects of navigation and protection of the vehicle/object (IoT device) 900 using the DID provided by all monitoring devices or/and sensors (including wireless sensors or slave IoT devices) 901$_1$ to 901$_i$.

In one embodiment of the NPS for vehicle/object (IoT device) 900, multiple monitoring devices or sensors (wireless sensors, or slave IoT devices) 901$_1$ to 901$_i$ are distributed at various locations internal and external to vehicle/object (IoT device) 900 and each has a unique IP address (or MAC address) which is used to communicate with the IoT transceiver (master IoT device) 904 to avoid collision or confusion of the information data received by the controller CPU of the IoT transceiver (master IoT device) 904 from the sensors internal or external to the vehicle/object (IoT device) 900.

In one embodiment of the NPS for vehicle/object (IoT device) 900, the monitoring devices or sensors (wireless sensors, or slave IoT devices) 901$_1$ to 901$_i$ can be at least one of an image sensor, a wireless sensor, a Radar, a Camera, a heat sensor, a speed sensor, an acceleration sensor, a ultrasonic sensor, a proximity sensor, a pressure sensor, a G (gravity) sensor, an IR (infrared), Lidar sensor, ultrasonic sensor, laser and others.

In one embodiment of the NPS for vehicle/object (IoT device) 900, a wireless sensor (slave IoT device) transmits (records completion of transmission at input of transmit antenna port) a coded signal similar to a unique identity code signal or a unique IP address signal and receives (record the completion of reception at receive antenna port) a reflected signal of the unique identity code signal, or the unique IP address signal from objects in surrounding environment of the vehicle/object (IoT device) 900 to avoid collision.

In another embodiment of the NPS for vehicle/object (IoT device) 900, the wireless sensor (salve IoT device) uses the time of completion of transmission of the unique identity code signal or the unique IP address signal at its transmit antenna port and the time of completion of the reception of the reflected signal of the unique identity code signal or the unique IP address signal at its receive antenna port to estimate free space traveling time of the unique identity code signal or the unique IP address signal to calculate a distance and an approaching speed of an object in the surrounding environment of the vehicle/object (IoT device) 900.

In one embodiment of the NPS for vehicle/object (IoT device) 900, the wireless sensor (slave IoT device) uses a time stamp (time of day) received from wireless sensor (slave IoT device) of NPS that belongs to another vehicle/object (IoT device) to estimate the distance between the two vehicles/objects (IoT devices).

In one embodiment of the NPS for vehicle/object (IoT device) 900, the wireless sensor (slave IoT device) uses time of day (time stamp) of a broadcast packet at the antenna port of transmitter of the wireless sensor (slave IoT device) of a NPS that belongs to another vehicle/object (IoT device) and the time of day its own receiver receives the broadcast packet (time stamp) at its receiver antenna port to estimate the free space traveling time of the time stamp in the broadcast data. Then the free space traveling time is used to calculate the distance between the two vehicles/objects (IoT devices).

In another embodiment, the wireless sensor (slave IoT device) uses one IP (MAC) address to communicate with IoT transceiver (master IoT device) 904 and a second IP address for transmitting a unique IP address signal over the air to monitor objects in surrounding environment.

In another embodiment, the wireless sensor (slave IoT device) uses a single IP4 or IP6 address for both communicating with IoT transceiver (master IoT device) 904 and transmitting a signal over the air.

In one embodiment of the NPS for vehicle/object (IoT device) 900, IoT transceiver (master IoT device) 904 communicates with at least one of a cellular network (4G, 5G and beyond, 6G, 7G), a WiFi network, and a private network to provide its own information data to the network and obtain an information data about other objects in its surrounding environment.

In one embodiment of the NPS for vehicle/object (IoT device) 900, the IoT transceiver (master IoT device) 904 supports IEEE1588 to obtain time of day (TOD) from at least one of a cellular base station (4G, 5G and beyond, 6G, 7G), a WiFi network, and a private network.

In one embodiment of the NPS for vehicle/object (IoT device) 900, in order to avoid collision, at least one of a cellular base station (4G, 5G and beyond, 6G, 7G), a WiFi router, and a private network broadcasts to vehicle/object (IoT device) 900 a channel, a frequency, a modulation, and an absolute time with a time slot duration when its wireless sensors (slave IoT devices) can transmit the unique IP address signal and receive the reflected unique IP address signal from various objects in the surrounding environment in order to measure a distance and an approaching speed of various objects.

In one embodiment of the NPS for vehicle/object (IoT device) 900, in order to avoid collision, at least one of a cellular base station (4G, 5G and beyond, 6G, 7G), a WiFi router, and a private network broadcasts to vehicle/object (IoT device) 900 a channel, a frequency, a modulation, and an absolute time with a time slot duration when its wireless sensor (slave IoT device) can broadcast its information data.

In another embodiment of the NPS for vehicle/object (IoT device) 900, the wireless sensor (slave IoT device), over the air, broadcasts information data that includes a time stamp indicating time of day, a method the time of day was obtained (IEEE1588, cyclic prefix, downlink unused sub-carriers, downlink channels unused bits/messages or GPS), type of the vehicle/object (IoT device) 900, location coordinates (obtained from GPS receiver), function of the object, status of the object, specification of object, the identity number or IP (media access control MAC) address of wireless sensor (slave IoT device), signal propagation time through transmitter of the wireless sensor (slave IoT device) up to the input of transmit antenna, and estimated mass of the vehicle/object (IoT device) 900. If the object is a traffic light then its color (green, yellow, red) indicates the status of the object.

In one embodiment of the NPS for vehicle/object (IoT device) 900, two or more type of sensors (Radar, Lidar, Camera, ultrasonic sensor, laser and Image sensor) can be used to better monitor the surrounding environment of the vehicle/object (IoT device) 900 and calculate and estimate parameters of the surrounding environment. All wireless sensing devices operate during the time slot assigned to NPS for vehicle/object (IoT device) 900 by IoT network.

In one embodiment of the NPS for vehicle/object (IoT device) 900, an image sensor or Lidar is used to monitor the vehicle/object (IoT device) 900 surrounding environment, and independently calculate and estimate a distance and an approaching speed of an object in the surrounding environment.

In one embodiment of the NPS for vehicle/object (IoT device) 900, using typical objects in an environment an image verification data base and a distance calibration data base that relates the size of the image to distance of the object from the image sensor is created and stored in memory of the image sensor.

In one embodiment of the NPS for vehicle/object (IoT device) 900, a wireless sensor (slave IoT device) and an image sensor, and/or Lidar are used to monitor the vehicle/object (IoT device) 900 surrounding environment, and each independently calculate and estimate a distance and an approaching speed of the objects in its surrounding environment and use the information data to make a better decision (by the artificial intelligence algorithm) to activate one or more multilayer air bags and/or expandable pads.

In another embodiment, the vehicle/object (IoT device) 900 can be an automobile, a robot, a flying car, a small plane, a drone, a glider, a human or any flying and moving vehicle/device/object/equipment.

Figure 12:
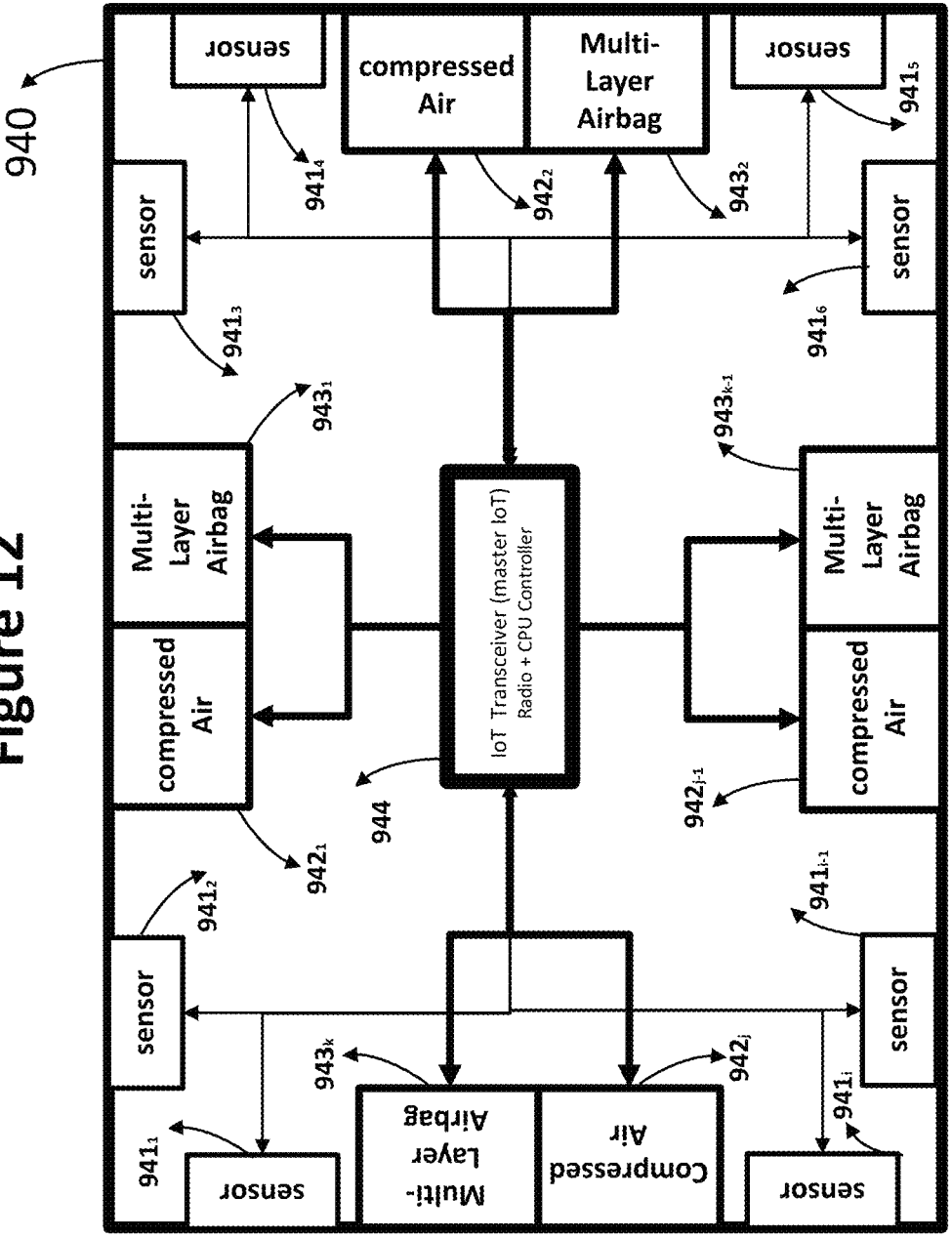
FIG. 12 illustrates an IoT protection system for flying objects

FIG. 12 illustrates an embodiment of a NPS for a flying object (IoT device) 940. In general, the NPS for the flying object (IoT device) 940 provide protection by releasing compressed air and/or inflating a multilayer airbag, and control the navigation. The NPS receives information data related to operation status and surrounding environment of the flying object (IoT device) 940 from IoT transceiver (master IoT device) 944, sensors (including wireless sensors, and slave IoT device) 941$_1$ to 941$_i$ to detect any malfunction of the flying object (IoT device) 940 that results in loss of altitude, vertical fall due to gravity force and eventual crash to the ground. When the NPS detects a fall through its CPU controller's artificial intelligence which analyses the information data received from the monitoring devices/sensors (including wireless sensors, and slave IoT devices) 941$_1$ to 941$_i$ which include information data related to devices internal to flying object (IoT device) 940 and its surrounding environment's parameters, it broadcasts its problem using IoT transceiver (master IoT device) 944 and activates at least one of the compressed air 942$_1$ to 942$_j$ to release air to slow down the fall at certain distance from ground before the flying object (IoT device) 940 crashes and then activates one or more of the multilayer airbag 943$_1$ to 943$_k$ for smoother landing or crash.

The NPS for the flying object (IoT device) 940 includes, among other things, sensors (including wireless sensors, Radar, Lidar, Image sensor, ultrasonic, and slave IoT devices) 941$_1$ to 941$_i$, IoT transceiver (master IoT device) 944, compressed air units 942$_1$ to 942$_j$, and multilayer airbags 943$_1$ to 943$_k$.

In one embodiment of the NPS for the flying object (IoT device) 940, activation of a subset of compressed air units 942$_1$ to 942$_j$ and multilayer airbags 943$_1$ to 943$_k$ allows for smoother crash or landing on any side of the flying object (IoT device) 940.

In one embodiment, the NPS for the flying object (IoT device) 940 uses a centralized compressed air unit with multiple outlets at different sides of the flying object (IoT device) 940 and when activated the air is released only from the outlets on the side that flying object (IoT device) 940 lands or crash to the ground.

In one embodiment of the NPS for the flying object (IoT device) 940, one or more of the multilayer airbags 943$_1$ to 943$_k$ at one or multiple sides of the flying object (IoT device) 940 are inflated to make the crash or landing as smooth as possible.

In one embodiment of the NPS for the flying object (IoT device) 940, NPS through the controller CPU of the IoT transceiver 944 resets, and configures itself based on a configuration data stored in its memory and then starts executing an artificial intelligence software which controls all aspects of navigation and protection of the flying object (IoT device) 940 using information data provided by sensors (including wireless sensors, Radar, Lidar, Image sensor, ultrasonic, and slave IoT devices) 941$_1$ to 941$_i$.

In one embodiment of the NPS for the flying object (IoT device) 940, each sensor has an IP (MAC) address which is used to communicate with the IoT transceiver 944 similar to an IP network to avoid collision or confusion of the information data received by the IoT transceiver 944 from sensors internal or external to the flying object (IoT device) 940.

In one embodiment of the NPS for the flying object (IoT device) 940, each sensor sends its information data to the controller CPU of the IoT transceiver (master IoT device) 944 by using wireless and/or wired communication.

In another embodiment, the flying object (IoT device) 940 can be a drone, a flying car, a small plane, a glider, and a flying human or robot.

Figure 13:
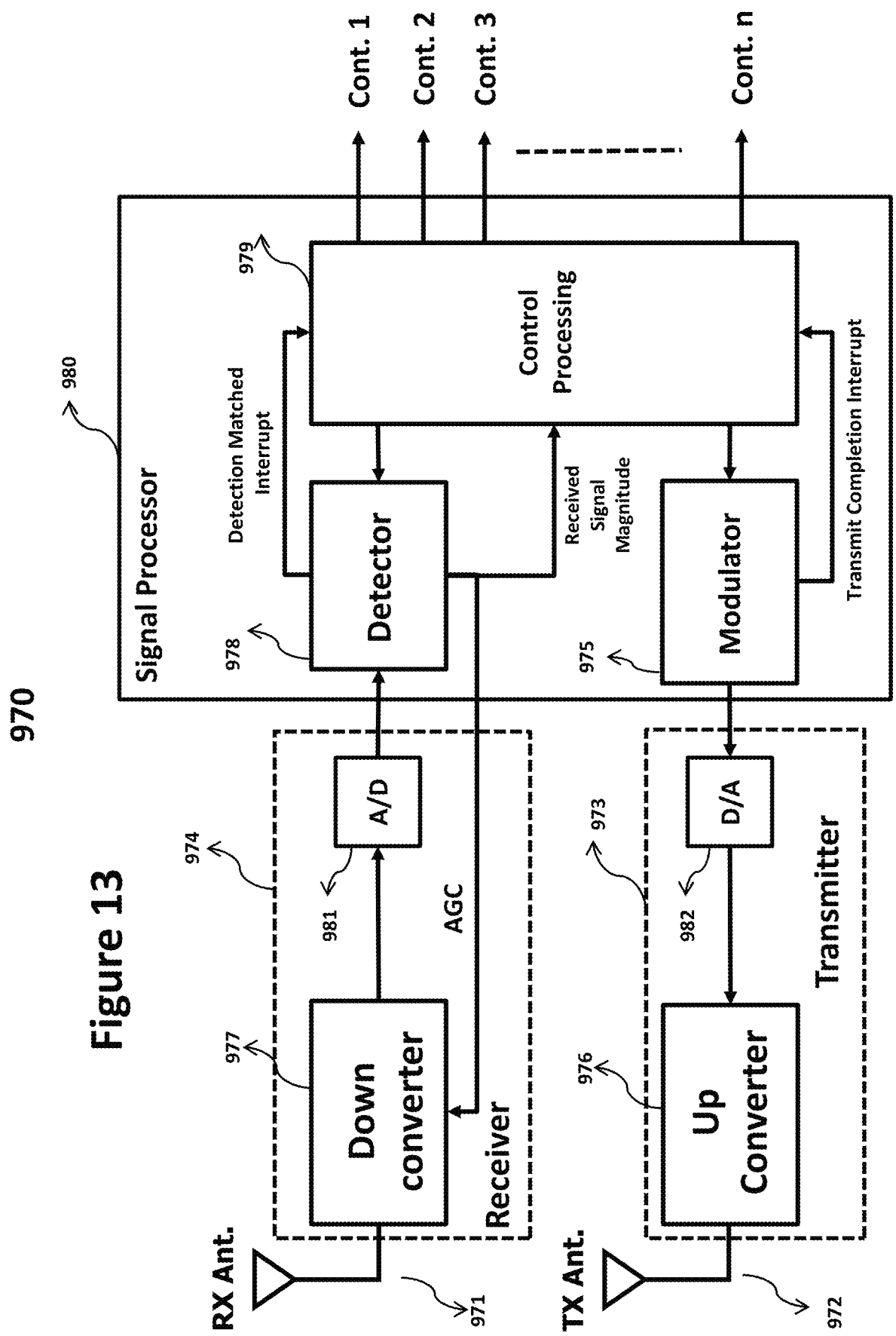
FIG. 13 depicts an embodiment of a wireless sensing system

FIG. 13 depicts an embodiment of wireless sensor system 970 (or IoT device 300, 400, and 500). In general, wireless sensor system 970 (or IoT device 300, 400, and 500) facilitates estimation and calculation of certain environment's parameters by transmitting a coded signal like a unique IP address (or a broadcast, Ethernet frame or packet) signal generated or selected by a control processor 979 through a modulator 975, a transmitter 973 and antenna 972 and then receiving the attenuated version of reflected coded signal (or a broadcast and Ethernet frame or packet) by an antenna 971, receiver 974 and detector 978. For example, control processor 979 selects an IP address pattern from a pool of IP addresses (or a broadcast and Ethernet frame or packet), send it to modulator 975 for modulation then the modulated signal is sent to transmitter 973 to be converted to analog signal by digital-to-analog (D/A) converter 982 and up converted to carrier frequency by up convertor 976 for transmission through antenna 972. The modulator 975 also sends the time of completion of modulation to control processor 979. Then the reflected transmit (a broadcast or an Ethernet frame or packet) signal from an object in the environment is received by antenna 971 and receiver 974, where it is down converted by down convertor 977 and converted to digital signal by analog-to-digital (A/D) converter 981. The digitized received signal is processed in signal processing unit 980, where it is detected by detector 978 and detection time is sent to control processor 979. The digitized down converted received signal also facilitates measurement of received signal strength intensity (RSSI) to provide to control processor 979.

Wireless sensor system 970 (or IoT device 300, 400, and 500) includes, among other things, signal processor 980, transmitter 973, transmit antenna 972, receive antenna 971, and receiver 974.

In one embodiment, signal processor 980, transmit antenna 972, transmitter 973, receive antenna 971, and receiver 974 are components of wireless sensor system 970 (or IoT device 300, 400, and 500) that could be used for various applications. For example, it can be used to communicate with a cellular network (4G, 5G, 6G and beyond), a private network, a WiFi network, transmit and receive a broadcast frame or packet, transmit and receive an Ethernet frame or packet, communicate with the cloud, and etc.

In one embodiment, wireless sensor system 970 (or IoT device 300, 400, and 500) receives information about its surrounding environment which includes various objects and their types from the cellular network (4G, 5G, 6G and beyond), the WiFi network or the private network. Wireless sensor system 970 (or IoT device 300, 400, and 500) also receives an IP address to use for its operation or a pool of IP addresses it can store and use as needed.

In another embodiment, wireless sensor system 970 (or IoT device 300, 400, and 500) uses GPS to obtain time of day, clock synchronization and location coordinates.

In one embodiment, wireless sensor system 970 (or IoT device 300, 400, and 500) uses IEEE1588 and through the cellular network (4G, 5G, 6G and beyond), the WiFi network, the private network, or another wireless sensor system (or IoT device 300, 400, and 500) obtains time of the day and clock synchronization.

In another embodiment, wireless sensor system (or IoT device 300, 400, and 500) 970 uses IEEE1588 PTP to obtain clock synchronization (syncE also can be used for clock synchronization) and time of day from a central CPU controller that it communicates with.

In another embodiment, wireless sensor system (or IoT device 300, 400, and 500) 970 obtains its IP (MAC) address from a central CPU controller that it communicates with.

In another embodiment, wireless sensor system 970 (or IoT device 300, 400, and 500) receives an absolute time for its activity such as transmission, reception, communication and broadcasting from the cellular network (4G, 5G, 6G and beyond), the WiFi network, the private network, or the central CPU controller that it communicates with.

In one embodiment, wireless sensor system 970 (or IoT device 300, 400, and 500) communicates its information and parameters to the cellular network (4G, 5G, 6G and beyond), the WiFi network, the private network, or the central CPU controller that it communicates with.

In one embodiment, wireless sensor system 970 (or IoT device 300, 400, and 500) receives an information data from its surrounding environment which is updated in real time from the cellular network (4G, 5G, 6G and beyond), the WiFi network, the private network, or the central CPU controller that it communicates with.

In one embodiment, wireless sensor system 970 (or IoT device 300, 400, and 500) broadcasts its information data to other wireless sensors (or IoT devices) that belong to various moving or stationary objects in its surrounding environment.

In another embodiment, wireless sensor system 970 (or IoT device 300, 400, and 500) fragments its transmit signal to two or more fragment signals, transmits each fragment signal and receives the reflection of each fragment signal from various objects in its surrounding environment before transmission and reception of next fragment signal.

In one embodiment, wireless sensor system 970 (or IoT device 300, 400, and 500) supports WiFi, Bluetooth, Zigbee or any other over the air protocol as well as physical layer.

In another embodiment, wireless sensor system 970 (or IoT device 300, 400, and 500) is used for other applications and transmits and receives Ethernet frames over the air.

In one embodiment, signal processor 980 that processes both transmit and receive signals comprises of control processor 979, modulator 975, and detector 978.

Signal processor 980 processes an information data transmitted from transmitter 973 through antenna 972 and an information data received from receiver 974 through receive antenna 971. The signal processor 980 also provides gain control for receiver and facilitates change of transceiver operating frequency, channel, and modulation. Signal processor 980 typically utilizes appropriate hardware and software algorithm to properly process the information data.

Wireless sensor system 970 (or IoT device 300, 400, and 500) can be any wireless transceiver that is able to wirelessly transmit communication signals. Wireless sensor system 970 (or IoT device 300, 400, and 500) is disposed on any physical platform that is conductive to effectively transmit the signals.

In one embodiment, communications through wireless system 970 (or IoT device 300, 400, and 500) are by a transmit antenna 972 and a received antenna 971. Transmit and receive antennas are physically separated to provide sufficient isolation between transmit and receive antennas. The transmit antenna 972 and the received antenna 971 can also be common or one antenna.

In one embodiment, communication through wireless system 970 (or IoT device 300, 400, and 500) is by a single antenna. In general at any specified period of time the antenna is selected by a switch and/or a circulator.

Signal Processor 980 has a variety of functions. In general, signal processor 980 is utilized for signal processing, calculation, estimation, activities, methods, procedures, and tools that pertain to the operation, administration, maintenance, and provisioning of wireless sensor system 970 (or IoT device 300, 400, and 500). In one embodiment, signal processor 980 includes a database that is used for various applications. The database can be utilized for analyzing statistics in real-time.

Signal processor 980 also has a variety of thresholds. In general, signal processor 980 provides controls to various components that are connected to it. Moreover, signal processor 980 is a high capacity communication facility that connects primary nodes.

In one embodiment, the wireless sensors system 970 (or IoT device 300, 400, and 500) uses microwave, or mill metric (from 10 GHz to 80 GHz or higher frequencies) wave transceiver.

In one embodiment, wireless sensor system 970 (or IoT device 300, 400, and 500) is controlled by control processor 979. The control processor 979 controls a transmit signal duration and number of times the transmit signal is transmitted. Control processor 979 also coordinates the transmit time and receive time period.

In one embodiment, the wireless sensor system 970 (or IoT device 300, 400, and 500) can be used for body armors, automobile, robots, drone, and any other stationary and moving equipment.

Figure 14A:
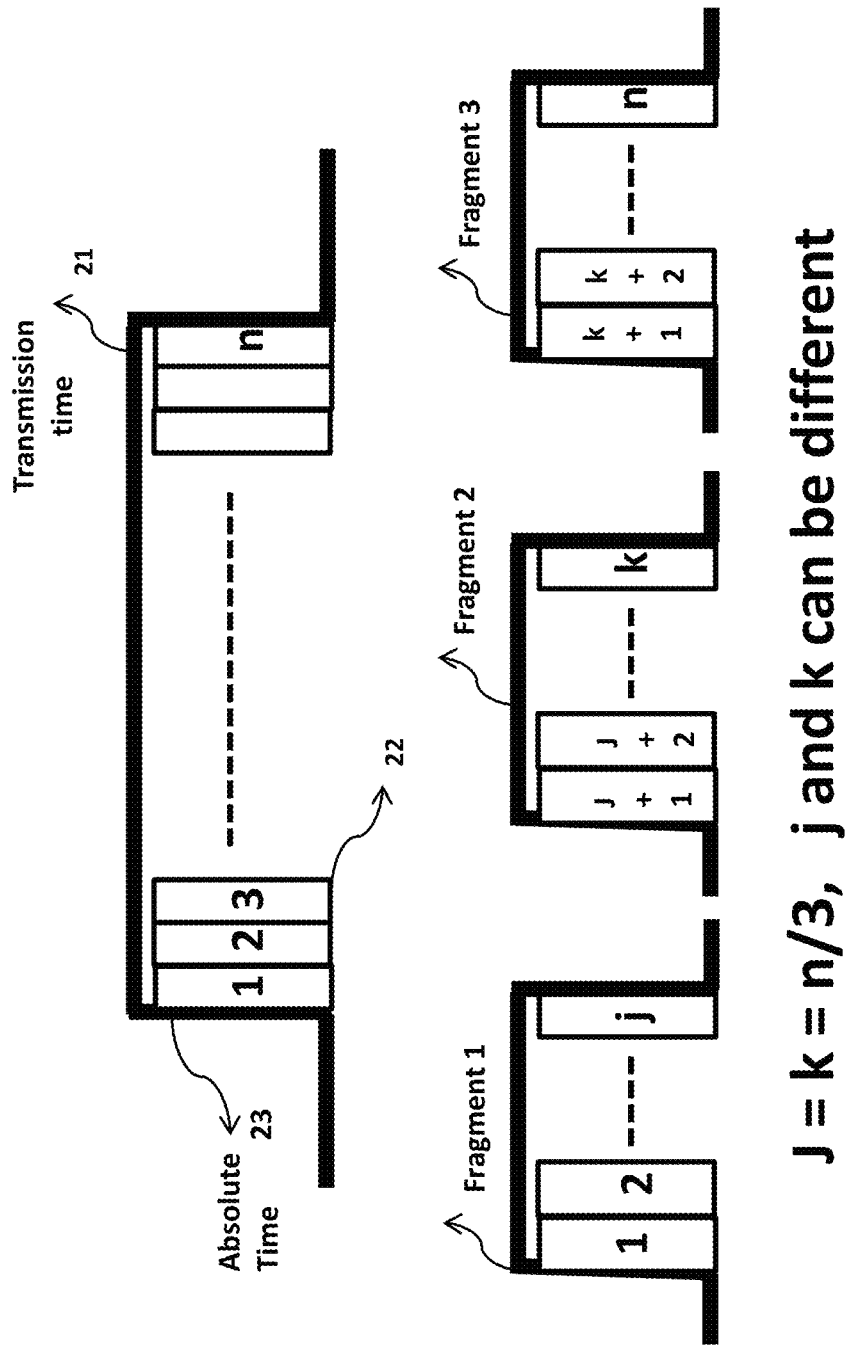

FIG. 14A depicts an embodiment of transmit signal for wireless sensor system 970 shown in FIG. 13 (or IoT device 300, 400, 500, and 600 shown in FIGS. 3, 4, 5 and 6). The transmit signal has a transmission time (duration) 21 and a bit pattern 22. Pattern 22 can be a unique identity code, a unique IP address, random pattern, an entire broadcast frame or packet, and an entire Ethernet frame or packet which is generated by control processor 979.

In one embodiment of wireless sensor system 970 used in a NPS of a moving or flying vehicle/object defined in FIGS. 11 and 12, the pattern 22 is assigned to wireless sensor system 970 (or IoT device 300, 400, 500, and 600) at manufacturing when it is used for ranging.

In one embodiment of wireless sensor system 970 (or IoT device 300, 400, 500, and 600), the random pattern 22 (when it is used for ranging) may be changed after being used a few times based on the artificial intelligence algorithm in the controller 979. The change of transmit pattern 22 signal is for avoiding any collision or false detection from other signals in the surrounding environment.

In one embodiment of wireless sensor system 970 (or IoT device 300, 400, 500, and 600), the transmit signal 22 (when it is used for ranging) is an IP address (or identity code) unique to a NPS using the wireless sensor 970 (or IoT device 300, 400, 500, and 600). The IP address (or identity code) can be assign to wireless system 970 (or IoT device 300, 400, 500, and 600) at manufacturing. The IP address (or identity code) can also be assign to wireless sensor system 970 (or IoT device 300, 400, 500, and 600) in the field by the user. The IP address can be assigned each time the wireless sensor system 970 (or IoT device 300, 400, 500, and 600) transmits and performs ranging. The IP address (or identity code) can also be taken from a pool of IP addresses (or identity codes) stored in the control processor 979 (or IoT device 300, 400, 500, and 600) memory or a removable memory card which can be similar to a subscriber identity module (SIM) card.

In one embodiment of wireless sensor 970 (or IoT device 300, 400, 500, and 600), the transmit pattern duration 21 depends on the number of bit pulses in the transmit signal pattern, carrier frequency, bandwidth, and modulation level. The higher the number of bits in transmits identity code, IP address, random pattern, or broadcast (Ethernet) frame or packet the longer the transmit signal duration.

In one embodiment of wireless sensor 970 (or IoT device 300, 400, 500, and 600), the number of bits in the pattern 22 defines the accuracy of the receiver detection (when it is used for ranging).

In another embodiment, the transmit bit pattern 22 is fragmented to smaller bit patterns, shown in FIG. 14A, to allow use of lower carrier frequency, less bandwidth, or lower level modulation.

In one embodiment, wireless sensor system 970 (or IoT device 300, 400, 500, and 600) transmits the first fragment with "j" bits, receives the reflected transmit signal from objects in surrounding environment of wireless sensor system 970 (or IoT device 300, 400, 500, and 600), then transmit the second fragment with "k-j" bits, and finally transmits the last fragment with "n-j-k" bits and receives the reflected transmit signal from objects in surrounding environment of wireless sensor system 970 (or IoT device 300, 400, 500, and 600) for detection of the transmit bit pattern.

In another embodiment, the fragment bit patterns can have equal number of bits, or different number of bits.

In one embodiment of wireless sensor system 970 (or IoT device 300, 400, 500, and 600), the start of transmission time 21 or start of first bit in bit pattern 22 is an absolute time 23 configured in the controller. This absolute time is derived from time of day wireless sensor system 970 (or IoT device 300, 400, 500, and 600) obtains from GPS receiver, a cellular network (4G, 5G, 6G and beyond), a WiFi network, a private network, or a central controller that it communicates with. The absolute time can also be sent to wireless sensor 970 (or IoT device 300, 400, 500, and 600) by the cellular network (4G, 5G, 6G and beyond), the WiFi network or the private network. The absolute time can be first microsecond in a millisecond, or the nth microsecond after the start of a millisecond.

In addition to absolute time the cellular network (4G, 5G, 6G and beyond), the WiFi network or the private network assigns to the wireless sensor 970 (or IoT device 300, 400, 500, and 600) a time slot that starts from the absolute time and has a duration which is equal for all objects that use wireless sensor 970 (or IoT device 300, 400, 500, and 600) in the environment. The time slot duration assigned to the objects using wireless sensor 970 (or IoT device 300, 400, 500, and 600) can also be different.

In one embodiment, the absolute time can be any nanosecond within a microsecond period, such as $1^{st}$ nanosecond, kth nanosecond, nth nanosecond, and etc.

In one embodiment of wireless sensor 970 (or IoT device 300, 400, 500, and 600), the time of day obtained from GPS receiver or from the 4G, 5G, 6G, the WiFi network or the private network using IEEE1588 has accuracy within a few nanosecond, fraction of microsecond, or fraction of nanosecond.

In one embodiment the time of day obtained from GPS receiver or from the 4G, 5G, 6G, the WiFi network or the private network using IEEE1588 is based on Coordinated Universal Time (UTC).

In another embodiment, an absolute time used for broadcasting by wireless sensor 970 (or IoT device 300, 400, 500, and 600) in the smart environment 700 and 800 defined in FIGS. 7 and 8 helps to avoid any collision when various objects broadcast their information.

Figure 14B:
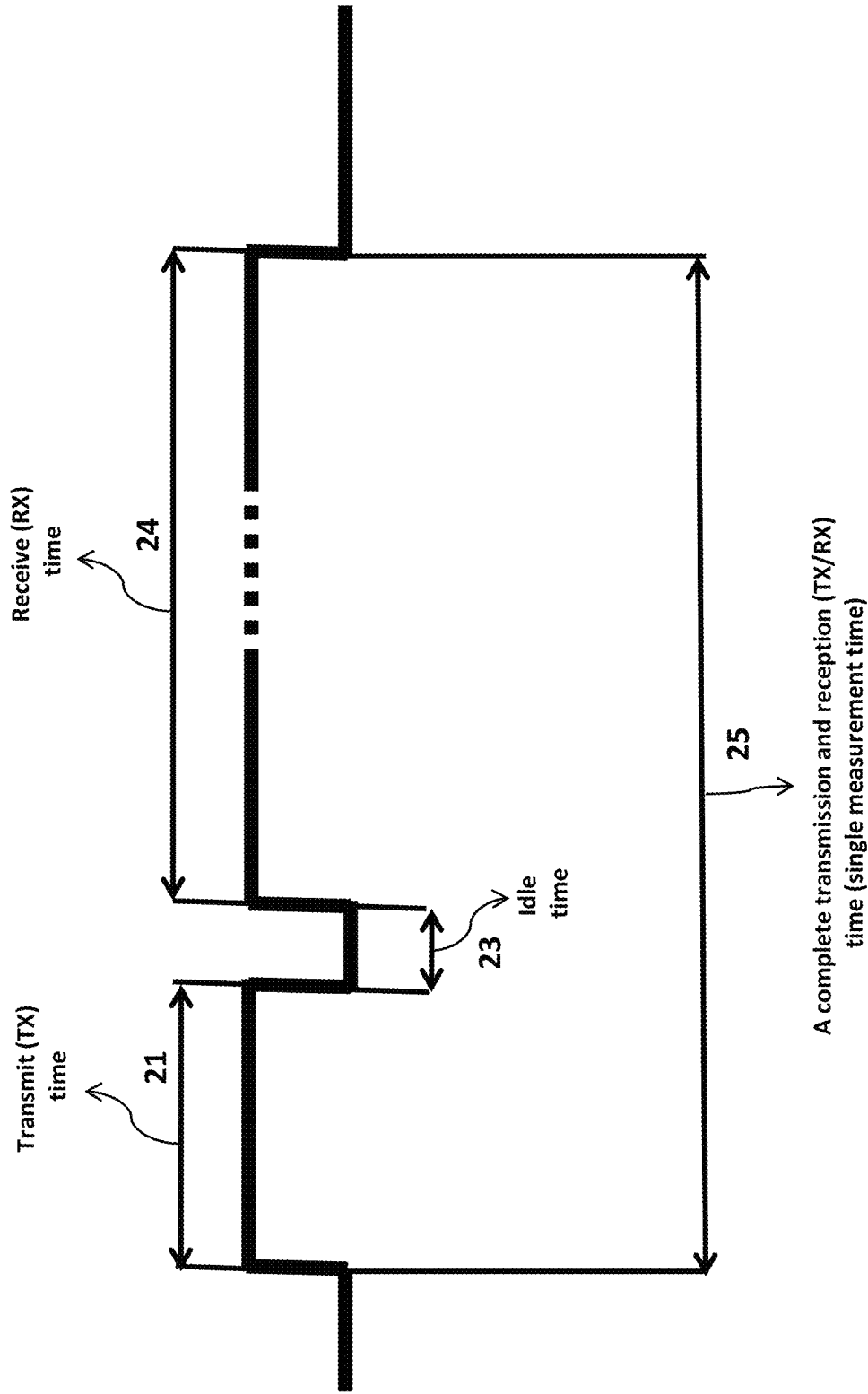

FIG. 14B shows the duration of a complete single transmission and reception (single measurement time) 25 for wireless sensor system 970 (or IoT device 300, 400, 500, and 600) when it is used for ranging. The complete transmission and reception duration comprises of the transmit time (duration) 21, idle time (duration) 23 and receive time (duration) 24.

In one embodiment of wireless sensor system 970 (or IoT device 300, 400, 500, and 600), the idle time 23 is zero. The idle time can vary based on proximity of an object to wireless sensor system 970 (or IoT device 300, 400, 500, and 600) in its surrounding environment. The closer the object the smaller the idle time 23 is. In most circumstances the idle time is zero and after completion of transmission the wireless sensor system 970 (or IoT device 300, 400, 500, and 600) start its reception.

In one embodiment of the wireless sensor system 970 (or IoT device 300, 400, 500, and 600), the receive time 24 depends on the monitoring radius of surrounding environment of the wireless sensor system 970 (or IoT device 300, 400, 500, and 600). The bigger the radius of monitoring the longer the reception time of wireless sensor system 970 (or IoT device 300, 400, 500, and 600) is. Therefore, the assigned time slot for a complete transmission and reception depends on the monitoring radius.

In another embodiment, when the wireless sensor system 970 (or IoT device 300, 400, 500, and 600) is used to transmit and receive broadcast or Ethernet packets the time slot duration depends on three parameters. One is maximum length of a packet allowed for both broadcast and Ethernet packet. Second is the monitoring radius, and the third is error in time of day that is used to derive absolute time. In real operation it is rare to have time of day error more than 100 nanosecond and monitoring radius is usually less than 30 feet which is equivalent to 30 nanoseconds. The time of day (TOD) is also updated regularly which eliminates accumulation of time of day error. Therefore, time slot duration of 2 microseconds is sufficient for broadcast and Ethernet packets of an object in a smart environment when a 70 GHz to 80 GHz band is used. This allows to assign one thousands absolute time with a time slot duration of 2 microsecond within two millisecond. Each object is assigned one or more time slot with its associated start time that is the absolute time.

Figure 14C:
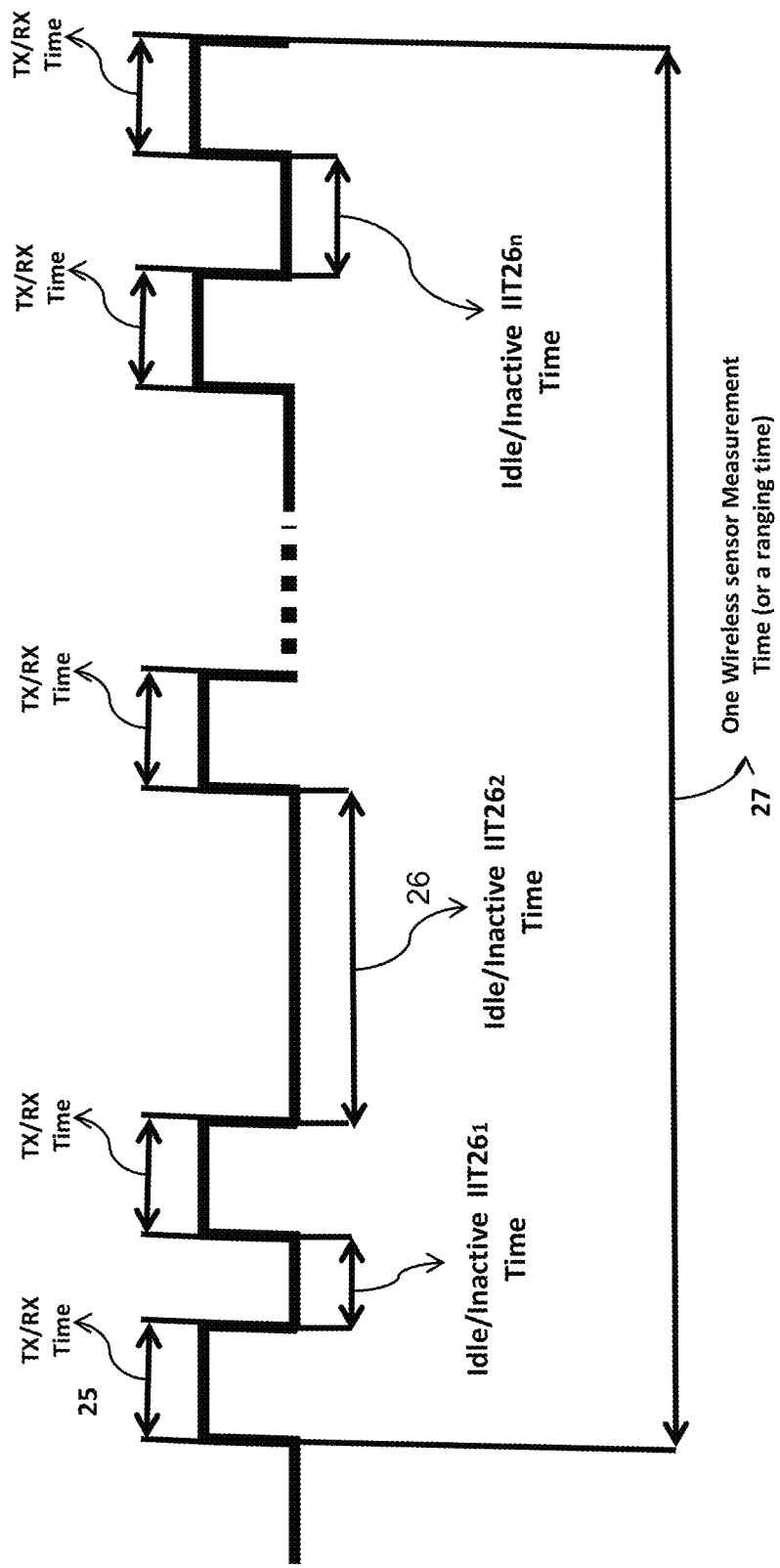

FIG. 14C shows the duration of a complete measurement time 27 of wireless sensor system 970 (or IoT device 300, 400, 500, and 600) when used for ranging. It comprises of "n+1" single complete transmission and reception (single measurement) times 25 and the idle/inactive times $IIT26_1$ to $IIT26_n$ between single complete transmission and reception (single measurement) times.

In one embodiment of the wireless sensor system 970 (or IoT device 300, 400, 500, and 600), idle/inactive times $IIT26_1$ to $IIT26_n$ can have the same duration or randomly different duration based on artificial intelligence algorithm assessments. Artificial intelligence algorithm within wireless sensor system 970 (or IoT device 300, 400, 500, and 600) control processor or control processor of a NPS that uses the wireless sensor 970 (or IoT device 300, 400, 500, and 600) defines the idle/inactive time duration to avoid any reception collision with transmit signals from other objects in the surrounding environment of the wireless sensor system 970 (or IoT device 300, 400, 500, and 600).

In one embodiment of the wireless sensor system 970 (or IoT device 300, 400, 500, and 600), the artificial intelligence algorithm within the control processor of wireless sensor system 970 or control processor of a NPS that uses the wireless sensor can use a number of measurement times 27 for assessment of the surrounding environment before deciding to activate any function or devices.

FIG. 14D depicts the duration of a time slot 31 used for ranging and communication/broadcast/Ethernet/monitoring by the wireless sensor system 970 (or IoT device 300, 400, 500, and 600). The time slot 31 comprises of guard time (1) 32, ranging time 33, guard time (2) 34, communication/monitoring/broadcast/Ethernet time 35, and guard time (3) 36. The start of time slot is the absolute time 30 assigned to a wireless sensor system 970 (or IoT device 300, 400, 500, and 600) or NPS of an object. Time slot 31 can be all assigned to monitoring task, communication task, transmission/reception of broadcast packet task, transmission/reception of Ethernet packets task, or ranging task. Time slot 31 can also be assigned to two tasks, three tasks, four tasks or all five tasks.

The guard times at the beginning and end of the time slot is to avoid any overlap between two adjacent time slots and tasks. Although IoT devices obtain their time of day (TOD) from eNodeB, or gNodeB of 5G, 6G, 7G, WiFi, or private IoT network but it is possible that their TOD are different with reasonable error. The error does not accumulate because the TOD is updated on regular basis. The start and end guard time should be bigger than the highest error in TODs. The guard time between ranging time and the time of other tasks is to avoid overlap and time for processing of data.

In another embodiment, the cellular network (4G, 5G, 6G, 7G and beyond), the WiFi network or the private network shares with each wireless sensor system 970 (or IoT device 300, 400, 500, and 600) in a smart environment the absolute time and time slot of all the registered wireless sensor system 970 (or IoT device 300, 400, 500, and 600) in the smart environment. All absolute times and time slots are stored in a shared database and are managed by a shared operation and management center (SOMC) used by all service providers and operators.

During the time slot the IoT device's wireless channel should not change. The maximum time that a channel is constant and does not change is "coherence time" and the maximum channel bandwidth that the fading is flat is "coherence bandwidth".

Coherence bandwidth is proportional to average channel delay spread. If average delay spread is larger than symbol time then the channel experiences frequency selective fading which results in inter symbol interference (ISI). To avoid selective fading or ISI the symbol time should be larger than average delay spread. Therefore, if the symbol time is $T_s$ and the average delay spread is $C$ then we need to meet the following condition;

$Ts > C$ or $1/Ts < 1/C$ or $Bs < Bc$

Where Bs is symbol or channel bandwidth, and Bc is the coherence bandwidth.

Coherence time is proportional or related to Doppler frequency shift or change. When IoT ranging device is moving with respect to the object in the smart environment or both IoT ranging device and the object are moving then the frequency of reflected signal from the object changes due to motion. The change in frequency is proportional to the approaching speed of the object towards the IoT ranging device. If the carrier frequency is $F_c$ and approaching speed of object towards the IoT ranging device is V then the Doppler shift $F_d$ is;

$F_d = V \cdot F_c / V_l$, where $V_l$ is velocity of light in free space. The coherence time $T_c$ is the time channel is approximately constant. $T_c$ is related to Doppler shift by following equation;

$T_c = \frac{1}{4} \cdot F_d$

The ranging pattern for wireless sensor (IoT ranging device 300, 400, 500, 600) shown in FIG. 14A can have two different structures. In one structure the pattern comprises of the ranging pattern only. In a second structure the ranging pattern comprises of a synchronization (preamble) pattern followed by ranging pattern. In first structure ranging pattern is used for both synchronization and ranging. Using a synchronization pattern reduces resolution of detection. If the length of pattern is reduced then probability of false detection increases. In order to increase the resolution without reducing the length of the ranging pattern higher channel bandwidth needs to be used. However, higher channel bandwidth requires higher carrier frequency, smaller delay spread and lower relative speed or approaching speed in order to avoid violation of coherence bandwidth and coherence time. Lower delay spread limits the radius of ranging and lower approaching speed or relative speed limits the speed objects can move in a smart environment.

One way to overcome the above problem is to converts the ranging pattern into smaller segments. The IoT ranging device or wireless sensor transmit each segment of ranging pattern signal then receives the reflected segment followed by transmission of the second segment and remaining segments similar to first segment. Depending on application one can use the zero or more segments as synchronization (preamble) segment of ranging pattern.

Let's assume thes maximum speed of moving object is 100 miles/hour then every millisecond the object moves 4.5 centimeter. If two objects in smart environment moving towards each other with 100 miles/hour then every millisecond they get closer about 9 centimeter and every 3 millisecond around one foot. Therefore, if the two objects are 3 meters apart and their approaching speed towards each other is 200 miles/hour then they collide after 33 milliseconds. This time is sufficient for a navigation and protection system (NPS) to obtain required information data, to make a decision and to activate appropriate devices and functions in order to avoid a collision.

Let's assume the radius for ranging and monitoring (sending broadcast and Ethernet packets and receiving broadcast and Ethernet packets) is 3 meters. In this scenario IoT device is used for ranging and monitoring by moving objects (automobile, robots, etc.) and stationary objects in smart environment. If the IoT device is connected to external body of moving object and stationary object then for a radius of 3 meters average delay spread should not exceed 4 nanoseconds (IoT device uses direction antenna with narrow radiation pattern to avoid higher delay spreads). IoT device ignores received signals (reflected, broadcast, Ethernet) that are from objects at a distance more than three meter by measuring the RSSI of a received signal and compare it with a table of RSSI versus distance or uses TOD of transmission and reception of ranging signal.

Four nanosecond delay spread corresponds to 250 MHz coherence bandwidths. As long as IoT device bandwidth is less than 250 MHz the channel only experiences flat fading across the channel bandwidth. This bandwidth corresponds to a symbol time of higher than 4 nanosecond or symbol rate of less than 250 Mega symbol per second. If IoT device uses QPSK (quadrature phase shift keying) modulations then the bit rate should be less than 500 mega bits per second (Mbs).

Two hundred miles per hour relative or approaching speed for a carrier frequency of 1 GHz corresponds to 296 Hz Doppler Shift which results in a coherence time of 844 microseconds. When time slot 31 or 41 is used for both ranging and transmission of broadcast packet, 1 GHz carrier frequency is not high enough to provide an acceptable ranging resolution. An acceptable resolution (approximately 4 feet or 4 nanosecond) using a simple IoT ranging device requires a symbol time of approximately 4 nanosecond or a symbol rate of 250 MHz. Using QPSK modulation the 250 MHz channel supports 500 Mbs (mega bits per second). QPSK modulation also requires simple hardware and software at higher carrier frequency. Carrier frequencies that support channels with 250 MHz bandwidth should be from higher frequency band assigned to 5G, 6G, beyond 6G and WiFi. Carrier frequency should not be very high in order to avoid lower coherence time.

A suitable frequency band for the time slot assigned to an IoT device that performs ranging and transmission of broadcast and Ethernet packet is 28 GH. The Doppler shift at 28 GHz is 296×28=8.288 KHz which results to 30 microsecond coherence time which is more than sufficient for a time slot. Therefore, for a 10 microsecond time slot that supports ranging, guard times and broadcast/Ethernet/communication time, a 250 MHz channel bandwidth only experiences flat fading and does not change with time.

Since time of day (TOD) is obtained from a very accurate source one microsecond guard time is sufficient to avoid an overlap of time slots. The time assigned to ranging time could be as much as 2 microseconds. When 25 nanoseconds assigned to a complete transmission and reception of a symbol using QPSK, a 2 microsecond ranging time supports 80 segments of 2 bits (one QPSK symbol). If ranging pattern is 20 bits then during 2 microseconds ranging time 8 complete ranging can be performed. In summary, Carrier frequency=28 GHz and Relative speed or approaching speed=200 miles/hour Results in a Doppler shift=8288 Hz or coherence time of 30 microsecond.

Delay spread=4 nanosecond results in a coherence bandwidth=250 MHz

Using QPSK, 250 MHz channel bandwidth supports 500 mega bits per second (Mbs).

Assigning 10 microseconds for each time slots allows for 300 independent time slots in 3 millisecond period during which the objects move one foot closer to each other.

FIG. 14E depicts the duration of a time slot 41 used for ranging and communication/broadcast/Ethernet/monitoring by the wireless sensor system 970 (or IoT device 300, 400, 500, and 600). The only difference between FIGS. 14E and 14D is that ranging is performed before end of time slot 41 and everything else is the same.

In another embodiment, wireless sensor system 970 (or IoT device 300, 400, 500, and 600) is aware of the absolute times and time slot durations (if time slot durations are different) assigned to all other wireless sensor systems 970 (or IoT device 300, 400, 500, and 600) in its smart environment.

In another embodiment, all wireless sensor systems 970 (or IoT device 300, 400, 500, and 600) in a smart environment are registered with one or more cellular networks (4G, 5G, 6G, 7G and beyond), WiFi networks or private networks that are linked and share, control and manage the information (absolute times, time slot duration, function, type, location, time of day and etc.) received from all wireless sensor systems 970 (or IoT device 300, 400, 500, and 600).

In order for a navigation and protection system (NPS) to operate in all circumstances an artificial intelligent (AI) algorithm is used that receives information data from following source:
1. All internal sensors used by an object.
2. Wireless sensors, Radars, Image sensors, Lidars, laser, and ultrasonic sensors that perform ranging to provide a distance between two objects.
3. Image sensors that also provide the same information as wireless sensor as well as image identification of the objects.
4. IoT devices that in conjunction with IoT network provide a distance an approaching speed of the two objects towards each other using time of day (TOD) time stamps.

AI algorithm requires information data from at least three of the above sources to be able to make a decision. Having access to more than three sources results in a more accurate decision and better support for navigation and activating the most effective devices within protection system.

Figure 14F:
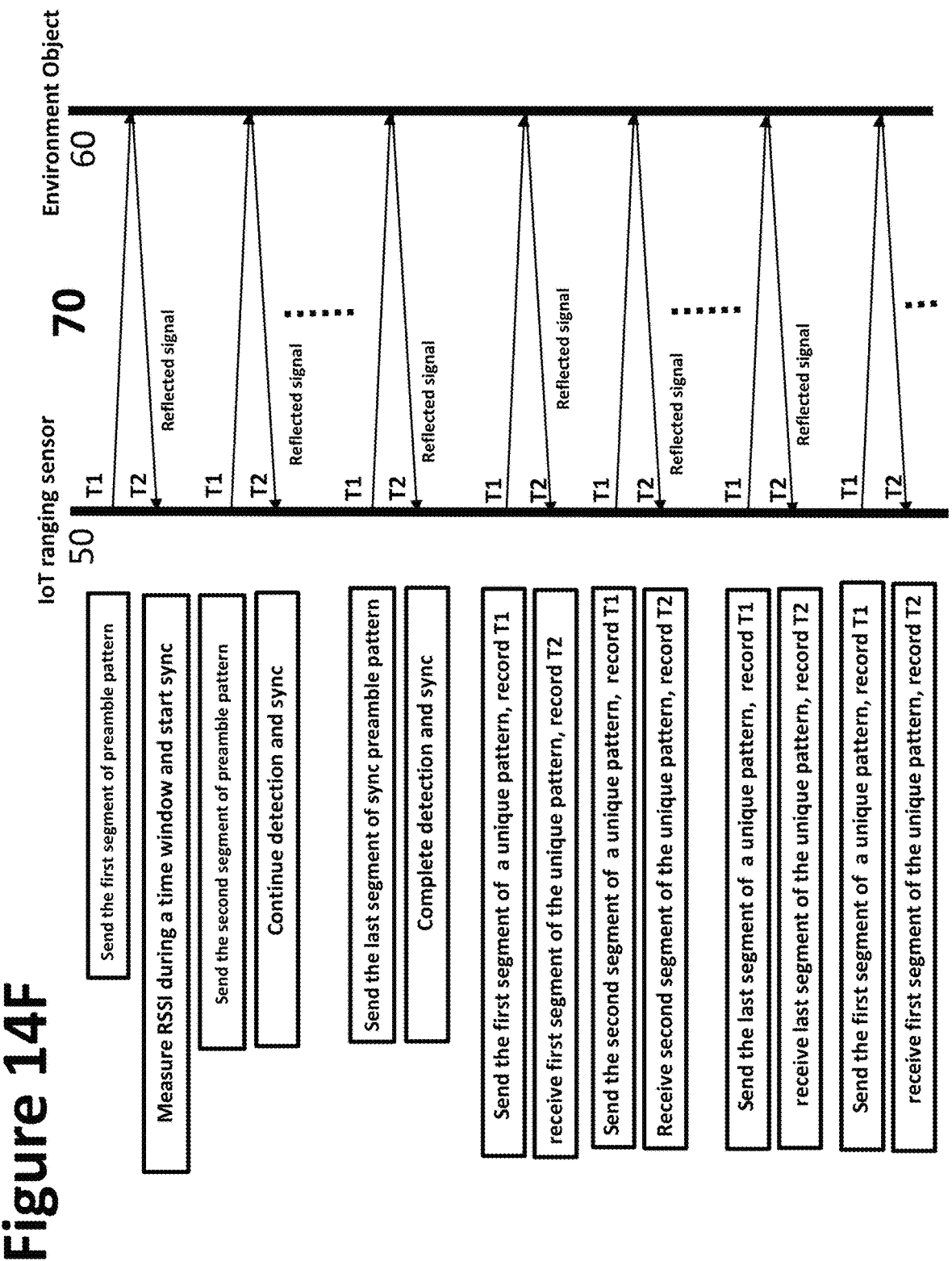
Figure 15A:
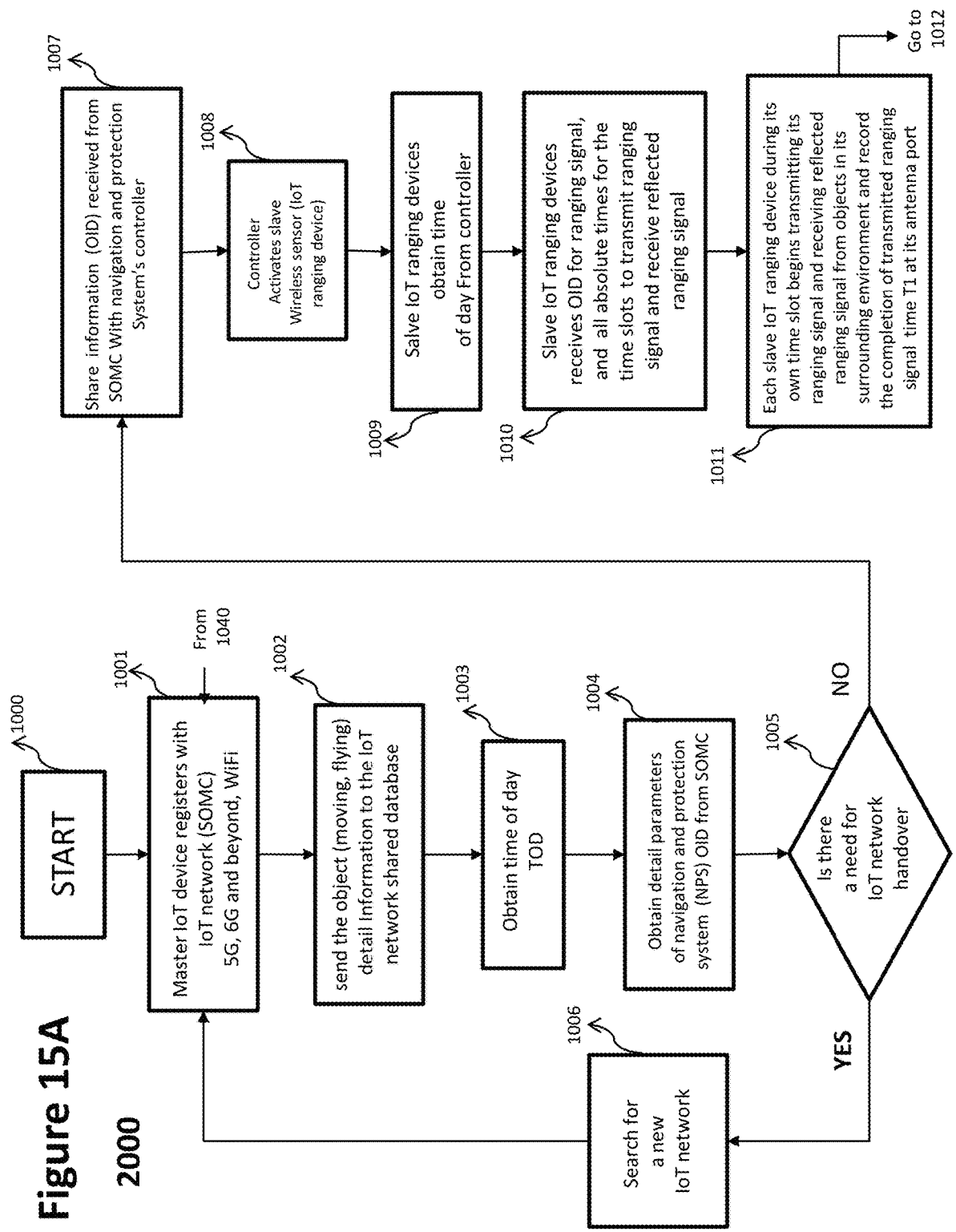
FIGS. 15A through 15D depict the process steps to calculate environmental parameters The drawings referred to in this description should be understood as not being drawn to scale except if specifically noted.
Figure 15B:
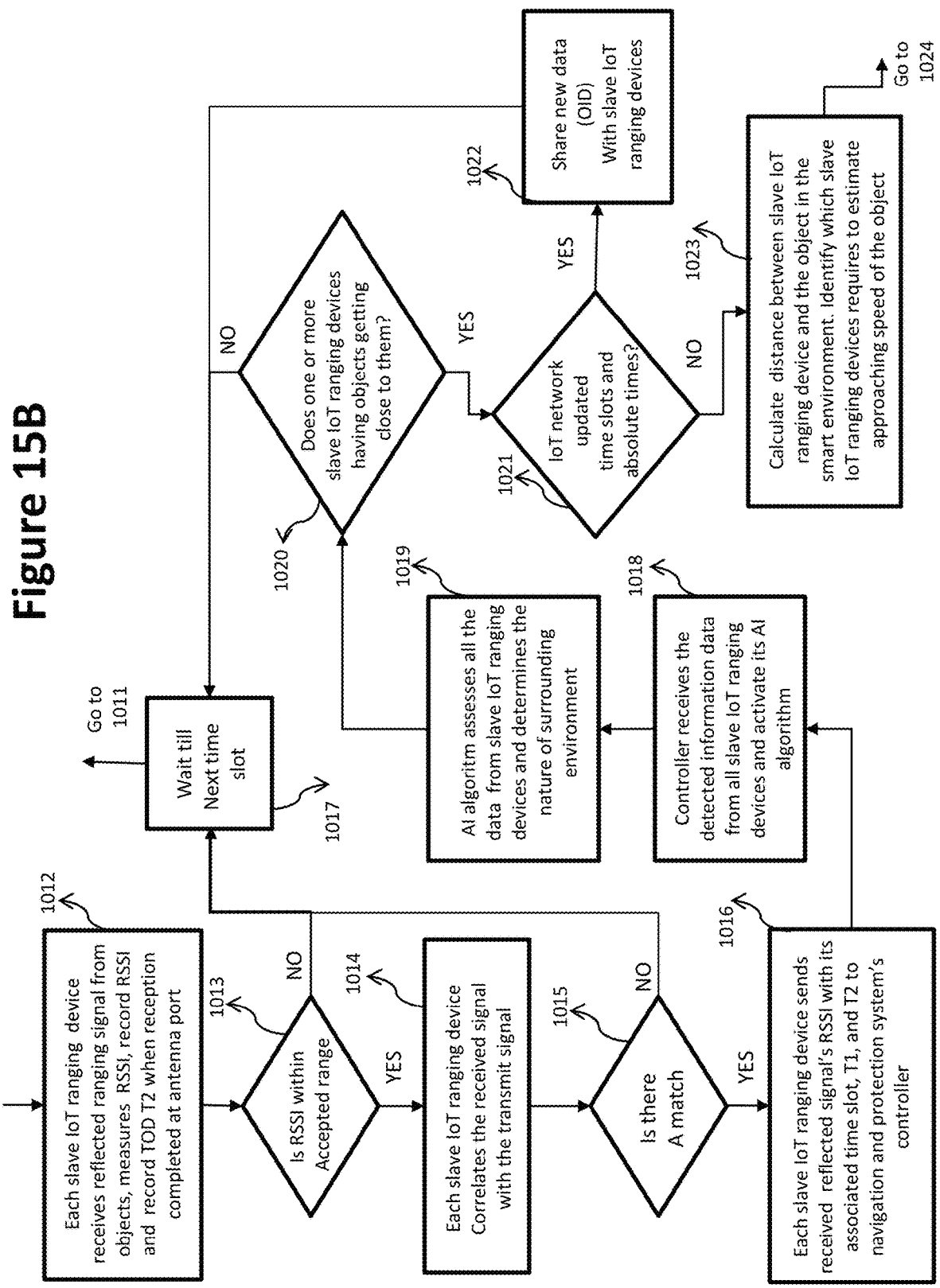
Figure 15C:
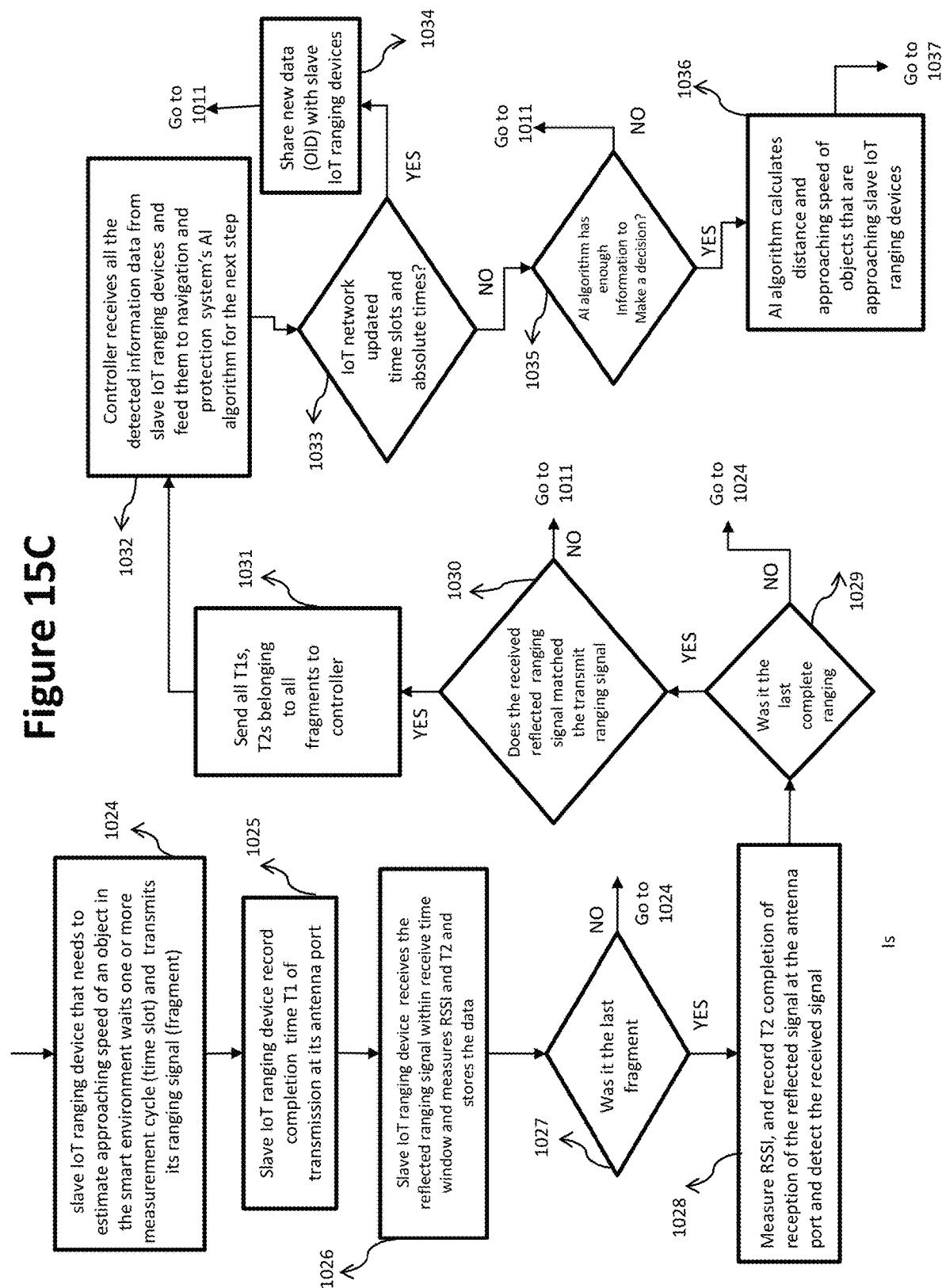
Figure 15D:
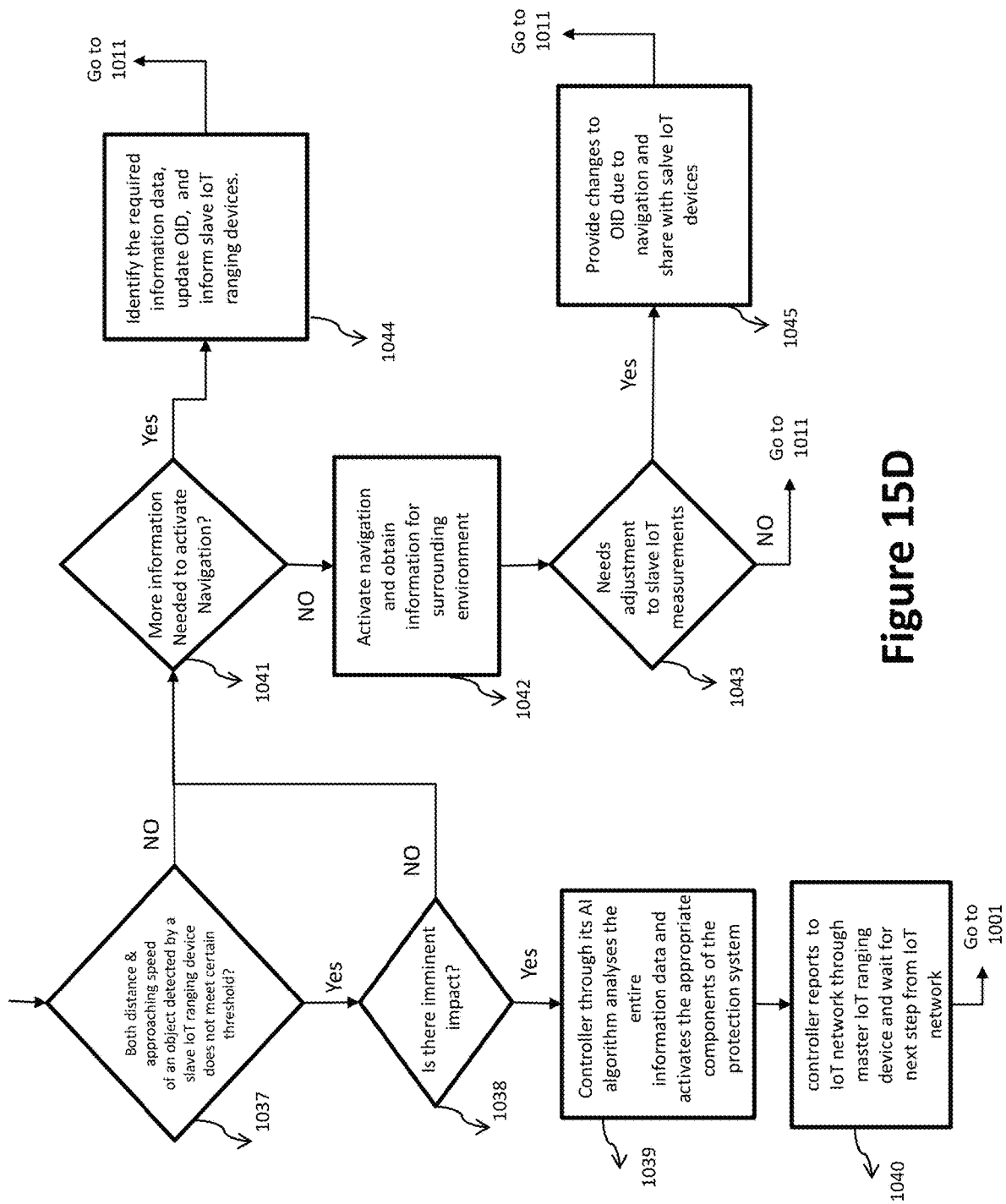

FIG. 14F depict a ranging method 70 for a segmented ranging pattern with preamble. It is also possible to avoid a preamble. Preamble is used to detect any phase rotation of the reflected signal from an object due to channel, the object, and Doppler shift. Since the channel does not change during ranging due to coherence time, once the phase rotation is known then detection of reflected segments becomes very simple. The phase rotation can also be achieved without having preamble. During the first complete ranging the phase rotation can be estimated and used during other complete ranging. It is also possible to use first few symbols of the ranging pattern without preamble to estimate the phase rotation. Once phase rotation is known then the reflected signal can be readily detected. The ranging pattern segments are then transmitted and the reflected signal is received during a period configured by NPS. Each time a fragment is transmitted T1 (by IoT ranging device 50) which is the time transmit segment left the antenna and time T2 when the reflected signal (from object 60) is received at the antenna port are recorded. The reflected signal is only stored for detection if RSSI or propagation time (T2−T1) are within an acceptable range.

Once all the segments have completed transmission and reception with acceptable RSSI then the stored received segments are detected and compared with transmit ranging pattern. If there is a match then last T1 and T2 are used to estimate the propagation time and distance between IoT ranging device 50 and object 60 in the smart environment.

It is possible to improve the resolution of ranging by higher level modulation. However, higher level modulations add to complexity of the receiver and cost of IoT ranging device. The advantage of this technique is that ranging device (Radar, Lidar, IoT ranging, ultrasonic sensor, laser. and/or wireless sensor) operates during a time slot assigned to NPS without experiencing any interference. The only interference is receiver blocking due to other type of unexpected interferences if any exist. An object may use multiple ranging devices at different location of the object. In this scenario it is possible to have all ranging devices operate at the same time slot assigned to the object without any interference. Therefore, an object is assigned a time slot starting at an absolute time and the object can use several ranging devices (Radar, Lidar, IoT ranging device, IoT broadcasting, ultrasonic sensor, laser, or wireless sensor) operating at the same time slot. An object may use two or more type of ranging devices at different location of the object for ranging.

If the assigned ranging time can accommodate more complete single ranging then for more accuracy it is possible to repeat the ranging as many times as possible in the assigned ranging time. It is also possible to use FMCW (frequency-modulated continuous-wave), CW (continuous wave), pulsed Radar, or Lidar for ranging during ranging time where the reflected signal's chirp frequency is used to estimate the distance between IoT ranging device and an object in the smart environment. Using this technique assures that during ranging there is no interference because no other object in the environment is allowed to transmit during a time slot assigned to an object. As mentioned earlier the entire time slot can be assigned to ranging. It is also possible to use two or more methods of ranging (IoT ranging, Radar, Lidar, Image sensor ranging, ultrasonic ranging, and broadcast time stamp method 930 shown in FIG. 10D) during the time slot assigned to an object.

FIGS. 15A through 15D depict an embodiment of a process 2000 for using an IoT device (wireless sensor system 970 or IoT device 300, 400, 500, and 600, Radar, and Lidar, ultrasonic sensor, and laser) by an object to estimate and calculate environmental parameters. The distance can be measured accurately if the IoT device (wireless sensor system 970 or IoT device 300, 400, 500, and 600, Radar, ultrasonic sensor, laser, and Lidar) operates in an environment that have low average delay spread or high coherence bandwidth. Therefore, the process 2000 requires to limits its ranging radius for low average delay spread. Average delay spread depends on the ranging distance and elevation of the IoT ranging device from the ground. As explained before for moving objects like automobiles, trucks, robots and stationary objects a 3 meters ranging radius and an elevation of less than 2 meters results in an average delay spread of 4 nanosecond. This average delay spread allows the IoT ranging device uses a ranging signal with approximately 250 MHz bandwidth. Higher bandwidth results in higher ranging resolution. However, higher bandwidth requires higher carrier frequency which needs lower delay spread in order to avoid inter symbol interference (ISI). Therefore, for an optimum solution ranging radius, average delay spread, ranging signal bandwidth, relative speed of two objects and carrier frequency need to be considered and chosen for best and reliable operation.

One parameter that may be very useful for the IoT ranging device is the receive signal strength intensity (RSSI). IoT ranging device's receiver measures the RSSI and T2 (the time day TOD the reflected signal with highest RSSI arrived) of received reflected ranging signal after the completion of transmission of ranging signal at time of day T1. If T2−T1 (which is proportional to distance between IoT ranging device and the object) is within the ranging radius then the signal is detected.

In various embodiments, the process 2000 is carried out by processor and electrical circuit under the control of a processes or executable instructions. The readable and executable instructions reside, for example, in a data storage medium such as processor usable volatile and non-volatile memory. However, the readable and executable instructions may reside in any type of processor readable storage medium. In some embodiments, the process 2000 is performed at least by one of the circuits described herein.

A moving or flying object may use multiple IoT devices (wireless sensor system 970 or IoT device 300, 400, 500, 600, Radar, ultrasonic sensor, laser, and Lidar) as shown in FIGS. 11 and 12 to monitor its surrounding environment as well as other sensors and monitoring devices that are used internal or external to the object. In this case IoT device 904 or 944 acts as a master and is used to communicate, register, receives information data, transmit information data, obtain time of day (TOD) and synchronize to an IoT network (4G, 5G, 6G, 7G, and WiFi). The master IoT device 904 or 944 also shares the information data it receives from the IoT network with other slave IoT devices, wireless sensors, ranging devices, and monitoring devices (901$_1$ to 901$_i$). All IoT devices including the master IoT device monitor the surrounding environment of the object and participate in identifying if a received signal meets the requirements for detection.

The object's navigation and protection system's (NPS's) operation process 2000 is activated at start 1000. The object's navigation and protection system (NPS) shown in FIGS. 11 and 12 comprises of a central controller, a master IoT device, a plurality of slave IoT devices, other internal and external sensors, ranging devices (Radar, Lidar, IoT, laser, ultrasonic) and monitoring devices, protection devices such as multilayer airbags, compressed air tanks with multiple outlets, expandable pads (by applying voltage at two end of the pad), and navigation devices (steering wheel, accelerator, break, alarm, horn, high beam light and etc.). In addition to IoT ranging device mentioned earlier other key sensors are Lidar (light detection and ranging), Radar (radio detection and ranging), wireless sensors for ranging, ultrasonic sensors, laser, and image sensors for ranging and identification of objects in the smart environment.

At 1001 the master IoT device registers with one of the available 5G, beyond 5G, 6G and beyond or WiFi IoT network. The master IoT device can have an account with all the operators that support IoT network or use roaming to be connected at all times. All IoT networks from different service providers or operators share the same data base and operation and management center (SOMC) for the navigation and protection system's operation process 2000. The master IoT device after registering with IoT network shares its location coordinates, and detail information (type, model, dimensions, capabilities, function, specification, etc.) of the object to be stored in shared database in the cloud. The shared operation and management center (SOMC) uses the stored location coordinates of the master IoT devices used by NPSs (that regularly updated in the shared data base) to assign an absolute time and a time slot to master IoT device. The master IoT device shares the absolute time and the time slot with a controller used by NPS. The controller shares the data with all slave IoT devices, and other sensors (Radars, Lidar, wireless sensors, image sensor, laser, and ultrasonic sensors) used by NPS. If the time slot duration is identical for all master IoT devices then each NPS needs its own assigned time slot, absolute time, and number of time slots (or time between an object's two consecutive time slots). If the time slot duration is different for master IoT devices or NPSs then each NPS needs to have all absolute times and the time slot durations assigned to all master IoT devices or NPSs in the smart environment. Master IoT device (a component of NPS) or NPS from assigned absolute times and time slots can calculate the start and end of one measurement cycle transmission (when all objects in the smart environment used their time slot or all the time slots passed) and the start of object's consecutive time slots. It is also possible for SOMC informs the number of consecutive time slots and duration of a measurement cycle (duration total time slots) for all objects in smart environment. This way an objects when used its time slot knows when its next time slot starts. In addition to absolute times and time slots for different activities, shared operation and management center (SOMC) assigns a frequency, a channel, a bandwidth, a modulation method, and an effective radiation power (ERP) to the master IoT devices or NPSs based on their location coordinate. The ERP assigned to NPS is for the slave IoT devices used by NSP. Master IoT device uses an ERP for communication with IoT network specified by the standard body. In general SOMC through master IoT device of NPS controls all activities of slave IoT devices and other sensors (Radar, ultrasonic, and Lidar) used by NPS. Both shared database and SOMC are located in a cloud used by all operators and service providers (IoT networks) through an open interface. The slave IoT devices in process 2000 perform ranging function using a ranging pattern defined earlier. Shared database and SOMC are updated on regular times specified by SOMC. The update information is provided by master IoT device of each object (moving, flying, and stationary) in smart environment. SOMC has divided the entire environment to sub-environment with specified area (triangular, square, hexagonal and other shapes). Each sub-environment is a smart environment. SOMC manages all the sub-environments and the objects within them. The management is two ways. Objects through their master IoT devices send their information data explained above to SOMC. SOMC provide every object with OID that was explained earlier and has information data used by NPS for navigation and protection of the object. SOMC monitors the movement of each object by receiving information data from its master lot device and based on its location and the sub-environment (smart environment) provides an updated OID. Therefore, in a smart environment navigation and protection of an object is controlled by both SOMC and object's NPS. In other words NPS of an object is slave to SOMC that acts as master controller.

An object in smart environment only uses its NPS when all the devices used by NPS are correctly operating and there is proper communication between the object and SOMC for exchange of information data. If SOMC identifies an object's NPS in smart environment does not fully meet all the requirements then that object is prohibited to use NPS for navigation and the object has to use other methods. This needs to be standardizing in order all objects that want to operate in a smart environment meet all requirements of standard.

At 1002 the master IoT device that belongs to a moving, a flying and a stationary object share the information data of their NPS with the IoT network in order to be stored in the shared data base used by the SOMC. The information data consists of the master IoT device's location coordinates, the specification of the slave IoT devices (operating spectrum, operating bandwidth, supported modulations, and ERP capability), type of the object, function of the object, specification (dimensions) of the object, and status of the object (traffic light color). The master IoT device and slave IoT devices require having a minimum specification in order for the object to use its NPS.

At 1003 the master IoT device of NPS obtains the time of day (TOD). The TOD can be obtained from the IoT network (using one of IEEE1588 PTP, unused subcarriers, cyclic prefix), or GPS. TOD can also be obtained from another master IoT device in proximity within the smart environment.

At 1004 master IoT device obtains detail operation information data (OID) for the NPS from SOMC through IoT network. The OID includes frequency, channel, modulation, ERP, absolute times (start of time slot), time slot duration for all objects in the smart environment, and duration of a complete cycle. The start time is a microsecond within millisecond ($1^{st}$, $K_{th}$, $N_{th}$ and etc.). Duration is the time window of time slot assigned to each object for various activities (sensing, ranging, communication, broadcasting, and etc.).

At 1005 master IoT device evaluates if it needs to perform a handover to another of its own IoT network's gNodeB/eNodeB (WiFi router) or to roam to another IoT network. If it requires performing handover or roaming then it goes to 1006.

At 1006 master IoT device search for a new eNodeB/gNodeB (WiFi router) from its own service provider or another service provider to handover or roam. Once the handover or roaming is completed it goes to 1001 or 1002 depending on circumstances.

At 1007 master IoT device shares the OID received from SOMC through the IoT network with NPS's controller. Then controller at 1008 activates slave IoT devices (wireless sensor, LIDAR sensor, Lidar sensor, Image sensor, ultrasonic sensor and other sensors/devices).

At 1009 slave IoT devices obtain OID which includes the time of day (TOD) from NPS's controller. The TOD is the same as master IoT device TOD and is exchanged between controller and slave IoT devices using IEEE1588 PTP messages. Slave IoT devices after synchronizing with master IoT device or controller and obtaining TOD continue at 1010.

At 1010 slave IoT devices or/and master IoT device receive all parameters, information for ranging, and all the absolute times for the time slots (OID) assigned to various objects in the smart environment. The absolute time is the start of time slot or time window and is a microsecond within millisecond. The time slot or time window shows the time period that assigned to the slave or/and the master IoT devices for receiving or transmitting a broadcast or an Ethernet packet, ranging using RADAR or LIDAR, ranging using an IoT ranging device (wireless sensor, IoT device 300, 400, 500, and 600), ultrasonic sensor and ranging using image sensor. All slave IoT devices or/and master IoT device within the NPS use their own time slot (assigned by SOMC) to transmit broadcast or Ethernet packets and time slots assigned to other NPSs to receive broadcast packets and receive or transmit Ethernet packets. Time slot also is used for ranging using at least one of an IoT ranging device, a RADAR, a Image sensor, a LIDAR, and ultrasonic sensor.

At 2011 all slave IoT ranging devices or/and master IoT ranging device (IoT ranging device can also be a RADAR, LIDAR, an image sensor/camera, and an ultrasonic sensor that belong to the object's NPS) begin to perform ranging during the time slot assigned to the object's NPS.

Each slave IoT ranging device during its own time slot begins transmitting ranging signal and receiving reflected ranging signal from objects in its surrounding environment and record the completion of transmitted ranging signal time of day (TOD) T1 at its antenna port. Ranging signal can have a synchronization preamble followed by a unique identification pattern (an IP address, an identification number of the object or random pattern). In order to provide higher resolution and accuracy the ranging signal can be divided into smaller segments. In this scenario T1 is the completion of the transmission TOD of the last segment of the ranging signal or pattern at the antenna port. The synchronization preamble is used to train the receiver and adjust it for accurate detection of each segment. The operating parameters for the IoT ranging device should be within the limits of coherence time and coherence bandwidth. It is also possible to use a ranging signal or pattern without a preamble pattern. It is also possible to repeat the raging a few times during the time window in the time slot assigned for ranging. If several complete ranging is performed then T1 is the TOD of last segment of ranging pattern or signal.

As mentioned above during the ranging time within the time slot the object can also use Radar sensor, Lidar sensor, ultrasonic sensor, and image sensor. IoT ranging, radar ranging, and ultrasonic ranging can be performed at the same time assigned for ranging. Lidar and image ranging can be performed at anytime during the time slot.

At 1012 Each slave IoT ranging device receives reflected ranging signal from objects, measures RSSI, records (averaged) RSSI and TOD T2 when reception completed at antenna port. When ranging signal is segmented for higher resolution or accuracy T2 is the last TOD when the last ranging segment arrived at the antenna port. And when several complete ranging performed during the ranging time window in the time slot then final TOD T2 belongs the last reflected ranging segment. This process can also be applied to Radar ranging, Lidar ranging, and image ranging.

At 1013 each slave IoT ranging device or/and master IoT device uses T1 and T2 to obtain an estimate of an object distance from IoT ranging device. Then slave IoT ranging device decides if the RSSI and estimated distance is within acceptable range. Similar process can also be applied to Radar ranging, Lidar ranging, ultrasonic ranging, and image ranging.

If RSSI and estimated distance are not within acceptable range then at 1017 slave IoT ranging device waits until the next time slot and process 2000 continues at 1011. Radar ranging, Lidar ranging, and image ranging may also follow the same step.

At 1014 each slave IoT ranging device detects all the reflected ranging segments and correlates with transmit ranging signal. Radar ranging, Lidar ranging, and Image ranging follow their own logic.

At 1015 slave IoT ranging device checks if there is a match between transmitted ranging pattern or signal and detected reflected signal. If there is no match then at 1017 slave IoT ranging device waits until next time slot and the process continues at 1011. Radar ranging, Lidar ranging, ultrasonic ranging, and Image ranging each follow its own logic for the next step.

At 1016 each slave IoT ranging device sends received reflected signal's RSSI with its associated TODs, T1, and T2 to the NPS's controller. Radar, Lidar, ultrasonic, and Image sensor if used each sends its own data to NPS's controller.

At 2018 controller receives the detected information data from all slave IoT ranging devices and activate its AI algorithm. At 1019 AI algorithm assesses all the data from slave IoT ranging devices and determines the nature of surrounding environment. The same process applies to Radar, Lidar, ultrasonic and Image sensor information data.

At 1020 controller determines if one or more slave IoT ranging device approaching an object in the smart environment. If none of the slave IoT ranging devices approaching an object then the process 2000 continues at 1017. The same process applies to Radar, Lidar, ultrasonic, or image sensor if one is used for ranging. At 1021 controller checks if IoT network has updated time slots and absolute times. If the answer is yes at 1022 controller shares new OID information with all slave IoT ranging devices (Radar, Lidar, ultrasonic, and image sensor if any used) and process continues at 1017.

At 1023 AI algorithm calculates distance between slave IoT ranging device and the object in the smart environment and identifies which slave IoT ranging devices requires to estimate approaching speed of the object. Same applies to Radar, Lidar, ultrasonic, or image sensor if used in this process.

At 1024 slave IoT ranging devices that need to estimate approaching speed of an object wait one or more measurement cycle and transmit its ranging signal (fragment). This process also applies to Radar, Lidar, ultrasonic, or image sensor if any of them used.

At 1025 slave IoT ranging device records completion time T1 of transmission of fragment at its antenna port. At 1026 slave IoT ranging device receives the reflected ranging signal fragment within receive time window and measures RSSI and records T2. Radar, Lidar, ultrasonic, or image sensors (if any of them used) each follow its own process.

At 1027 slave IoT ranging device checks if the last reflected segment is received. If the answer is no then slave IoT ranging device stores the information and process 2000 continues at 1024 for next fragment. Radar, Lidar, ultrasonic, or image sensors (if used) each follow its own process.

At 1028 slave IoT ranging device averages RSSI of all segments for one complete measurement, records T2s and detects the received reflected signal from the reflected fragments. Radar, Lidar, ultrasonic, or image sensor if any of them used each follow its own process.

At 1029 slave IoT ranging device checks if more complete ranging is required. If the answer is yes then process 2000 continues at 1024. Radar, Lidar, ultrasonic, or image sensors (if used) each follow its own process.

At 1030 slave IoT ranging device checks if the received reflected ranging signal matched the transmit ranging signal. If none of received reflected ranging signals matches then start over and continue process 2000 at 1011. If the answer is positive then at 1031 send all RSSIs, T1s, T2s belonging to all fragments to controller. Radar, Lidar, ultrasonic, or image sensors (if used) each follow its own process and start over the process 2000 at 1011 or send measured information to the controller.

At 1032 controller receives all the detected information data from slave IoT ranging devices and feeds them to navigation and protection system's AI algorithm in order to perform the next step. The same process applies to Radar, Lidar, ultrasonic, or image sensors if any of them used.

At 1033 the controller checks if IoT network has updated time slots and absolute times. If update has occurred then at 1034 controller shares the new OID data with slave IoT ranging devices (and with Radar, Lidar, ultrasonic, or image sensors if any used) and/or master IoT device and then process continues at 1011.

At 1035 the AI algorithm determines if it has enough information to make a decision. If there is not sufficient information then AI algorithm updates OID for each individual slave IoT ranging device (and for Radar, Lidar, ultrasonic, or image sensors if any used) and/or master IoT device and the process continues at 1011.

At 1036 the AI algorithm calculates distance and approaching speed of objects that are approaching slave IoT ranging devices (and for Radar, Lidar, ultrasonic, or image sensors if any used).

At 1037 the AI algorithm examines if both distance & approaching speed of an object detected by a slave IoT ranging device (and Radar, Lidar, ultrasonic, or image sensors if any used) meet certain threshold. If it does not meet then the process continues at 1041.

At 1038 the AI algorithm checks if there is an imminent impact. If there is not then the process continues at 1041.

At 1039 the AI algorithm analyses the entire detected information data (DID) and activates the appropriate protection devices.

At 1040 the AI algorithm through NPS's controller and maser IoT device reports to the IoT network, then NPS waits for next step from IoT network. At this point when it is appropriate the NPS resets and at the right time start process 2000 at 1001.

At 1041 the AI algorithm determines whether more information is needed in order to activate navigation devices such as steering wheel, break, accelerator, and etc. If there is not enough DID to decide then process 2000 continues at 1044.

At 1044 the AI algorithms identifies the necessary operation information data (OID) for each slave (and for Radar, Lidar, ultrasonic, or image sensors if any used) and/or master IoT ranging device and sends it to them through controller. Once each individual slave IoT ranging device (and Radar, Lidar, ultrasonic, or image sensors if any used) or master IoT device is provided with its new OID then the process continues at 1011.

At 1042 due to sufficient information for AI algorithm, navigation system is activated and more information data from surrounding environment is collected by other internal and external sensors used by NPS for the AI algorithm. AI algorithm uses all the detected information data (DID) and provides required changes to various navigation devices such as steering wheel, break, accelerator, and etc.

At 1043 AI algorithm determines if there is any changes to the OID for each individual IoT device (or Radar, Lidar, ultrasonic, or image sensors if any used) due to activating navigation. If there are not any changes then process 2000 continues at 1011.

At 1045 AI algorithm sends the updated OID to each IoT ranging device (and Radar, Lidar, ultrasonic, or image sensors if any used) through controller and the process 2000 continues at 1011.

Various embodiments are thus described. While particular embodiments have been described, it should be appreciated that the embodiments should not be construed as limited by such description, but rather construed according to the following claims.

The invention claimed is:

1. A navigation and protection system (NPS) used by an object in a smart environment comprising:
    a master Internet of Things (IoT) device to communicate with an IoT network and obtain a time of day (TOD) and an operation information data (OID) that includes an absolute time and a time slot window for the NPS;
    said time slot starts at the TOD specified by said absolute time and has a structure that consists of at least one of a ranging window, a communication window, and a guard time;
    a plurality of slave IoT ranging devices to transmit a ranging signal and receive a reflected ranging signal during said ranging window within said time slot specified by said NPS and obtain a detected information data (DID) related to the objects in the smart environment;
    a controller in a central processor unit (CPU) to manage said navigation and protection system and to:
        synchronize with the master IoT device to obtain said TOD and said operation information data;
        share the operation information data and the TOD with a slave IoT ranging device within said plurality of slave IoT ranging devices;
        record said detected information data provided by said slave IoT ranging device within said plurality of slave IoT ranging devices; and
        feed said operation information data and said detected information data to an algorithm that is executed by the controller;
    said algorithm uses said operation information data and said detected information data to:
        assess the smart environment parameters;
        activate a protection device used by said NPS when an impact is imminent;
        activate a navigation device to avoid the impact; or
        update the operation information data and send it to said slave IoT ranging device through said controller.

2. The navigation and protection system of claim 1, wherein said object is at least one of a moving vehicle, a flying vehicle, a stationary object, a robot, and a live animal (human).

3. The navigation and protection system of claim 1, wherein said IoT network is at least one of a fifth generation (5G) network, a sixth generation (6G) network, a seventh generation (7G) network, a beyond 5G network, a WiFi (wireless fidelity) network, and a private network.

4. The navigation and protection system of claim 1, wherein said absolute time is at least one of a $1^{st}$ microsecond in a millisecond, a $K_{th}$ microsecond in a millisecond, and a $N_{th}$ microsecond in a millisecond of said TOD.

5. The navigation and protection system of claim 1, wherein said communication window within said time slot is used for at least one of ranging, communication with said controller, broadcasting, obtaining said TOD from said controller, and communication with other said slave IoT ranging devices.

6. The navigation and protection system of claim 2, wherein said plurality of slave IoT ranging devices and said master IoT device are attached to an external body of said object and communicate with said controller to receive said operation information data and to transmit said detected information data to be used by the algorithm.

7. The navigation and protection system of claim 1, wherein said operation information data includes at least one of said absolute time for the start of said time slot, a time window assigned to said guard time, duration of the ranging window, duration of said communication window, said ranging signal, a ranging radius, a period to monitor said reflected ranging signal, an operating frequency, a channel, a bandwidth, a modulation, and an effective radiation power (ERP).

8. The navigation and protection system of claim 1, wherein said ranging signal is at least one of a FMCW (frequency modulated continue wave) signal, a continuous wave (CW) signal, a pulsed signal, a Laser signal, a ranging pattern, and a broadcast or/and an Ethernet packet.

9. The navigation and protection system of claim 8, wherein said ranging pattern is a unique IP (Internet Protocol) address, a serial number, or a random bit pattern that has a preamble.

10. The navigation and protection system of claim 1, wherein said DID is used to estimate a distance and an approaching speed of an object in the smart environment towards said NPS and includes at least one of a received signal strength intensity (RSSI) of said reflected ranging signal, a completion transmission time (TOD) of said ranging signal, and a completion reception time (TOD) of said reflected ranging signal.

11. The navigation and protection system of claim 1, wherein said algorithm in addition to said DID uses data from other sensors or/and devices internal and external to said object to determine if there is a need to activate said protection device or/and said navigation device.

12. The navigation and protection system of claim 1, wherein said slave IoT ranging device is at least one of a wireless sensor, a RADAR (Radio Detection and Ranging), a LIDAR (Light Detection and Ranging), an image sensor, and an ultrasonic sensor.

13. A method for navigating and protecting an object in a smart environment, the method comprising:
    installing a navigation and protection system (NPS) on the object that receives an operation information data (OID) from an IoT network through a master IoT device that includes a time of day (TOD), an absolute time, and a time slot;
    monitoring the smart environment of the object by the NPS's ranging devices that are mounted external to the object;
    obtaining a detected information data (DID) from an Internet of Thing (IoT) ranging device that transmits a ranging signal and receives a reflected ranging signal during said time slot; and
    using an algorithm within the NPS's central processor unit (CPU) to:
        process said detected information data (DID) obtained from all the NPS's sensors or devices;

determine if more said DID is required and request from the NPS's sensors or devices by sending them an updated OID;

estimate a distance and an approaching speed of said objects in said smart environment using the DID provided by the NPS's sensors or devices;

detect an imminent impact and then activate a protection device; or activate a navigation device if a potential impact is detected.

14. The method of claim 13, wherein said IoT ranging devices, and the protection devices are mounted on external locations of a body of the object.

15. The method of claim 13, wherein said protection device is at least one of a multilayer airbag, a compressed air, and an expandable pad.

16. The method of claim 13, wherein said navigation device is at least one of a steering wheel, an accelerator, a break, a horn, and a beam light.

* * * * *